(12) United States Patent
Wacker et al.

(10) Patent No.: US 8,372,837 B2
(45) Date of Patent: Feb. 12, 2013

(54) PYRIDONE AND PYRIDAZONE ANALOGUES AS GPR119 MODULATORS

(75) Inventors: Dean A. Wacker, Yardley, PA (US); Karen A. Rossi, Newtown, PA (US); Ying Wang, New Hope, PA (US); Gang Wu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1 day.

(21) Appl. No.: 13/003,914

(22) PCT Filed: Jul. 15, 2009

(86) PCT No.: PCT/US2009/050618
§ 371 (c)(1),
(2), (4) Date: Jun. 1, 2011

(87) PCT Pub. No.: WO2010/009183
PCT Pub. Date: Jan. 21, 2010

(65) Prior Publication Data
US 2011/0263548 A1    Oct. 27, 2011

Related U.S. Application Data

(60) Provisional application No. 61/081,058, filed on Jul. 16, 2008, provisional application No. 61/081,060, filed on Jul. 16, 2008, provisional application No. 61/081,069, filed on Jul. 16, 2008.

(51) Int. Cl.
C07D 401/12 (2006.01)
C07D 401/14 (2006.01)
A61K 31/501 (2006.01)
A61P 7/12 (2006.01)
A61P 3/10 (2006.01)
A61P 3/04 (2006.01)

(52) U.S. Cl. ............... 514/252.02; 514/252.03; 544/238
(58) Field of Classification Search ............ 514/252.03, 514/252.02; 544/238
See application file for complete search history.

(56) References Cited

U.S. PATENT DOCUMENTS

| | | | |
|---|---|---|---|
| 3,826,643 A | 7/1974 | Diehl et al. | |
| 5,488,064 A | 1/1996 | Sher | |
| 5,491,134 A | 2/1996 | Sher et al. | |
| 5,541,204 A | 7/1996 | Sher et al. | |
| 5,612,359 A | 3/1997 | Murugesan | |
| 5,770,615 A | 6/1998 | Cheng et al. | |
| 5,776,983 A | 7/1998 | Washburn et al. | |
| 6,043,265 A | 3/2000 | Murugesan et al. | |
| 6,566,384 B1 | 5/2003 | Owen et al. | |
| 2003/0181420 A1 | 9/2003 | Bayne et al. | |
| 2005/0080111 A1 | 4/2005 | Bayne et al. | |
| 2005/0245515 A1 | 11/2005 | Dehmlow et al. | |
| 2006/0155128 A1 | 7/2006 | Jones et al. | |
| 2006/0292073 A1 | 12/2006 | Goodman et al. | |
| 2011/0257394 A1* | 10/2011 | Kawahara et al. | ............ 544/238 |

FOREIGN PATENT DOCUMENTS

| | | |
|---|---|---|
| EP | 1 338 651 | 8/2003 |
| WO | WO 96/38144 | 12/1996 |
| WO | WO 97/12613 | 4/1997 |
| WO | WO 97/12615 | 4/1997 |
| WO | WO 99/26659 | 6/1999 |
| WO | WO 00/01389 | 1/2000 |
| WO | WO 00/39102 | 7/2000 |
| WO | WO 02/02519 | 1/2002 |
| WO | WO 2004/065380 | 8/2004 |
| WO | WO 2004/076413 | 9/2004 |
| WO | WO 2004/089885 | 10/2004 |
| WO | WO 2005/007647 | 1/2005 |
| WO | WO 2005/007658 | 1/2005 |
| WO | WO 2005/025504 | 3/2005 |
| WO | WO 2005/089786 | 9/2005 |
| WO | WO 2005/121121 | 12/2005 |
| WO | WO 2006/067532 | 6/2006 |
| WO | WO 2006/083491 | 8/2006 |
| WO | WO2007/003961 | 1/2007 |
| WO | WO2009/012275 | 1/2009 |

(Continued)

OTHER PUBLICATIONS

Semple, et al., J. Med. Chem., 2008, 51, 5172-5175.*

(Continued)

*Primary Examiner* — Susanna Moore
*Assistant Examiner* — Cecilia M Jaisle
(74) *Attorney, Agent, or Firm* — Terence J. Bogie

(57) ABSTRACT

Novel compounds of structure Formula (I) or an enantiomer, a diastereomer, or a pharmaceutically acceptable salt thereof, wherein Z, $R^1$, $R^2$, $R^{21}$, $T^1$, $T^2$, $T^3$ and $T^4$ are defined herein, are provided which are GPR119 G protein-coupled receptor modulators. GPR119 G protein-coupled receptor modulators are useful in treating, preventing, or slowing the progression of diseases requiring GPR119 G protein-coupled receptor modulator therapy. Thus, the disclosure also concerns compositions comprising these novel compounds and methods of treating diseases or conditions related to the activity of the GPR119 G protein-coupled receptor by using any of these novel compounds or a composition comprising any of such novel compounds.

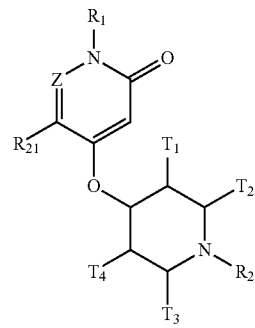

I

15 Claims, No Drawings

FOREIGN PATENT DOCUMENTS

WO    WO2009/012277    1/2009

OTHER PUBLICATIONS

Fyfe, et al., New Nonpeptide-Binding GPCRs as Targets for Diabetes and the Metabolic Syndrome, 2007, 129-145.*
Lan, et al., J. Endocrinology, May 1, 2009, 201, 219-230.*
Alex, "GPR119: A Novel Means to Lower Intraocular Pressure?," Grant 1R21EY021831-01 from National Eye Institute, 2011.*
Madiraju, et al., Endocrinology 148(6):2598-2600, 2007.*
Jones, et al., Expert Opin. Ther. Patents (2009) 19(10).*
Straiker, GPR119: A Novel Means to Lower Intraocular Pressure?, Grant 1R21EY021831-01 from National Eye Institute, 2011.*
Overton, et al., Br. J. Pharmacol., Mar. 2008; 153(S1): S76-S81.*
Ahrén, B., "Autonomic regulation of islet hormone secretion—Implications for health and disease", Diabetologia, vol. 43, pp. 393-410 (2000).
Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).
Boger, D.L. et al., "Total Syntheses of Azafluoranthene Alkaloids: Rufescine and Imeluteine", J. Org. Chem., vol. 49, No. 21, pp. 4050-4055 (1984).
Brancati, F.L. et al., "Body Weight Patterns from 20 to 49 Years of Age and Subsequent Risk for Diabetes Mellitus", Arch. Intern. Med., vol. 159, pp. 957-963 (1999).
Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).
Bundgaard, H., ed., Design of Prodrugs, Elsevier Science Publishers B.V., publ. (1985) (table of contents).
Butler, A.E. et al., "β-Cell Deficit and Increased β-Cell Apoptosis in Humans with Type 2 Diabetes", Diabetes, vol. 52, pp. 102-110 (2003).
Chu, Z.-L. et al., "A Role for β-Cell-Expressed G Protein-Coupled Receptor 119 in Glycemic Control by Enhancing Glucose-Dependent Insulin Release", Endocrinology, vol. 148, No. 6, pp. 2601-2609 (2007).
Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).
Deng, H. et al., "Aryllead(IV) Reagents in Synthesis: Formation of the C11 Quaternary Center of N-Methylwelwitindolinone C Isothiocyanate", Organic Letters, vol. 3, No. 19, pp. 3001-3004 (2001).
Donetti, A. et al., "(Imidazolylphenyl)formamidines. A Structurally Novel Class of Potent Histamine $H_2$ Antagonists", J. Med. Chem., vol. 27, No. 3, pp. 380-386 (1984).
Ford, E.S. et al., "Prevalence of the Metabolic Syndrome Among US Adults", Journal of the American Medical Association, vol. 287, No. 3, pp. 356-359 (2002).
Fredriksson, R. et al., "Seven evolutionary conserved human rhodopsin G protein-coupled receptors lacking close relatives", FEBS Letters, vol. 554, pp. 381-388 (2003).
Frlan, R. et al., "Recent Progress in Diaryl Ether Synthesis", Synthesis, No. 14, pp. 2271-2285 (2006).
Gennaro, A.R., ed., Remington's Pharmaceutical Sciences, 17th Edition, Mack Publishing Company, publ., p. 1418 (1985).
Gomtsyan, A. et al., "Design, Synthesis, and Structure-Activity Relationship of 6-Alkynylpyrimidines as Potent Adenosine Kinase Inhibitors", J. Med. Chem., vol. 45, No. 17, pp. 3639-3648 (2002).
Greene, T.W. et al., Protective Groups in Organic Synthesis, Second Edition, John Wiley & Sons, Inc., publ., pp. ix-x (table of contents) (1991).
Haning, H. et al., "Novel heterocyclic thyromimetics", Bioorganic & Medicinal Chemistry Letters, vol. 15, pp. 1835-1840 (2005).
Hara, S., "Ileal $Na^+$/bile acid cotransporter inhibitors", Drugs of the Future, vol. 24, No. 4, pp. 425-430 (1999).
Hertzog, D.L., "Recent advances in the cannabinoids", Expert Opin. Ther. Patents, vol. 14, No. 10, pp. 1435-1452 (2004).
Hill, J.O. et al., "Environmental Contributions to the Obesity Epidemic", Science, vol. 280, pp. 1371-1374 (1998).
Hong, C.Y. et al., "Asymmetric Synthesis of Either Enantiomer of Opium Alkaloids and Morphinans. Total Synthesis of (−)- and (+)-Dihydrocodeinone and (−)- and (+)-Morphine", J. Am. Chem. Soc., vol. 115, No. 23, pp. 11028-11029 (1993).
Itoh, T. et al., "A General Palladium-Catalyzed Coupling of Aryl Bromides/Triflates and Thiols", Organic Letters, vol. 6, No. 24, pp. 4587-4590 (2004).
Jiang, G. et al., "Prevention of obesity in mice by antisense oligonucleotide inhibitors of stearoyl-CoA desaturase-1", The Journal of Clinical Investigation, vol. 115, No. 4, pp. 1030-1038 (2005).
Justus, K. et al., "First Synthesis of a Strained 14-Membered Biaryl Ether Lactone by Macrolactonization", Tetrahedron Letters, vol. 32, No. 14, pp. 5781-5784 (1991).
Katritzky, A.R. et al., "Efficient Transformations of Aldehydes and Ketones into One-Carbon Homologated Carboxylic Acids", Synthesis, pp. 1425-1427 (1996).
Ketcha, D.M. et al., "The Reduction of N-(phenylsulfonyl)indoles with Sodium Cyanoborohydride in Trifluoroacetic Acid", Tetrahedron Letters, vol. 30, No. 49, pp. 6833-6836 (1989).
Le Stunff, C. et al., "Early Changes in Postprandial Insulin Secretion, Not in Insulin Sensitivity, Characterize Juvenile Obesity", Diabetes, vol. 43, pp. 696-702 (1994).
Magnus, P. et al., "Studies on the Synthesis of the Antitumor Agent CC-1065. Synthesis of the Unprotected Cyclopropapyrroloindole A Portion Using the 3,3'-Bipyrrole Strategy", J. Am. Chem. Soc., vol. 109, No. 9, pp. 2706-2711 (1987).
NCBI Entrez Accession No. AAP72125 (gi:32165516), Fredriksson, R. et al., Dec. 8, 2003.
NCBI Entrez Accession No. AY288423 (gi:32165529), Fredriksson, R. et al., Dec. 8, 2003.
Nishio, T. et al., "Reduction of Indolin-2-ones and Desulfurization of Indoline-2-thiones to Indoline and Indole Derivatives", Helvetica Chimica Acta, vol. 73, pp. 1719-1723 (1990).
Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., vol. 43, No. 22, pp. 4288-4312 (2000).
Overton, H.A. et al., "Deorphanization of a G protein-coupled receptor for oleoylethanolamide and its use in the discovery of small-molecule hypophagic agents", Cell Metabolism, vol. 3, pp. 167-175 (2006).
Pedersen, O., "The Impact of Obesity on the Pathogenesis of Non-Insulin-Dependent Diabetes Mellitus: A Review of Current Hypotheses", Diabetes/Metabolism Reviews, vol. 5, No. 6, pp. 495-509 (1989).
Perry, I.J. et al., "Prospective study of risk factors for development of non-insulin dependent diabetes in middle aged British men", BMJ, vol. 310, pp. 560-564 (1995).
Prentki, M. et al., "Islet β cell failure in type 2 diabetes", The Journal of Clinical Investigation, vol. 116, No. 7, pp. 1802-1812 (2006).
Radinov, R. et al., "Lithiation of Polychloropyrimidines and Dichloropyridines", J. Org. Chem., vol. 56, No. 15, pp. 4793-4796 (1991).
Schubert, U., "The Homologation of Hagemann's Ester", Synthesis, pp. 364-365 (1978).
Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).
Sirowej, H. et al., "Preparation of substituted indoles by reduction of isatin and oxindole derivatives with diborane/tetrahydrofuran", Synthesis, No. 2, p. 84 (1972).
Soga, T. et al., "Lysophosphatidylcholine enhances glucose-dependent insulin secretion via an orphan G-protein-coupled receptor", Biochemical and Biophysical Research Communications, vol. 326, pp. 744-751 (2005).
Takahashi, K. et al., "Efficient Method for a One-Carbon Homologation of Aldehydes and Benzophenone to Carboxylic Acids", J. Org. Chem., vol. 48, No. 20, pp. 3566-3569 (1983).

Testa, B. et al., Hydrolysis in Drug and Prodrug Metabolism: Chemistry, Biochemistry, and Enzymology, Wiley-VCH GmbH & Co., publ., pp. xi-xx (table of contents) (2003).

Urgaonkar, S. et al., "Application of a New Bicyclic Triaminophosphine Ligand in Pd-Catalyzed Buchwald-Hartwig Amination Reactions of Aryl Chlorides, Bromides, and Iodides", J. Org. Chem. vol. 68, No. 22, pp. 8416-8423 (2003).

Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).

Yang, B.H. et al., "Palladium-catalyzed amination of aryl halides and sulfonates", Journal of Organometallic Chemistry, vol. 576, pp. 125-146 (1999).

Young, S.D. et al., "L-743,726 (DMP-266): a Novel, Highly Potent Nonnucleoside Inhibitor of the Human Immunodeficiency Virus Type 1 Reverse Transcriptase", Antimicrobial Agents and Chemotherapy, vol. 39, No. 12, pp. 2602-2605 (1995).

Zhang, X. et al., "Dimethyldioxirane Oxidation of Indole Derivatives. Formation of Novel indole-2,3-epoxides and a Versatile Synthetic Route to Indolinones and Indolines", J. Am. Chem. Soc., vol. 115, No. 19, pp. 8867-8868 (1993).

West, Anthony R., "Solid State Chemistry and its Applications," Wiley, New York, 1988, pp. 358 & 365.

* cited by examiner

PYRIDONE AND PYRIDAZONE ANALOGUES AS GPR119 MODULATORS

CROSS REFERENCES TO RELATED APPLICATIONS

This application claims the benefit of U.S. Provisional Application Ser. Nos. 61/081,058, 61/081,060, and 61/081,069, all filed on Jul. 16, 2008, which are hereby incorporated by reference in their entirety.

FIELD OF THE INVENTION

The present invention provides novel pyridone and pyridazone compounds and analogues, which are modulators of the GPR119 G protein-coupled receptor, compositions containing them, and methods of using them, for example, for the prevention and/or treatment of diseases or disorders associated with the activity of the GPR119 G protein-coupled receptor, e.g., diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., *Diabetes,* 43:696-702 (1989)). However, over time, β-cell function deteriorates and non-insulin-dependent diabetes develops in about 20% of the obese population (Pederson, P., *Diab. Metab. Rev.,* 5:505-509 (1989)) and (Brancati, F. L. et al., *Arch. Intern. Med.,* 159: 957-963 (1999)). Given its high prevalence in modern societies, obesity has thus become the leading risk factor for NIDDM (Hill, J. O. et al., *Science,* 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., *BMJ,* 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", *J. Clin. Invest.,* 116: 1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cellapoptosis in humans with type 2 diabetes", *Diabetes,* 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Ahren, B., "Autonomic regulation of islet hormone secretion—Implications for health and disease", *Diabetologia,* 43:393-410 (2003)). Those GPCRs specifically coupled to the elevation of cAMP via the $G_s$ alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in $K^+$ efflux depolarizes the β-cell leading to an influx of $Ca^{++}$ which promotes the release of insulin.

GPR119 (e.g., human GPR119, GENBANK® Accession No. AAP72125 and alleles thereof; e.g., mouse GPR119, GENBANK® Accession No. AY288423 and alleles thereof) is a GPCR located at chromosome position Xp26.1 (Fredricksson, R. et al., "Seven evolutionarily conserved human rhodopsin G protein-coupled receptors lacking close relatives", *FEBS Lett.,* 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.,* 326:744-751 (2005), international patent applications WO 04/065380, WO 04/076413, WO 05/007647, WO 05/007658, WO 05/121121, WO 06/083491 and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan G-protein-coupled receptor", *Biochem. Biophys. Res. Comm.,* 326:744-751 (2005); Chu, Z. L. et al., "A role for β-cell-expressed GPR119 in glycemic control by enhancing glucose-dependent insulin release", *Endocrinology,* doi:10.1210/en.2006-1608 (2007)).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for β-cell-expressed GPR119 in glycemic control by enhancing glucose-dependent insulin release", *Endocrinology, doi:*10.1210/en.2006-1608 (2007)). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism,* 3:167-175 (2006), and international patent applications WO 05/007647 and WO 05/007658).

SUMMARY OF THE INVENTION

In accordance with the present invention, compounds are provided that have the general structure of Formula I:

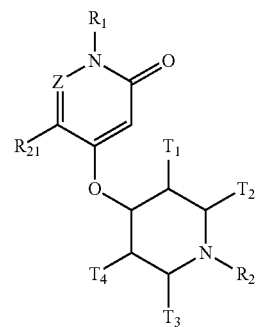

or an enantiomer, a diastereomer, or a pharmaceutically acceptable salt thereof, wherein Z, $R^1$, $R^2$, $R^{21}$, $T^1$, $T^2$, $T^3$ and $T^4$ are defined below.

Compounds of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In addition, the present invention relates to a formulated product wherein the selected formulation is made by using a compound of Formula I as the only active ingredient or by combining (a) a compound of Formula I (using any of the compound embodiments listed herein) and (b) an additional active ingredient, for example, dipeptidyl peptidase-IV (DPP4) inhibitor (for example a member selected from saxagliptin, sitagliptin, vildagliptin and alogliptin).

Therefore, in another aspect the present invention provides for compounds of Formula I, pharmaceutical compositions containing such compounds, and for methods of using such compounds. In particular, the present invention provides a pharmaceutical composition comprising a therapeutically effective amount of a compound of Formula I, alone or in combination with a pharmaceutically acceptable carrier.

Further, in another aspect the present invention provides a method for preventing, modulating, or treating the progression or onset of diseases or disorders associated with the activity of the GPR119 G protein-coupled receptor, such as defined above and hereinafter, wherein a therapeutically effective amount of a compound of Formula I is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I and another compound of Formula I and/or at least one other type of therapeutic agent, is administered to a mammalian, i.e., human, patient in need of treatment.

DETAILED DESCRIPTION OF THE INVENTION

In the first aspect of the present invention, compounds of Formula I are provided:

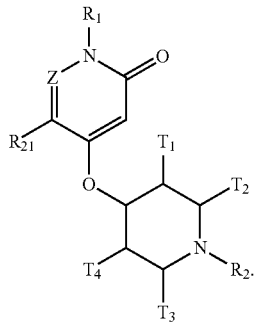

In the first embodiment of the first aspect, the present invention provides a compound of Formula I, or an enantiomer, a diastereomer, or a pharmaceutically acceptable salt thereof, wherein:

Z is CH or N;

$R^1$ is aryl, arylalkyl or heteroaryl, any of which may be optionally substituted with one or more $R^6$'s;

$R^2$ is cycloalkyl, aryl, heteroaryl, heterocyclyl, —S(O)$_2$R$^5$, —C(=O)NR$^3$R$^5$, —C(=O)R$^5$ or —C(=O)OR$^5$, wherein the cycloalkyl, aryl, heteroaryl and heterocyclyl may each be optionally substituted with one or more $R^6$'s;

$R^3$ is hydrogen, alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl and heterocyclylalkyl may each contain 1-4 heteroatoms selected from N, O and S;

$R^5$ is alkyl, alkenyl, aryl, cycloalkyl, heteroaryl or heterocyclyl, each of which may be optionally substituted with one or more $R^6$'s;

$R^6$, at each occurrence, is independently selected from alkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —S(O)$_3$H, —P(O)$_3$H$_2$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(=NR$^{14}$)NR$^9$R$^9$, —NHC(=NR$^{14}$)NR$^{14}$R$^{14}$, —S(=O)R$^{10}$, —S(O)$_2$R$^{10}$, =O, —NR$^9$C(=O)OR$^8$ and —NR$^9$S(O$_2$)R$^8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R^{9a}$;

$R^8$, at each occurrence, is independently selected from the group consisting of alkyl, aryl, cycloalkyl, heteroaryl and heterocyclyl, each of which may be optionally substituted with one or more $R^{8a}$'s;

$R^{8a}$, at each occurrence, is independently selected from alkyl, haloalkyl, aryl, arylalkyl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, alkenyl, alkynyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R^{8a}$, and the heteroaryl, heteroarylalkyl, heterocyclyl and heterocyclylalkyl each contain 1-4 heteroatoms selected from N, O and S;

$R^{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R^{10a}$, and the heteroaryl, heteroarylalkyl, heterocyclyl and heterocyclylalkyl each contain 1-4 heteroatoms selected from N, O and S;

$R^{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^1$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl, heteroaryl and heterocyclyl;

$R_{21}$ is hydrogen, alkyl, haloalkyl, hydroxyalkyl, aryl, cycloalkyl, halo, —CN, —C(=O)OH, —C(=O)OR$^{10}$, —OCF$_3$, —OCHF$_2$, —OR$^{10}$, —OH, —C(=O)NR$^9$R$^9$, —C(=O)R$^{10}$ or —OC(=O)R$^{10}$;

T$_1$ is hydrogen, halo, alkyl, aryl, alkenyl or alkynyl, wherein the alkyl, aryl, alkenyl and alkynyl may be optionally substituted with one or more R$^6$'s;

T$_2$ is hydrogen, alkyl, aryl, alkenyl or alkynyl, wherein the alkyl, aryl, alkenyl and alkynyl may be optionally substituted with one or more R$^6$'s;

T$_3$ is hydrogen, alkyl, aryl, alkenyl or alkynyl, wherein the alkyl, aryl, alkenyl and alkynyl may be optionally substituted with one or more R$^6$'s; and T$_4$ is hydrogen, halo, alkyl, aryl, alkenyl or alkynyl, wherein the alkyl, aryl, alkenyl and alkynyl may be optionally substituted with one or more R$^6$'s;

provided that when Z is CH and R$^1$ is a 5- to 6-membered aryl or heteroaryl, T$^1$, T$^2$, T$^3$, and T$^4$ can not all be hydrogen.

The terms "Formula I" and all embodiments thereof shall include enantiomers, diastereomers, solvates and salts thereof (particularly enantiomers, diastereomers and pharmaceutically acceptable salts thereof).

In a second embodiment of the first aspect, the present invention provides a compound of Formula I, or an enantiomer, a diastereomer, or a pharmaceutically acceptable salt thereof, wherein R$^1$ is a 5- or 6-membered aryl, a 5- or 6-membered arylalkyl or a 5- to 10-membered heteroaryl, any of which may be optionally substituted with one or more R$^6$'s.

In a third embodiment of the first aspect, the present invention provides a compound of Formula I, or an enantiomer, a diastereomer, or a pharmaceutically acceptable salt thereof, wherein R$^1$ is a 5- or 6-membered aryl or a 5- to 10-membered heteroaryl, both of which may be optionally substituted with one or more R$^6$'s.

In a fourth embodiment of the first aspect, the present invention provides a compound of Formula I, or an enantiomer, a diastereomer, or a pharmaceutically acceptable salt thereof, wherein R$^1$ is 9-membered bicyclic heteroaryl, which may be optionally substituted with one or more R$^6$'s.

In a fifth embodiment of the first aspect, the present invention provides a compound of Formula I, or an enantiomer, a diastereomer, or a pharmaceutically acceptable salt thereof, wherein the compound of formula I is a compound of formula II(y):

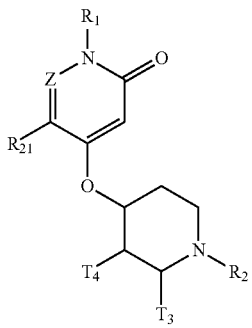

II(y)

wherein Z, R$_1$, R$_2$, R$_{21}$, T$^3$ and T$^4$ are defined as set forth above.

In a sixth embodiment of the first aspect, the present invention provides a compound of Formula I, or an enantiomer, a diastereomer, or a pharmaceutically acceptable salt thereof, wherein the compound of formula I is a compound of formula II(z):

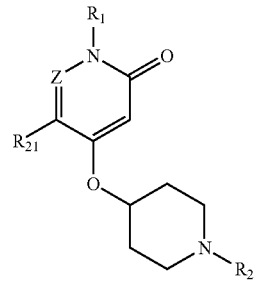

II(z)

wherein Z, R$_1$, R$_2$, and R$_{21}$ are defined as set forth above.

In a seventh embodiment of the first aspect, the present invention provides a compound of Formula I, or an enantiomer, a diastereomer, or a pharmaceutically acceptable salt thereof, wherein:

Z is CH or N;

R$^1$ is aryl, arylalkyl or heteroaryl, any of which may be optionally substituted with one or more R$^6$'s;

R$^2$ is cycloalkyl, aryl, heteroaryl, heterocyclyl, —S(O)$_2$R$^5$, —C(=O)R$^5$ or —C(=O)OR$^5$, wherein the cycloalkyl, aryl, heteroaryl and heterocyclyl may each be optionally substituted with one or more R$^6$'s;

R$^5$ is alkyl, alkenyl, aryl, cycloalkyl, heteroaryl or heterocyclyl, each of which may be optionally substituted with one or more R$^6$'s;

R$^6$, at each occurrence, is independently selected from alkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —S(O)$_3$H, —P(O)$_3$H$_2$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(=NR$^{14}$)NR$^9$R$^9$, —NHC(=NR$^{14}$)NR$^{14}$R$^{14}$, —S(=O)R$^{10}$, —S(O)$_2$R$^{10}$ and =O, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O) OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O) NR$^{14}$S(O)$_2$R$^{14}$, —S(O)$_2$NR$^{14}$C(=O)OR$^{14}$, —S(O)$_2$NR$^{14}$C (=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

R$^9$, at each occurrence, is independently selected from hydrogen, alkyl, alkenyl, alkynyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$^{8a}$, and the heteroaryl, heteroarylalkyl, heterocyclyl and heterocyclylalkyl each contain 1-4 heteroatoms selected from N, O and S;

R$^{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$^{10a}$, and the heteroaryl, heteroarylalkyl, heterocyclyl and heterocyclylalkyl each contain 1-4 heteroatoms selected from N, O and S;

R$^{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl, heteroaryl and heterocyclyl;

R$_{21}$ is hydrogen, alkyl, haloalkyl, hydroxyalkyl, aryl, cycloalkyl, halo, —CN, —C(=O)OH, —C(=O)OR$^{10}$, —OCF$_3$, —OR$^{10}$, —OH, —C(=O)NR$^9$R$^9$, —C(=O)R$^{10}$ or —OC(=O)R$^{10}$, T$_1$ is hydrogen, alkyl, aryl, alkenyl or alkynyl, wherein the alkyl, aryl, alkenyl and alkynyl may be optionally substituted with one or more R$^6$'s;

T$_2$ is hydrogen, alkyl, aryl, alkenyl or alkynyl, wherein the alkyl, aryl, alkenyl and alkynyl may be optionally substituted with one or more R$^6$'s;

T$_3$ is hydrogen, alkyl, aryl, alkenyl or alkynyl, wherein the alkyl, aryl, alkenyl and alkynyl may be optionally substituted with one or more R$^6$'s; and T$_4$ is hydrogen, alkyl, aryl, alkenyl or alkynyl, wherein the alkyl, aryl, alkenyl and alkynyl may be optionally substituted with one or more R$^6$'s.

In an eighth embodiment of the first aspect, the present invention provides a compound of Formula I, or an enantiomer, a diastereomer, or a pharmaceutically acceptable salt thereof, wherein:

Z is CH or N;

R$^1$ is aryl, arylalkyl or heteroaryl, any of which may be optionally substituted with one or more R$^6$'s;

R$^2$ is cycloalkyl, aryl, heteroaryl, heterocyclyl, —C(=O)R$^5$ or —C(=O)OR$^5$, wherein the cycloalkyl, aryl, heteroaryl and heterocyclyl may each be optionally substituted with one or more R$^6$'s;

R$^5$ is alkyl, aryl, cycloalkyl, heteroaryl or heterocyclyl, each of which may be optionally substituted with one or more R$^6$'s;

R$^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —S(O)$_3$H, —P(O)$_3$H$_2$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)R$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(=NR$^{14}$)NR$^9$R$^9$, —NHC(=NR$^{14}$)NR$^{14}$R$^{14}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, =O, —NR$^{14}$C(=O)OR$^{14}$ and —NR$^{14}$S(O)$_2$R$^{14}$;

R$^9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$^{8a}$, and the heteroaryl, heteroarylalkyl, heterocyclyl and heterocyclylalkyl each contain 1-4 heteroatoms selected from N, O and S;

R$^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$^{10a}$, and the heteroaryl, heteroarylalkyl, heterocyclyl and heterocyclylalkyl each contain 1-4 heteroatoms selected from N, O and S;

R$^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl, heteroaryl and heterocyclyl;

$R_{21}$ is hydrogen, alkyl, haloalkyl, hydroxyalkyl, aryl, cycloalkyl, halo, —CN, —C(=O)OH, —C(=O)OR$^{10}$, —OCF$_3$, —OR$^{10}$, —OH, —C(=O)NR$^9$R$^9$ or —C(=O)R$^{10}$;

$T_1$ is hydrogen, alkyl or aryl, wherein the alkyl or aryl may be optionally substituted with one or more R$^6$'s;

$T_2$ is hydrogen, alkyl or aryl, wherein the alkyl or aryl may be optionally substituted with one or more R$^6$'s;

$T_3$ is hydrogen, alkyl or aryl, wherein the alkyl or aryl may be optionally substituted with one or more R$^6$'s; and $T_4$ is hydrogen, alkyl or aryl, wherein the alkyl or aryl may be optionally substituted with one or more R$^6$'s.

In a ninth embodiment of the first aspect, the present invention provides a compound of Formula I, or an enantiomer, a diastereomer, or a pharmaceutically acceptable salt thereof, wherein:

Z is CH or N;

$R^1$ is aryl, arylalkyl or heteroaryl, any of which may be optionally substituted with one or more R$^6$'s;

$R^2$ is aryl, heteroaryl, heterocyclyl, —C(=O)R$^5$ or —C(=O)OR$^5$, wherein the aryl, heteroaryl and heterocyclyl may each be optionally substituted with one or more R$^6$'s;

$R^5$ is alkyl, aryl, cycloalkyl or heteroaryl, each of which may be optionally substituted with one or more R$^6$'s;

$R^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(=NR$^{14}$)NR$^9$R$^9$, —NHC(=NR$^{14}$)NR$^{14}$R$^{14}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

$R^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$^{8a}$, and the heteroaryl, heteroarylalkyl, heterocyclyl and heterocyclylalkyl each contain 1-4 heteroatoms selected from N, O and S;

$R^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$S(O$_2$)R$^{14}$, =O and arylalkyl;

$R^{10}$, at each occurrence, is independently selected from alkyl, cycloalkyl, aryl, arylalkyl, heteroaryl, heteroarylalkyl and heterocyclyl, wherein the cycloalkyl, aryl, arylalkyl, heteroaryl, heteroarylalkyl and heterocyclyl may each be optionally substituted with 0-3 R$^{10a}$, and the heteroaryl, heteroarylalkyl and heterocyclyl each contain 1-4 heteroatoms selected from N, O and S;

$R^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$S(O$_2$)R$^{14}$ and arylalkyl;

$R^{14}$, at each occurrence, is independently selected from hydrogen, alkyl, aryl, cycloalkyl and heteroaryl;

$R_{21}$ is hydrogen, alkyl, haloalkyl, hydroxyalkyl, aryl, cycloalkyl, halo, —CN, —C(=O)OH, —C(=O)OR$^{10}$, —OR$^{10}$, —C(=O)NR$^9$R$^9$ or —C(=O)R$^{10}$;

$T_1$ is hydrogen or alkyl, wherein the alkyl may be optionally substituted with one or more R$^6$'s;

$T_2$ is hydrogen or alkyl, wherein the alkyl may be optionally substituted with one or more R$^6$'s;

$T_3$ is hydrogen, alkyl or aryl, wherein the alkyl or aryl may be optionally substituted with one or more R$^6$'s; and $T_4$ is hydrogen or alkyl, wherein the alkyl may be optionally substituted with one or more R$^6$'s.

In a tenth embodiment of the first aspect, the present invention provides a compound of Formula I, or an enantiomer, a diastereomer, or a pharmaceutically acceptable salt thereof, wherein:

Z is CH or N;

$R^1$ is aryl, arylalkyl or heteroaryl, any of which may be optionally substituted with one or more R$^6$'s;

$R^2$ is aryl, heteroaryl, —C(=O)R$^5$ or —C(=O)OR$^5$, wherein the aryl and heteroaryl may each be optionally substituted with one or more R$^6$'s;

$R^5$ is alkyl, aryl or heteroaryl, each of which may be optionally substituted with one or more R$^6$'s;

$R^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

$R^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O)$_2$)R$^{14}$;

R$^9$, at each occurrence, is independently selected from hydrogen, alkyl, cycloalkyl, aryl, arylalkyl, heteroaryl, heteroarylalkyl and heterocyclyl, wherein the alkyl, cycloalkyl, aryl, arylalkyl, heteroaryl, heteroarylalkyl and heterocyclyl may each be optionally substituted with 0-5 R$^{8a}$, and the heteroaryl, heteroarylalkyl and heterocyclyl each contain 1-4 heteroatoms selected from N, O and S;

R$^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl, arylalkyl, heteroaryl and heterocyclyl, wherein the cycloalkyl, aryl, arylalkyl, heteroaryl and heterocyclyl may each be optionally substituted with 0-3 R$^{10a}$, and the heteroaryl and heterocyclyl each contain 1-4 heteroatoms selected from N, O and S;

R$^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl and heteroaryl;

R$_{21}$ is hydrogen, alkyl, haloalkyl, hydroxyalkyl, aryl, halo, —CN, —C(=O)OH, —C(=O)OR$^{10}$, —OR$^{10}$, —C(=O)NR$^9$R$^9$ or —C(=O)R$^{10}$;

T$_1$ and T$_2$ are hydrogen;

T$_3$ is hydrogen, alkyl or aryl, wherein the alkyl or aryl may be optionally substituted with one or more R$^6$'s; and T$_4$ is hydrogen, alkyl or aryl, wherein the alkyl or aryl may be optionally substituted with one or more R$^6$'s.

In an eleventh embodiment of the first aspect, the present invention provides a compound of Formula I, or an enantiomer, a diastereomer, or a pharmaceutically acceptable salt thereof, wherein:

Z is CH or N;

R$^1$ is aryl, arylalkyl or heteroaryl, any of which may be optionally substituted with one or more R$^6$'s;

R$^2$ is aryl, heteroaryl or —C(=O)OR$^5$, wherein the aryl and heteroaryl may each be optionally substituted with one or more R$^6$'s;

R$^5$ is alkyl, aryl or heteroaryl, each of which may be optionally substituted with one or more R$^6$'s;

R$^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

R$^9$, at each occurrence, is independently selected from hydrogen, alkyl, cycloalkyl, aryl, arylalkyl, heteroaryl and heterocyclyl, wherein the alkyl, cycloalkyl, aryl, arylalkyl, heteroaryl, and heterocyclyl may each be optionally substituted with 0-5 R$^{8a}$, and the heteroaryl and heterocyclyl each contain 1-4 heteroatoms selected from N, O and S;

R$^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl, heteroaryl and heterocyclyl, wherein the cycloalkyl, aryl, heteroaryl and heterocyclyl may each be optionally substituted with 0-3 R$^{10a}$, and the heteroaryl and heterocyclyl each contain 1-4 heteroatoms selected from N, O and S;

R$^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl and heteroaryl;

R$_{21}$ is hydrogen, alkyl, haloalkyl, hydroxyalkyl, aryl, halo, —CN, —C(=O)OR$^{10}$, —OR$^{10}$, —C(=O)NR$^9$R$^9$ or —C(=O)R$^{10}$;

T$_1$, T$_2$ and T$_4$ are hydrogen; and

T$_3$ is hydrogen, alkyl or aryl, wherein the alkyl or aryl may be optionally substituted with one or more R$^6$'s.

In a twelfth embodiment of the first aspect, the present invention provides a compound of Formula I, or an enantiomer, a diastereomer, or a pharmaceutically acceptable salt thereof, wherein:

Z is CH or N;

R$^1$ is aryl, arylalkyl or heteroaryl, any of which may be optionally substituted with one or more R$^6$'s;

$R^2$ is heteroaryl or —C(=O)OR$^5$, wherein the heteroaryl may be optionally substituted with one or more $R^6$'s;

$R^5$ is alkyl, aryl or heteroaryl, each of which may be optionally substituted with one or more $R^6$'s;

$R^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 $R^{9a}$;

$R^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, cycloalkyl, aryl, heteroaryl and heterocyclyl, wherein the alkyl, cycloalkyl, aryl, heteroaryl and heterocyclyl may each be optionally substituted with 0-5 $R^{8a}$, and the heteroaryl and heterocyclyl each contain 1-4 heteroatoms selected from N, O and S;

$R^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, cycloalkyl, aryl and heteroaryl, wherein the cycloalkyl, aryl and heteroaryl may each be optionally substituted with 0-3 $R^{10a}$, and the heteroaryl contains 1-4 heteroatoms selected from N, O and S;

$R^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl and heteroaryl;

$R_{21}$ is hydrogen, alkyl, haloalkyl, hydroxyalkyl, aryl, halo, —CN, —C(=O)OR$^{10}$, —C(=O)NR$^9$R$^9$ or —C(=O)R$^{10}$;

$T_1$, $T_2$ and $T_4$ are hydrogen; and $T_3$ is hydrogen or alkyl, wherein the alkyl may be optionally substituted with one or more $R^6$'s.

In a thirteenth embodiment of the first aspect, the present invention provides a compound of Formula I, or an enantiomer, a diastereomer, or a pharmaceutically acceptable salt thereof, wherein:

Z is CH or N;

$R^1$ is aryl or heteroaryl, any of which may be optionally substituted with one or more $R^6$'s;

$R^2$ is heteroaryl or —C(=O)OR$^5$, wherein the heteroaryl may be optionally substituted with one or more $R^6$'s;

$R^5$ is alkyl, aryl or heteroaryl, each of which may be optionally substituted with one or more $R^6$'s;

$R^6$, at each occurrence, is independently selected from alkyl, aryl, cycloalkyl, heteroaryl, heterocyclyl, halo, —NH$_2$, —CN, —NO$_2$, —C(=O)OH, —C(=O)OR$^{10}$, —OCF$_3$, —OCHF$_2$, —OR$^{10}$, —OH, —SH, —C(=O)NR$^9$R$^9$, —NR$^9$R$^9$, —S(O)$_2$NR$^9$R$^9$, —NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, heteroaryl, and heterocyclyl may each be optionally substituted with 0-5 $R^{9a}$;

$R^{8a}$, at each occurrence, is independently selected from alkyl, haloalkyl, aryl, arylalkyl, cycloalkyl, heteroaryl, heterocyclyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, cycloalkyl, aryl and heteroaryl, wherein the alkyl, cycloalkyl, aryl and heteroaryl, may each be optionally substituted with 0-5 $R^{8a}$, and the heteroaryl contains 1-4 heteroatoms selected from N, O and S;

$R^{9a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, cycloalkyl, aryl and heteroaryl, wherein the cycloalkyl, aryl and heteroaryl may each be optionally substituted with 0-3 $R^{10a}$, and the heteroaryl contains 1-4 heteroatoms selected from N, O and S;

$R^{10a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl and heteroaryl;

$R_{21}$ is hydrogen, alkyl, haloalkyl, hydroxyalkyl, aryl, halo, —CN, —C(=O)OR$^{10}$ or —C(=O)NR$^9$R$^9$;

$T_1$, $T_2$ and $T_4$ are hydrogen; and $T_3$ is hydrogen or alkyl.

In a fourteenth embodiment of the first aspect, the present invention provides a compound of Formula I, or an enantiomer, a diastereomer, or a pharmaceutically acceptable salt thereof, wherein:

Z is CH or N;

$R^1$ is a 5- or 6-membered aryl, a 5- or 6-membered arylalkyl or a 5- to 10-membered heteroaryl, any of which may be optionally substituted with one or more $R^6$'s;

$R^2$ is a 5- to 10-membered heteroaryl or —C(=O)OR$^5$, wherein the heteroaryl may be optionally substituted with one or more $R^6$'s;

$R^5$ is alkyl or aryl, each of which may be optionally substituted with one or more $R^{6'}$s;

$R^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 $R^{9a}$;

$R^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, cycloalkyl, aryl, heteroaryl and heterocyclyl, wherein the alkyl, cycloalkyl, aryl, heteroaryl and heterocyclyl may each be optionally substituted with 0-5 $R^{8a}$, and the heteroaryl and heterocyclyl each contain 1-4 heteroatoms selected from N, O and S;

$R^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, cycloalkyl, aryl and heteroaryl, wherein the cycloalkyl, aryl and heteroaryl may each be optionally substituted with 0-3 $R^{10a}$, and the heteroaryl contains 1-4 heteroatoms selected from N, O and S;

$R^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl and heteroaryl;

$R_{21}$ is hydrogen, alkyl, haloalkyl, hydroxyalkyl, aryl, halo, —CN, —C(=O)OR$^{10}$, —C(=O)NR$^9$R$^9$ or —C(=O)R$^{10}$;

$T_1$, $T_2$ and $T_4$ are hydrogen; and $T_3$ is hydrogen or alkyl.

In a fifteenth embodiment of the first aspect, the present invention provides a compound of Formula I, or an enantiomer, a diastereomer, or a pharmaceutically acceptable salt thereof, wherein:

Z is CH or N;

$R^1$ is a 5- or 6-membered aryl, a 5- or 6-membered arylalkyl or a 5- to 10-membered heteroaryl, any of which may be optionally substituted with one or more $R^{6'}$s;

$R^2$ is a 5- to 6-membered heteroaryl or —C(=O)OR$^5$, wherein the heteroaryl may be optionally substituted with one or more $R^{6'}$s;

$R^5$ is alkyl, which may be optionally substituted with one or more $R^{6'}$s;

$R^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 $R^{9a}$;

$R^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, cycloalkyl, aryl, heteroaryl and heterocyclyl, wherein the alkyl, cycloalkyl, aryl, heteroaryl and heterocyclyl may each be optionally substituted with 0-5 $R^{8a}$, and the heteroaryl and heterocyclyl each contain 1-4 heteroatoms selected from N, O and S;

$R^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, cycloalkyl, aryl and heteroaryl, wherein the cycloalkyl, aryl and heteroaryl may each be optionally substituted with 0-3 $R^{10a}$, and the heteroaryl contains 1-4 heteroatoms selected from N, O and S;

$R^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl and heteroaryl;

$R_{21}$ is hydrogen, alkyl, haloalkyl, hydroxyalkyl, aryl, halo, —CN, —C(=O)OR$^{10}$ or —C(=O)NR$^9$R$^9$;

$T_1$, $T_2$ and $T_4$ are hydrogen; and $T_3$ is hydrogen or alkyl.

In a sixteenth embodiment of the first aspect, the present invention provides a compound of Formula I, or an enantiomer, a diastereomer, or a pharmaceutically acceptable salt thereof, wherein:

Z is CH or N;

$R^1$ is phenyl, benzyl, benzooxazolyl, piperidinyl or pyrimidinyl, any of which may be optionally substituted with one or more $R^6$'s;

$R^2$ is piperidinyl, pyrimidinyl or —C(=O)OR$^5$, wherein the piperidinyl and pyrimidinyl may be optionally substituted with one or more $R^6$'s;

$R^5$ is alkyl;

$R^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —C(=O)NR$^9$R$^9$, —NR$^9$R$^9$, —S(O)$_2$NR$^9$R$^9$, —NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 $R^{9a}$;

$R^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, cycloalkyl, aryl, heteroaryl and heterocyclyl, wherein the alkyl, cycloalkyl, aryl, heteroaryl, and heterocyclyl may each be optionally substituted with 0-5 $R^{8a}$, and the heteroaryl and heterocyclyl each contain 1-4 heteroatoms selected from N, O and S;

$R^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, cycloalkyl, aryl and heteroaryl, wherein the cycloalkyl, aryl and heteroaryl may each be optionally substituted with 0-3 $R^{10a}$, and the heteroaryl contains 1-4 heteroatoms selected from N, O and S;

$R^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl and heteroaryl;

$R_{21}$ is hydrogen, alkyl, haloalkyl, hydroxyalkyl, aryl, halo, —CN, —C(=O)OR$^{10}$ or —C(=O)NR$^9$R$^9$;

$T_1$, $T_2$ and $T_4$ are hydrogen; and $T_3$ is hydrogen or alkyl.

In a seventeenth embodiment of the first aspect, the present invention provides a compound of Formula I, or an enantiomer, a diastereomer, or a pharmaceutically acceptable salt thereof, wherein the compound is selected from one of the examples.

For each of the embodiments described in this application, further and more particular values of the terms used in each of the embodiments may be selected from the following definitions; these values may be used individually in any of the embodiments or in any combination. It is noted that for any occurrences of "=O", these may be used with suitable accommodation in the bond structure at that site as will be appreciated by those skilled in the art.

The heteroaryl, heteroarylalkyl, heterocyclyl and heterocyclylalkyl used in each occurrence may each contain 1-4 heteroatoms selected from N, O and S.

For each of the embodiments described in this application, further and more particular values of the terms used in each of the embodiments may be selected from the following definitions; these values may be used individually in any of the embodiments or in any combination. It is noted that for any occurrences of "=O", these may be used with suitable accommodation in the bond structure at that site as will be appreciated by those skilled in the art.

The heteroaryl, heteroarylalkyl, heterocyclyl and heterocyclylalkyl used in each occurrence may each contain 1-4 heteroatoms selected from N, O and S.

In a second aspect, the present invention provides a compound, or an enantiomer, a diastereomer, or a pharmaceutically acceptable salt thereof, selected from the group consisting of the compounds exemplified in the examples.

In a third aspect, the present invention relates to pharmaceutical compositions comprised of a therapeutically effective amount of a compound of the present invention, alone or, optionally, in combination with a pharmaceutically acceptable carrier and/or one or more other agent(s), for example, a glucagon-like peptide-1 receptor agonist or fragment thereof.

In one embodiment of the third aspect, the present invention provides a pharmaceutical composition comprised of a therapeutically effective amount of a compound of Formula I, II(y), or II(z) as defined above, alone or, optionally, in combination with a pharmaceutically acceptable carrier and/or one or more other agent(s), for example, a glucagon-like peptide-1 receptor agonist or fragment thereof.

In another embodiment of the third aspect, the present invention provides a pharmaceutical composition comprised of a therapeutically effective amount of a compound selected from the group of compounds exemplified in the Examples, alone or, optionally, in combination with a pharmaceutically acceptable carrier and/or one or more other agent(s), for example, a glucagon-like peptide-1 receptor agonist or fragment thereof.

In a fourth aspect, the present invention relates to methods of modulating the activity of the GPR119 G protein-coupled receptor comprising administering to a mammalian patient, for example, a human patient, in need thereof a therapeutically effective amount of a compound of the present invention, alone, or optionally, in combination with another compound of the present invention and/or at least one other type of therapeutic agent.

In one embodiment of the fourth aspect, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In another embodiment of the fourth aspect, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In another embodiment of the fourth aspect, the present invention relates to a method for preventing, modulating, or treating the progression or onset of diabetes, comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In another embodiment of the fourth aspect, the present invention relates to a method for preventing, modulating, or treating the progression or onset of hyperglycemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In another embodiment of the fourth aspect, the present invention relates to a method for preventing, modulating, or treating the progression or onset of obesity comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In another embodiment of the fourth aspect, the present invention relates to a method for preventing, modulating, or treating the progression or onset of dyslipidemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In another embodiment of the fourth aspect, the present invention relates to a method for preventing, modulating, or treating the progression or onset of hypertension comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In another embodiment of the fourth aspect, the present invention relates to a formulated product wherein the selected formulation is made by combining (a) a compound of Formula I (using any of the compound embodiments listed above) and (b) a dipeptidyl peptidase-IV (DPP4) inhibitor (for example, a member selected from saxagliptin, sitagliptin, vildagliptin and alogliptin).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Young, S. D. et al., *Antimicrobial Agents and Chemotherapy*, 2602-2605 (1995).

To the extent that compounds of Formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R^4$) occurs more than one time in any constituent or formula for a compound, its definition at each occurrence is independent of its definition at every other occurrence. Thus, for example, if a group is shown to be substituted with $(R^4)_m$ and m is 0-3, then said group may optionally be substituted with up to three $R^4$ groups and $R^4$ at each occurrence is selected independently from the definition of R[4]. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

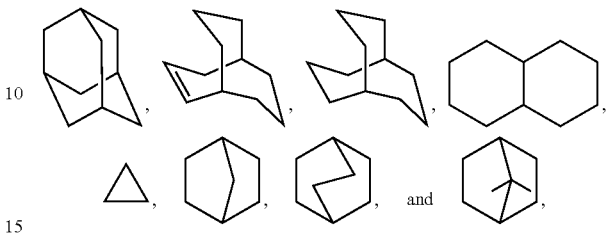

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example,

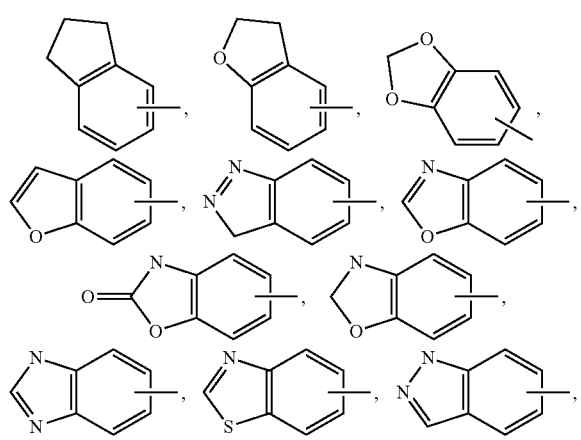

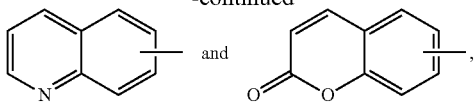

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, pyrrolidonyl, 4-piperidonyl, chromanyl, decahydroquinolinyl, dihydrofuro[2,3-b]tetrahydrofuran, indolinyl, isochromanyl, isoindolinyloctahydroisoquinolinyl, piperazinyl, piperidinyl, piperidonyl, 4-piperidonyl, tetrahydrofuranyl, tetrahydroisoquinolinyl, tetrahydroquinolinyl, morpholinyl, dihydrofuranyl, tetrahydrothiophenyl, pyranyl, dihydropyranyl, 1,4-dioxanyl and 1,3-dioxanyl. Also included are fused ring and spiro compounds containing, for example, the above heterocycles.

As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro-[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinolinyl, 4H-quinolizinyl, quinoxalinyl, quinuclidinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Any compound that can be converted in vivo to provide the bioactive agent (i.e., a compound of Formula I) is a prodrug within the scope and spirit of the invention.

The term "prodrugs" as employed herein includes esters and carbonates formed by reacting one or more hydroxyls of compounds of Formula I with alkyl, alkoxy or aryl substituted acylating agents employing procedures known to those skilled in the art to generate acetates, pivalates, methylcarbonates, benzoates, and the like.

Various forms of prodrugs are well known in the art and are described in:
a) Wermuth, C. G. et al., *The Practice of Medicinal Chemistry*, Chapter 31, Academic Press (1996);
b) *Design of Prodrugs*, H. Bundgaard, ed., Elsevier (1985);
c) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and
d) Testa, B. et al., *Hydrolysis in Drug and Prodrug Metabolism*, Wiley-VCH (2003).

Said references are incorporated herein by reference, particularly as to the description of prodrugs.

In addition, compounds of Formula I are, subsequent to their preparation, preferably isolated and purified to obtain a composition containing an amount by weight equal to or greater than 99% of a compound of Formula I ("substantially pure" compound), which is then used or formulated as described herein. Such "substantially pure" compounds of Formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of Formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{18}$F, $^{15}$O, and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the relevant subject matter referenced in the citation.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

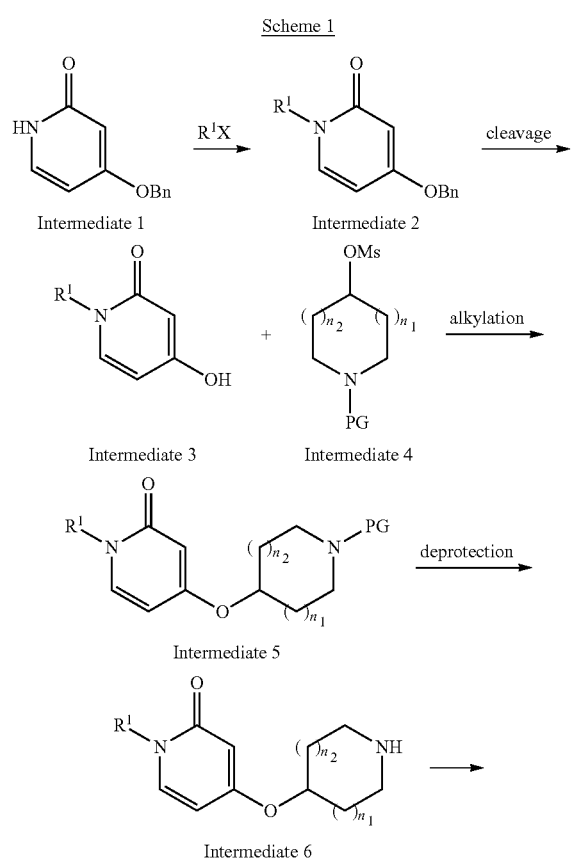

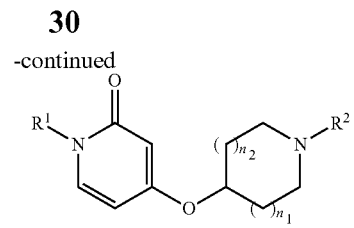

Compounds of Formula I may be prepared by procedures depicted in Scheme 1. Intermediate 1, obtained from commercial sources, can be reacted with $R^1X$ (where $R^1$ other than H is as defined with respect to Formula I, and X is a halide) in the presence of a ligand such as 8-hydroxyquinoline, CuI and a base such as $K_2CO_3$ in a suitable solvent, such as DMF, DMSO, etc., at an elevated temperature to yield intermediate 2. Cleavage of the benzyl group of intermediate 2 can be performed using the methods known in the art such as hydrogenolysis catalyzed by palladium. Intermediate 3 can then be alkylated with intermediate 4, which can be prepared by reaction of the corresponding alcohols with methanesulfonyl chloride, in the presence of a base such as $K_2CO_3$ at an elevated temperature. The above alcohols are commercially available or can be prepared by various methods known to one skilled in the art, for example, those found in Sandler, S. et al., *Organic Functional Group Preparations*, Vol. I, Academic Press, Inc. (1983). Removal of the protecting group ("PG") of intermediate 5 can be carried out with appropriate reagents known to those skilled in the art (for specific details, see Greene, T. W. et al., *Protecting Groups in Organic Synthesis*, John Wiley & Sons Inc. (1991)). The deprotected product can then be treated with $R^2X$ (where $R^2$ is defined as in Formula I, and X is a leaving group such as halide, mesylate, triflate, etc.), which are commercially available or can be prepared by various methods known in the art, at the conditions that are routine for those skilled in the art of organic synthesis to afford compounds of Formula I. Alternatively, the intermediate 6 can also be reacted with isocyanates or isothiocyanates in the presence of a base, such as $Et_3N$, to provide the compounds of Formula I.

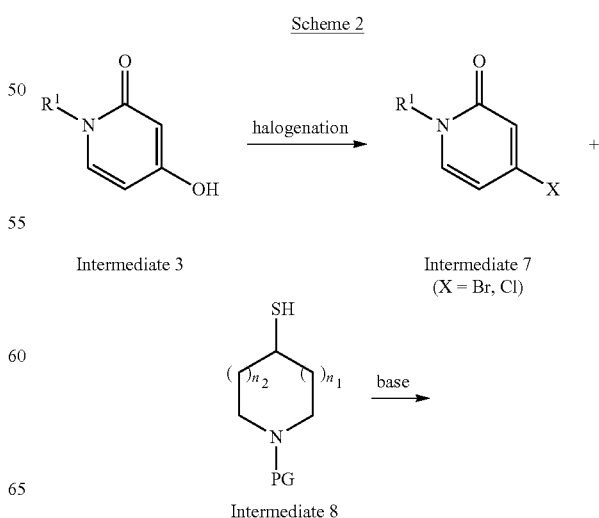

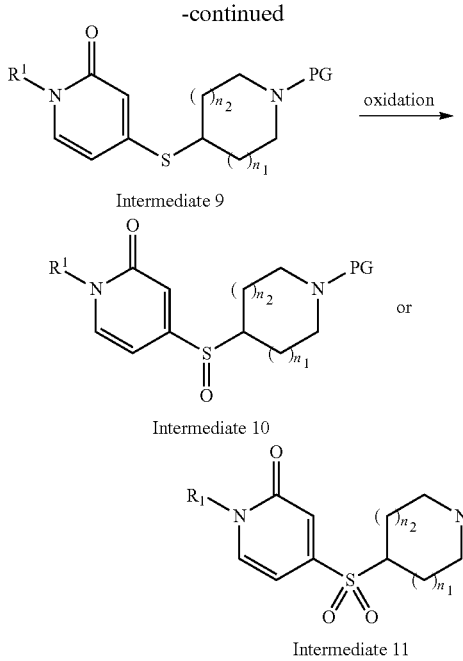

Intermediate 9

Intermediate 10

Intermediate 11

Compounds of Formula I, wherein Y is defined as —S—, —S(=O)— or —S(O)$_2$—, may be prepared by procedures outlined in Scheme 2. Halogenation of intermediate 3 generated as described in Scheme 1 can be achieved with POBr$_3$, PBr$_3$ or POCl$_3$ using the conditions known to one skilled in the art. The halogenated pyridone can then be reacted with intermediate 8, which can be prepared according to the procedures described in U.S. Pat. No. 6,556,384 B1 (Owen, D. et al.), which is incorporated by reference herein as to these preparations, in the presence of a base such as NaH to yield intermediate 9. Oxidation of intermediate 9 with an oxidant such as mCPBA in a suitable solvent such as CH$_2$Cl$_2$ affords intermediate 10 and intermediate 11. Intermediate 9, intermediate 10 or intermediate 11 can be carried forward to compounds of Formula I following the procedures described above in Scheme 1 by substituting intermediate 9, 10 or 11 for intermediate 5.

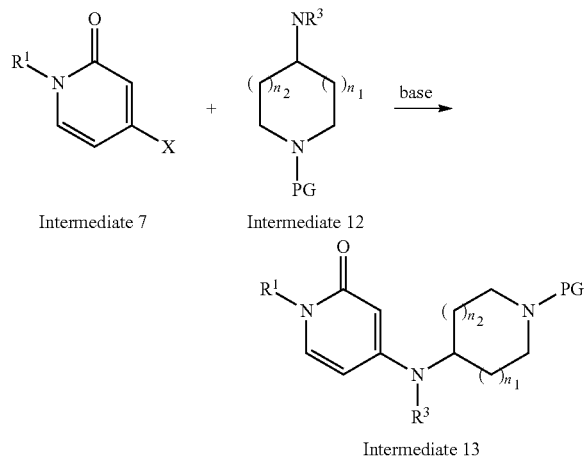

Scheme 3

Intermediate 7    Intermediate 12

Intermediate 13

Compounds of Formula I, wherein Y is defined as NR$^3$, may be prepared by procedures illustrated in Scheme 3. Intermediate 7 prepared as described in Scheme 3 can be reacted with intermediate 12, which are commercially available or can be prepared by the methods known to one skilled in the art, in the presence of a catalyst such as Pd(P(tBu)$_3$)$_2$ and a base such as NaO$^t$Bu in a suitable solvent such as toluene to yield intermediate 13. The products can then be further elaborated to compounds of Formula I using the procedures described above in Scheme 1 by substituting intermediate 13 for intermediate 5.

Alternatively, compounds of Formula I, wherein Y is defined as —N(R$^3$)—, may also be prepared by the procedures similar to those provided in Scheme 3. Those invention compounds can be alternatively obtained by treatment of the compounds of Formula I, wherein R$^3$=H, with a suitable electrophile R$^3$X (where X is a halide, mesylate, triflate, etc.) in the presence of a base such as K$_2$CO$_3$, CsCO$_3$, NaO$^t$Bu, etc.

Scheme 4

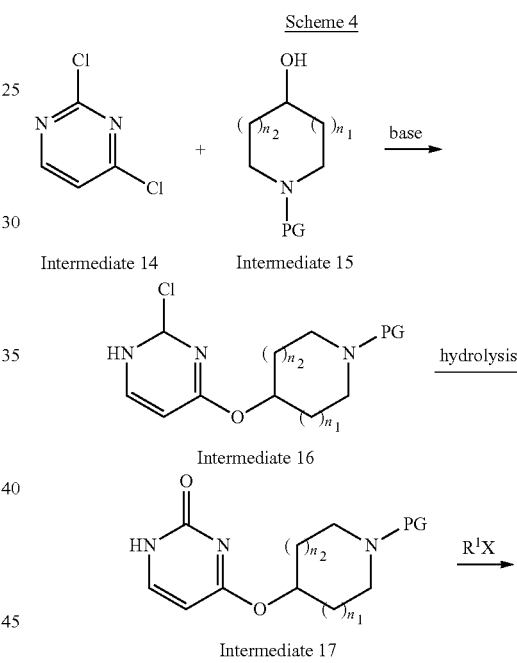

Intermediate 14    Intermediate 15

Intermediate 16

Intermediate 17

Intermediate 18

Alternatively, compounds of Formula I can be synthesized by procedures outlined in Scheme 4. Intermediate 14, obtained from commercial sources, can be reacted with intermediate 15, which are commercially available or can be generated by many methods readily recognized by one skilled in the art, for example, those found in Sandler, S. et al., *Organic Functional Group Preparations*, Vol. I, Academic Press, Inc. (1983), in the presence of a base such as NaH to yield intermediate 16. Hydrolysis of intermediate 16 can be achieved by treatment with DABCO in the presence of a base such as K$_2$CO$_3$ in dioxane/water at an elevated temperature. Intermediate 17 can then be reacted with R$^1$X (where R$^1$ is defined with respect to Formula I, and X is a halide) in the presence of a ligand such as 8-hydroxyquinoline, CuI and a base such as $K_2CO_3$ in a suitable solvent, such as DMF, DMSO, etc., at an elevated temperature to yield intermediate 18. The intermediate 18 can be carried forward to compounds of Formula I following the procedures described above in Scheme 1 by substituting intermediate 18 for intermediate 5.

Scheme 5

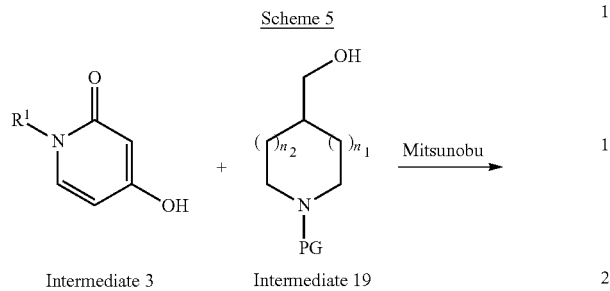

Intermediate 3          Intermediate 19

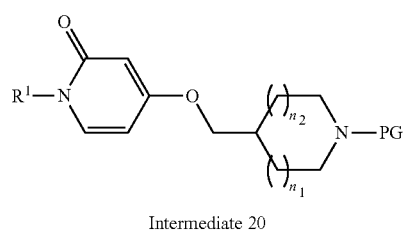

Intermediate 20

Compounds of Formula I may be prepared by procedures illustrated in Scheme 5. Intermediate 3 generated as described in Scheme I can be reacted with intermediate 19, which are commercially available or can be made by various methods readily recognized by one skilled in the art, for example, those found in Sandler, S. et al., *Organic Functional Group Preparations*, Vol. I, Academic Press, Inc. (1983), via Mitsunobo reaction to yield intermediate 20, which can be converted to Formula I using the procedures described above in Scheme 1 by substituting intermediate 20 for intermediate 5.

Scheme 6

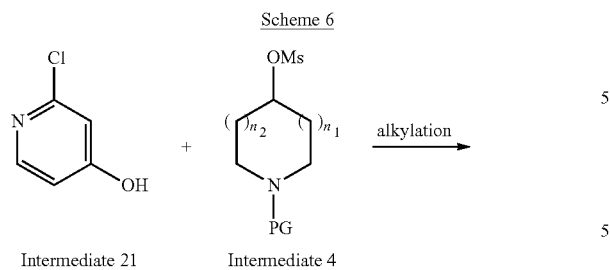

Intermediate 21          Intermediate 4

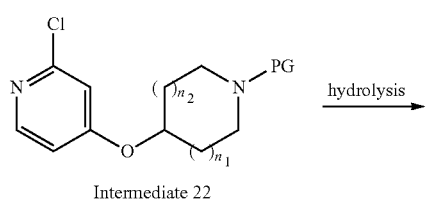

Intermediate 22

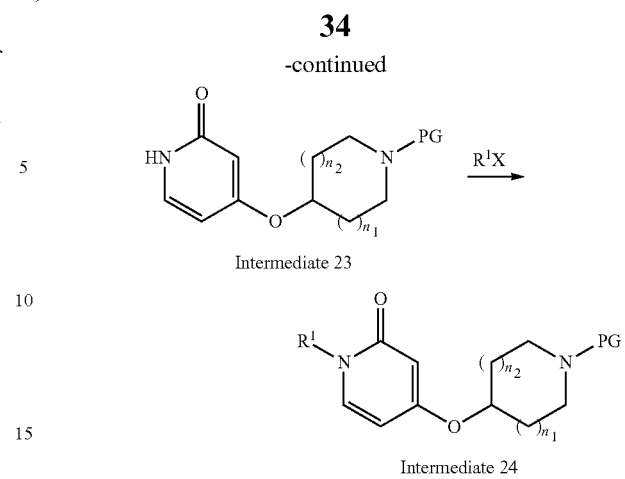

Intermediate 23

Intermediate 24

Alternatively, compounds of Formula I may be synthesized as provided in Scheme 6. Intermediate 21, obtained from commercial sources, can be reacted with intermediate 4 prepared as described in Scheme 1 to give intermediate 22. Hydrolysis of intermediate 22 can be achieved by treatment with DABCO in the presence of a base such as $K_2CO_3$ in dioxane/water at an elevated temperature. Intermediate 23 can be treated with $R^1X$ (where $R^1$ is defined with respect to Formula I and X is a halide) in the presence of a ligand such as 8-hydroxyquinoline, CuI and a base such as $K_2CO_3$ in a suitable solvent, such as DMF, DMSO, etc., at an elevated temperature to yield intermediate 24. The intermediate 24 can be carried forward to compounds of Formula I following the procedures described above in Scheme 1 by substituting intermediate 24 for intermediate 5.

Scheme 7

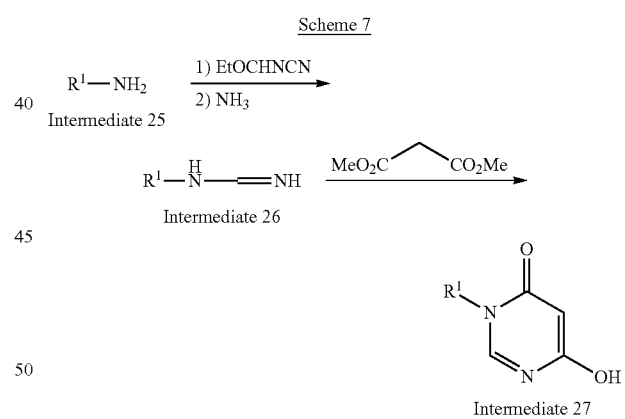

Intermediate 27

Compounds of Formula I can also be prepared by procedures illustrated in Scheme 7. Intermediate 25 ($R^1$—$NH_2$, where $R^1$ is as defined in Formula I), which are commercially available or can be made by methods recognized by one skilled in the art, can be converted to formamidine intermediate 26 in a two step procedure described by Donetti, A. et al., *J. Med. Chem.*, 27:380 (1984). Intermediate 26 can be reacted with dimethyl malonate to yield intermediate 27 using literature procedures (*J. Med. Chem.*, 45:3639 (2002)). The intermediate 27 can then be carried forward to compounds of Formula I following the procedures described above in Scheme 1 by substituting intermediate 28 for intermediate 3.

Scheme 8

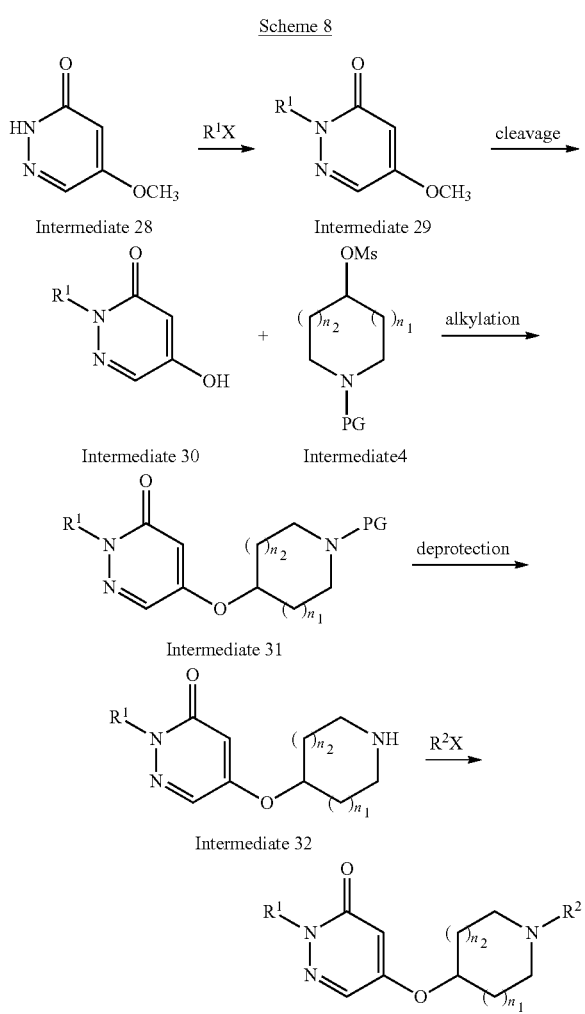

Compounds of Formula I, wherein R²¹ is defined as H and Y as —O—, may be prepared by procedures depicted in Scheme 8. Intermediate 28, obtained from commercial sources, can be reacted with R¹X (where R¹ other than H is as defined with respect to Formula I, and X is a halide) in the presence of a ligand such as 8-hydroxyquinoline, CuI and a base such as $K_2CO_3$ in a suitable solvent, such as DMF, DMSO, etc., at an elevated temperature to yield intermediate 29 (alternatively, it can be reacted with R¹X (where R¹ other than H is as defined with respect to Formula I, and X is a halide) in the presence of a base such as NaH in a suitable solvent, such as DMF, DMSO, etc., at an elevated temperature). Cleavage of the methoxy group of intermediate 29 can be performed using the methods known in the art, such as hydrolysis by NaOH. Intermediate 30 can then be alkylated with intermediate 4, which can be prepared by reaction of the corresponding alcohols with methanesulfonyl chloride, in the presence of a base such as $K_2CO_3$ at an elevated temperature. The above alcohols are commercially available or can be prepared by various methods known to one skilled in the art (typical examples may be found in Sandler, S. et al., *Organic Functional Group Preparations*, Vol. I, Academic Press, Inc. (1983)). Removal of the protecting group of intermediate 31 can be carried out with appropriate reagents well known to those skilled in the art (for specific details, see Greene, T. W. et al., *Protecting Groups in Organic Synthesis*, John Wiley & Sons Inc. (1991)). The deprotected product can then be treated with R²X (where R² is defined as in Formula I, and X is a leaving group such as halide, mesylate, triflate, etc.), which are commercially available or can be prepared by many methods known in the art, under various conditions that are routine for those skilled in the art of organic synthesis to afford compounds of Formula I. Alternatively, the intermediate 32 can also be reacted with isocyanates or isothiocyanates in the presence of a base such as $Et_3N$ to provide other compounds of Formula I.

Scheme 9

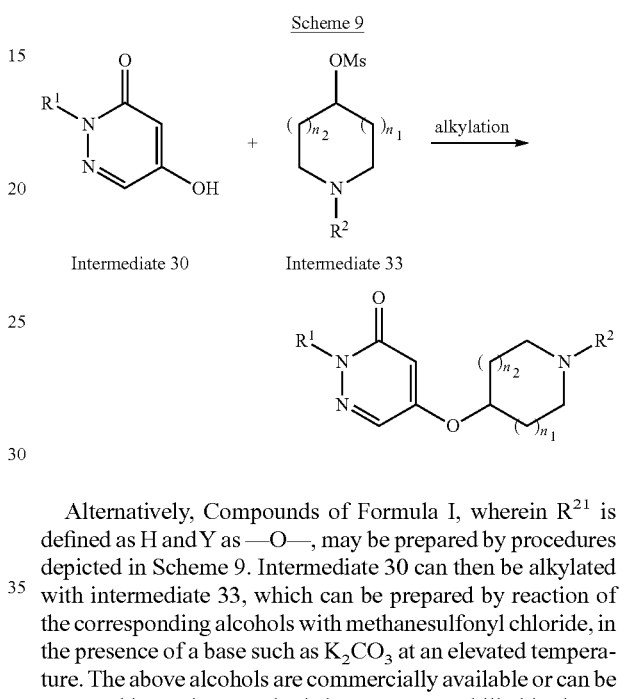

Alternatively, Compounds of Formula I, wherein R²¹ is defined as H and Y as —O—, may be prepared by procedures depicted in Scheme 9. Intermediate 30 can then be alkylated with intermediate 33, which can be prepared by reaction of the corresponding alcohols with methanesulfonyl chloride, in the presence of a base such as $K_2CO_3$ at an elevated temperature. The above alcohols are commercially available or can be prepared by various methods known to one skilled in the art (typical examples may be found in Sandler, S. et al., *Organic Functional Group Preparations*, Vol. I, Academic Press, Inc. (1983)) to afford compounds of Formula I.

Scheme 10

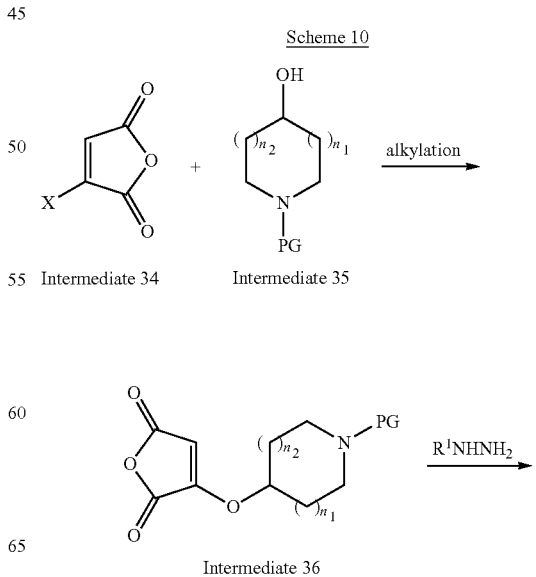

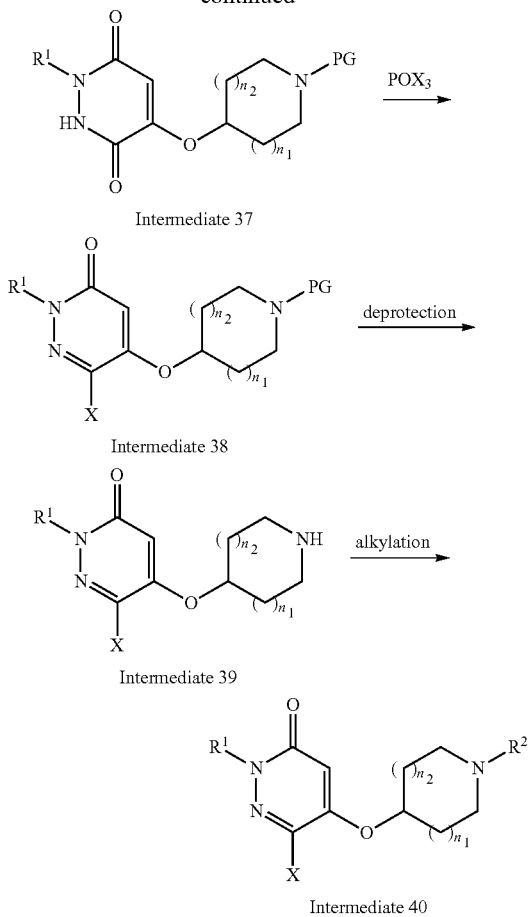

Alternatively, compounds of Formula I, wherein $R^{21}$ is defined as halogen and Y as —O—, may be prepared by procedures illustrated in Scheme 10. Intermediate 34, obtained from commercial sources, can be reacted with intermediate 35, which are also commercially available or can be made by various methods readily recognized by one skilled in the art (typical examples may be found in Sandler, S. et al., *Organic Functional Group Preparations*, Vol. I, Academic Press, Inc. (1983)) in the presence of a base such as NaH in a suitable solvent, such as DMF, DMSO, etc., at an elevated temperature to yield intermediate 36. Condensation of the intermediate 36 with $R^1NHNH_2$ (where $R^1$ other than H is as defined with respect to Formula I) to afford intermediate 37. Treatment of intermediate 37 with $POX_3$ at an elevated temperature to yield intermediate 38. Removal of the protecting group of intermediate 39 can be carried out with appropriate reagents known to those skilled in the art (for specific details, see Greene, T. W. et al., *Protecting Groups in Organic Synthesis*, John Wiley & Sons Inc. (1991)). The deprotected product can then be treated with alkylating agent $R^2Z$ (where $R^2$ is defined as in Formula I, and Z is a leaving group such as halide, mesylate, triflate, etc.), which are commercially available or can be prepared by various methods known in the art, at various conditions that are routine for those skilled in the art of organic synthesis to afford compounds of Formula I. Alternatively the intermediate 39 can also be reacted with isocyanates or isothiocyanates in the presence of a base such as $Et_3N$ to provide the compounds of Formula I.

Alternatively, compounds of Formula I, wherein Y is defined as —O— and $R^{21}$ as CN, amines, alkoxys, alkyls, aryls, alkenes, or alkynes, may be prepared by procedures depicted in Scheme 11. Intermediate 40a can then be coupled with commercially available CuCN, amines, alcohols, boronic acids by various methods known in the art, at various conditions that are routine for those skilled in the art of organic synthesis to afford compounds of Formula I.

Scheme 11

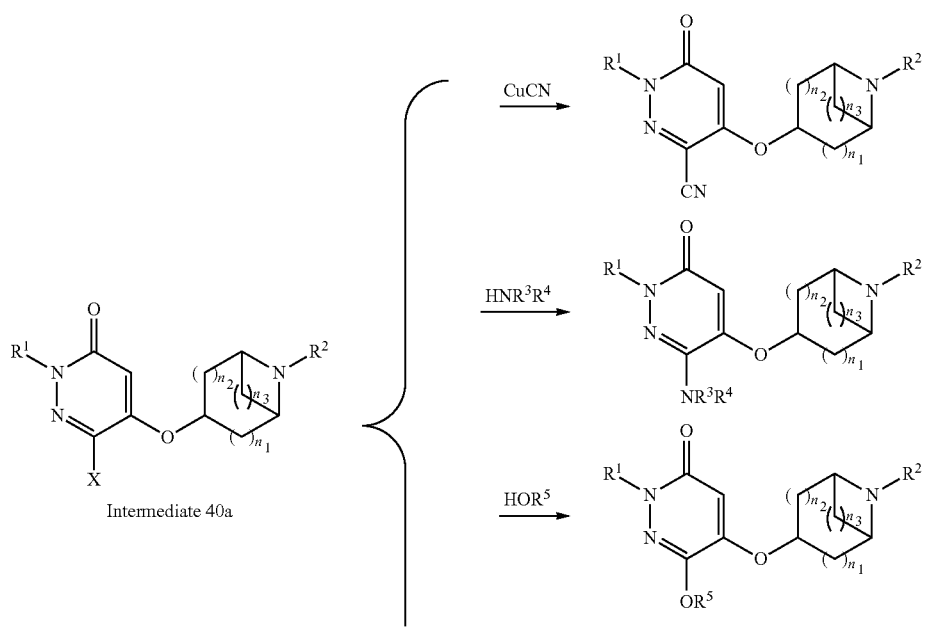

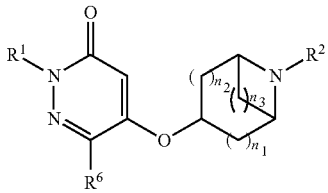

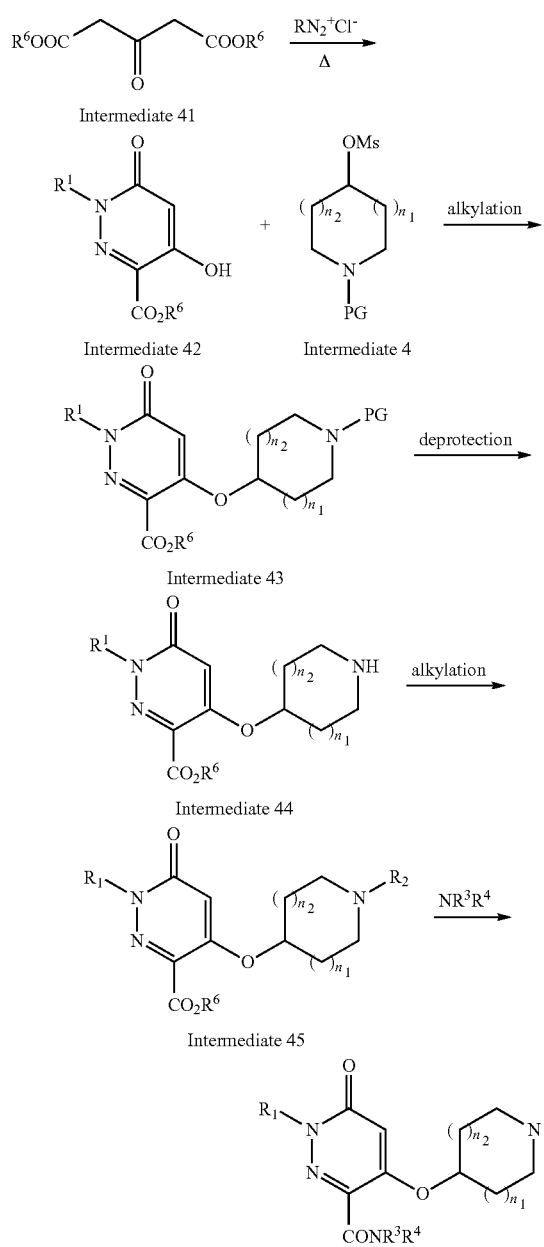

mediate 42 (typical examples may be found in Schober, B. D., *J. Heterocyclic Chem.*, 26:169 (1989)). Intermediate 42 can then be alkylated with intermediate 4, which can be prepared by reaction of the corresponding alcohols with methanesulfonyl chloride, in the presence of a base such as $K_2CO_3$ at an elevated temperature. The above alcohols are commercially available or can be prepared by various methods known to one skilled in the art (typical examples may be found in Sandler, S. et al., *Organic Functional Group Preparations*, Vol. I, Academic Press, Inc. (1983)). Removal of the protecting group of intermediate 43 can be carried out with appropriate reagents well known to those skilled in the art (for specific details, see Greene, T. W. et al., *Protecting Groups in Organic Synthesis*, John Wiley & Sons Inc. (1991)). The deprotected product Intermediate 44 can then be treated with $R^2X$ (where $R^2$ is defined as in Formula I, and X is a leaving group such as halide, mesylate, triflate, etc.), which are commercially available or can be prepared by various methods known in the art, under various conditions that are routine for those skilled in the art of organic synthesis to afford compounds of Formula I as intermediate 45. Alternatively the intermediate 44 can also be reacted with isocyanates or isothiocyanates in the presence of a base such as $Et_3N$ to provide the compounds of Formula I as intermediate 45. Further elaboration of intermediate 45 with commercially available amines at an elevated temperature can afford alternative compounds of Formula I.

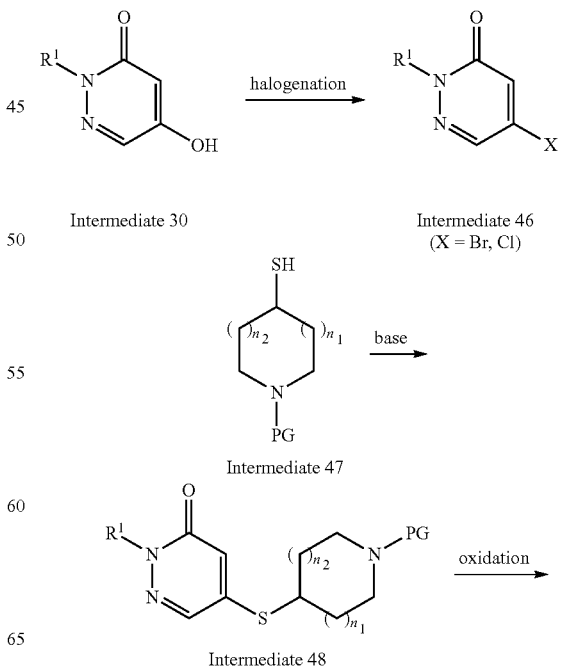

Alternatively, compounds of Formula I, wherein Y is defined as —O— and $R^{21}$ as esters and amides, may be prepared by procedures illustrated in Scheme 12. Intermediate 41, obtained from commercial sources, can be reacted with aryldiazonium chloride, which are also commercially available, and followed by thermal ring closure to yield inter-

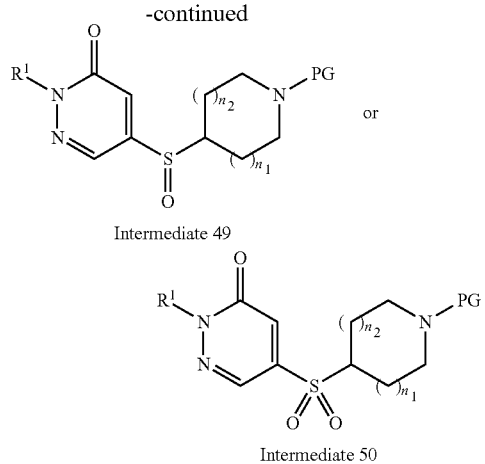

Intermediate 49

Intermediate 50

Compounds of Formula I, wherein Y is defined as —S—, —S(=O)— or —S(O)$_2$—, may be prepared by procedures outlined in Scheme 13. Halogenation of intermediate 30, generated as described in Scheme 10, can be achieved with POBr$_3$, PBr$_3$ or POCl$_3$ using the conditions known to one skilled in the art. The halogenated intermediate 46 can then be reacted with intermediate 47, which can be prepared according to the procedures described in U.S. Pat. No. 6,556,384 B1 (Owen, D. et al.), in the presence of a base such as NaH to yield intermediate 48. Oxidation of intermediate 48 with an oxidant such as mCPBA in a suitable solvent such as CH$_2$Cl$_2$ affords intermediate 49 and intermediate 50. Intermediate 48, intermediate 49 or intermediate 50 can be carried forward to compounds of Formula I following the procedures described above in Scheme 8 by substituting intermediate 48, 49 or 50 for intermediate 31.

Scheme 14

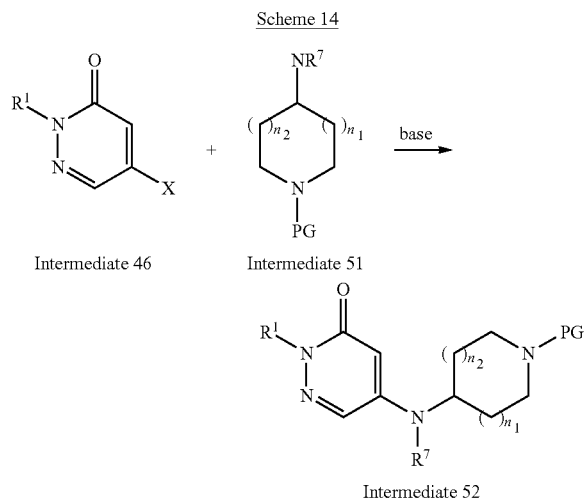

Intermediate 46    Intermediate 51

Intermediate 52

Compounds of Formula I, wherein Y is defined as —N(R$^7$)—, may be prepared by procedures illustrated in Scheme 14. Intermediate 46 prepared as described in Scheme 13 can be reacted with intermediate 51, which are commercially available or can be prepared by the methods known to one skilled in the art, in the presence of a catalyst such as Pd(P(tBu)$_3$)$_2$ and a base such as NaO$^t$Bu in a suitable solvent such as toluene to yield intermediate 52. The products can then be further elaborated to compounds of Formula I using the procedures described above in Scheme 8 by substituting intermediate 52 for intermediate 31.

Alternatively, compounds of Formula I, wherein Y is defined as —N(R$^7$)—, may also be prepared by treatment of the compounds of Formula I, wherein R$^7$=H, with a suitable electrophile R$^7$X (where X is a halide, mesylate, triflate, etc.) in the presence of a base such as K$_2$CO$_3$, CsCO$_3$, NaOtBu, etc.

ABBREVIATIONS

The following abbreviations are employed in the Examples and elsewhere herein:

EtOAc=ethyl acetate
DMF=dimethylformamide
THF=tetrahydrofuran
K$_2$CO$_3$=potassium carbonate
Na$_2$CO$_3$=sodium carbonate
MgSO$_4$=magnesium sulfate
SiO$_2$=silicon dioxide
CH$_2$Cl$_2$=methylene chloride
MeOH=methanol
HCl=hydrochloric acid
Cs$_2$CO$_3$=cesium carbonate
KOH=potassium hydroxide
DME=1,2-dimethoxyethane
Pd(dppf)Cl$_2$=[1,1'-bis(diphenylphosphino)ferrocene]dichloropalladium (II)
t-BuONa=sodium tert-butoxide
Pd$_2$(dba)$_3$=tris(dibenzylideneacetone)dipalladium (0)
TFA=trifluoroacetic acid
BINAP=rac-2,2'-bis(diphenylphosphino)-1,1'-binaphthyl
DABCO=1,4-diazabicyclo[2.2.2]octane
mCPBA=m-chloroperoxybenzoic acid
min=minute(s)
h or hr=hour(s)
mL or ml=milliliter
g=gram(s)
mg=milligram(s)
mmol=millimole(s)
LRMS=low resolution mass spectrometry
NMR=nuclear magnetic resonance

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using the same.

Example 1 trans-tert-Butyl 2-methyl-4-(1-(4-(methylsulfonyl)phenyl)-2-oxo-1,2-dihydropyridin-4-yloxy)piperidine-1-carboxylate

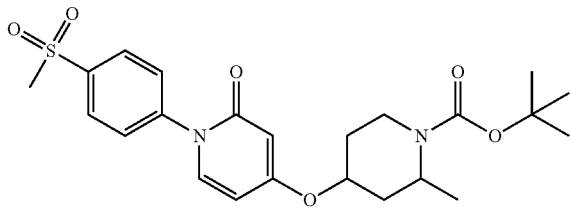 [SMILES: CC1CC(Oc2ccn(-c3ccc(S(C)(=O)=O)cc3)c(=O)c2)CCN1C(=O)OC(C)(C)C]

Step A. Preparation of tert-butyl 4-hydroxy-2-methylpiperidine-1-carboxylate To a solution of tert-butyl 2-methyl-4-oxopiperidine-1-carboxylate (727 mg, 3.41 mmol, Small Molecules Inc.) in MeOH (6.0 mL) at 0° C. was added sodium borohydride (193 mg, 5.11 mmol, Aldrich) in several portions. The reaction mixture was stirred at 0° C. for 1 hr and warmed up to room temperature and continuously stirred for another 2.5 hrs. The resulting mixture was then quenched with saturated $NH_4Cl$ aqueous solution and evaporated under reduced pressure to remove MeOH followed by extraction with $CH_2Cl_2$ (3×). The combined extracts were dried ($Na_2SO_4$) and concentrated in vacuo to give the title compound (745 mg) as a colorless sticky oil which was used without further purification.

Step B. Preparation of tert-butyl 2-methyl-4-(methylsulfonyloxy)piperidine-1-carboxylate To a mixture of tert-butyl 4-hydroxy-2-methylpiperidine-1-carboxylate (745 mg, 3.46 mmol) and triethylamine (0.965 mL, 6.92 mmol, EMD) in $CH_2Cl_2$ (20.0 mL) at 0° C. was added methanesulfonyl chloride (0.324 mL, 4.15 mmol, Aldrich) dropwise. The reaction mixture was stirred at 0° C. for 5 min and at room temperature for 3 hrs and then quenched with 0.5N HCl solution. The mixture was separated and aqueous layer was extracted further with $CH_2Cl_2$ (2×). The combined organic layers were washed with brine, dried ($Na_2SO_4$) and evaporated under reduced pressure. The residue was purified by flash chromatography on silica gel (0-100% EtOAc in hexane) to give both cis and trans isomers of tert-butyl 4-hydroxy-2-methylpiperidine-1-carboxylate(cis-isomer, 498.1 mg, off-white solid, 49%; trans-isomer, 146.4 mg, colorless oil, 14%). The structures were assigned based on 1D-NOE of NMR.

Step C. Preparation of 4-(benzyloxy)-1-(4-(methylsulfonyl)phenyl)pyridine-2(1H)-one A mixture of 4-benzyloxy-2(1H)-pyridone (6.87 g, 34.1 mmol, Aldrich), 4-bromophenyl methyl sulphone (8.01 g, 34.1 mmol, Combi-Blocks Inc.), copper(I) iodide (1.30 g, 6.82 mmol, Aldrich), 8-hydroxyquinoline (0.99 g, 6.82 mmol, Alfa Aesar) and potassium carbonate (6.12 g, 44.3 mmol, EMD) in DMSO (100 mL) was heated at 145° C. for 6 h, cooled to room temperature and then diluted with 10% $NH_4OH$ aqueous solution (50 mL) and EtOAc (100 mL). The resulting mixture was filtered and the solid was washed with $H_2O$ and EtOAc to give 8.0 g crude product as a greenish solid. MS (ESI) 356 (M+H).

Step D. Preparation of 4-hydroxy-1-(4-(methylsulfonyl)phenyl)pyridine-2(1H)-one A stirring suspension of 4-(benzyloxy)-1-(4-(methylsulfonyl)phenyl)-pyridine-2(1H)-one (3.0 g, 8.44 mmol) and palladium on activated carbon (1.63 g, 10 wt. %, wet, Aldrich) in THF (150 mL) and methanol (250 mL) was under hydrogen (balloon) for 1 hr. The resulting mixture was purged with nitrogen and then diluted with THF (150 mL) and methanol (50 mL). After stirring under nitrogen for 30 min, the mixture was filtered through a pad of CELITE® 545 filter aid and the filtrate was evaporated under reduced pressure to give 2.28 g crude product as a dark greenish solid. MS (ESI) 266 (M+H).

Step E. Example 1

A mixture of 4-hydroxy-1-(4-(methylsulfonyl)phenyl)pyridine-2(1H)-one (173 mg, 0.652 mmol), cis-tert-butyl 2-methyl-4-(methylsulfonyloxy)piperidine-1-carboxylate (191 mg, 0.652 mmol) and potassium carbonate (180 mg, 1.304 mmol) in DMF (3.0 mL) was heated at 140° C. for 6 hrs and 100° C. overnight. To the above mixture additional potassium carbonate (90 mg, 1 equiv.) was added and the reaction was heated at 120° C. for 3 hrs and then cooled to room temperature. The mixture was diluted with EtOAc and water and the aqueous layer was extracted further with EtOAc (4×). The combined organic layers were washed with brine/water (1:1, 2×), dried ($Na_2SO_4$) and evaporated under reduced pressure. The residue was purified by flash chromatography on silica gel (0-100% EtOAc/hexane) to yield trans-isomer of tert-butyl 2-methyl-4-(1-(4-(methylsulfonyl)phenyl)-2-oxo-1,2-dihydropyridin-4-yloxy)piperidine-1-carboxylate (31.4 mg, 10.4%) as an off-white solid. $^1$H NMR (500 MHz, $CDCl_3$). δ 8.07 (d, J=8.25 Hz, 2H), 7.61 (d, J=8.25 Hz, 2H), 7.22 (d, J=7.70 Hz, 1H), 6.02 (dd, J=7.70, 2.20 Hz, 1H), 5.97 (d, J=2.20 Hz, 1H), 4.50-4.66 (m, 2H), 4.09-4.13 (m, 1H), 3.09 (s, 3H), 2.91-3.05 (m, 1H), 2.10-2.22 (m, 1H), 1.96-2.07 (m, 1H), 1.69-1.85 (m, 1H), 1.51-1.64 (m, 1H), 1.48 (s, 9H), 1.23 (d, J=7.15 Hz, 3H). MS (ESI) 463 (M+H).

Example 2 cis-tert-Butyl 2-methyl-4-(1-(4-(methylsulfonyl)phenyl)-2-oxo-1,2-dihydropyridin-4-yloxy)piperidine-1-carboxylate

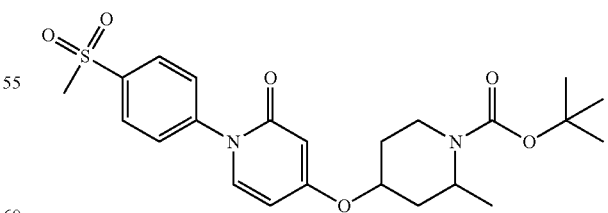

A mixture of 4-hydroxy-1-(4-(methylsulfonyl)phenyl)pyridin-2(1H)-one (125 mg, 0.471 mmol), trans-tert-butyl 2-methyl-4-(methylsulfonyloxy)piperidine-1-carboxylate (138.2 mg, 0.471 mmol, Example 1) and potassium carbonate (163 mg, 1.178 mmol) in DMF (4.0 mL) was heated at 110° C. for 20 hrs. The reaction mixture was cooled to room temperature and diluted with EtOAc and water. The aqueous layer was extracted further with EtOAc (3×). The combined organic layers were washed with brine/water (1:1, 2×), dried (Na₂SO₄) and evaporated under reduced pressure. The residue was purified by flash chromatography on silica gel (0-100% EtOAc in hexane) to yield cis isomer of tert-butyl 2-methyl-4-(1-(4-(methylsulfonyl)phenyl)-2-oxo-1,2-dihydropyridin-4-yloxy)piperidine-1-carboxylate (114.6 mg, 52% yield) as an off-white solid. ¹H NMR (500 MHz, CDCl₃). δ 8.07 (d, J=8.80 Hz, 2H), 7.62 (d, J=8.25 Hz, 2H), 7.24 (d, J=7.70 Hz, 1H), 6.06 (dd, J=7.70, 2.75 Hz, 1H), 5.95 (d, J=2.20 Hz, 1H), 4.64-4.70 (m, 1H), 4.35-4.45 (m, 1H), 3.91-3.98 (m, 1H), 3.18-3.28 (m, 1H), 3.09 (s, 9H), 1.95-2.04 (m, 2H), 1.89-1.96 (m, 1H), 1.75-1.84 (m, 1H), 1.48 (s, 9H), 1.27 (d, J=7.15 Hz, 3H). MS (ESI) 463 (M+H).

Example 3 cis-4-(2-Methyl-1-(5-propylpyrimidin-2-yl)piperidin-4-yloxy)-1-(4-(methylsulfonyl)phenyl)pyridin-2 (1H)-one, TFA salt

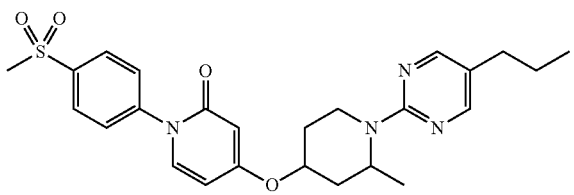 [SMILES: CCCc1cnc(N2CCC(Oc3ccn(-c4ccc(S(C)(=O)=O)cc4)c(=O)c3)CC2C)nc1]

Step A. Preparation of cis-4-(2-methylpiperidin-4-yloxy)-1-(4-(methylsulfonyl)-phenyl)pyridine-2 (1H)-one hydrochloric acid salt To a solution of cis-tert-butyl 2-methyl-4-(1-(4-(methylsulfonyl)phenyl)-2-oxo-1,2-dihydropyridin-4-yloxy)piperidine-1-carboxylate (98.9 mg, 0.214 mmol) in MeOH (1.0 mL) at 0° C. was added hydrochloric acid (2.0 mL, 8.00 mmol, 4.0 M in dioxane, Aldrich). The reaction mixture was warmed up to room temperature and continuously stirred at room temperature. After stirring for 1.5 hrs, the mixture was evaporated under reduced pressure to give the title compound (114.5 mg) as an off-white solid. This material was used in the next step without further purification. MS (ESI) 363 (M+H).

Step B. Example 3

A mixture of cis-4-(2-methylpiperidin-4-yloxy)-1-(4-(methylsulfonyl)-phenyl)pyridin-2(1H)-one hydrochloric acid salt (45 mg, 0.124 mmol), 2-chloro-5-propylpyrimidine (38.9 mg, 0.248 mmol, Wako) and cesium carbonate (162 mg, 0.497 mmol, Aldrich) in DMF (0.8 mL) was heated under microwave conditions (180° C., 2 hrs). The resulting mixture was diluted with EtOAc and water. The aqueous layer was extracted further with EtOAc (3×). The combined extracts were washed with brine, dried (Na₂SO₄) and evaporated under reduced pressure. The residue was purified by preparative HPLC (C₁⁸ column; 0-100% methanol in water containing 0.05% trifluoroacetic acid) to yield Example 3 (12.7 mg, off-white solid, 20%) upon lyophilization. ¹H NMR (500 MHz, CDCl₃). δ 8.40 (s, 2H), 8.09 (d, J=8.80 Hz, 2H), 7.63 (d, J=8.80 Hz, 2H), 7.30 (d, J=7.70 Hz, 1H), 6.15 (dd, J=7.70, 2.20 Hz, 1H), 6.12 (d, J=2.75 Hz, 1H), 4.99-5.07 (m, 1H), 4.79 (app brs, 1H), 4.51-4.58 (m, 1H), 3.51-3.63 (m, 1H), 3.11 (s, 3H), 2.50 (t, J=7.70 Hz, 2H), 2.21 (t, J=14.57 Hz, 2H), 1.91-2.13 (m, 2H), 1.56-1.71 (m, 2H), 1.42 (d, J=7.15 Hz, 3H), 0.98 (t, J=7.15 Hz, 3H). MS (ESI) 483 (M+H).

Example 4 trans-4-(2-Methyl-1-(5-propylpyrimidin-2-yl)piperidin-4-yloxy)-1-(4-(methylsulfonyl)phenyl)pyridin-2 (1H)-one, TFA salt

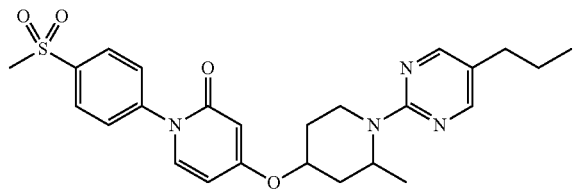 [SMILES: CCCc1cnc(N2CCC(Oc3ccn(-c4ccc(S(C)(=O)=O)cc4)c(=O)c3)CC2C)nc1]

Example 4 was prepared according to procedures described in Example 3 substituting trans-tert-butyl 2-methyl-4-(1-(4-(methylsulfonyl)phenyl)-2-oxo-1,2-dihydropyridin-4-yloxy)piperidine-1-carboxylate for cis-tert-butyl 2-methyl-4-(1-(4-(methylsulfonyl)phenyl)-2-oxo-1,2-dihydropyridin-4-yloxy)piperidine-1-carboxylate in Step A. ¹H NMR (500 MHz, CDCl₃). δ 8.33 (s, 2H), 8.08 (d, J=8.25 Hz, 2H), 7.62 (d, J=8.80 Hz, 2H), 7.21-7.29 (m, 1H), 6.17 (d, J=2.75 Hz, 1H), 6.09 (dd, J=7.70, 2.75 Hz, 1H), 5.11-5.27 (m, 1H), 4.69-4.82 (m, 2H), 3.16-3.32 (m, 1H), 3.03-3.15 (m, 3H), 2.48 (t, J=7.42 Hz, 2H), 2.31-2.38 (m, 1H), 2.17-2.20 (m, 1H), 1.81-1.96 (m, 1H), 1.67-1.80 (m, 1H), 1.53-1.69 (m, 2H), 1.35 (d, J=7.15 Hz, 3H), 0.97 (t, J=7.42 Hz, 3H). MS (ESI) 483 (M+H).

Example 5

1-(2-Methylbenzo[d]oxazol-5-yl)-4-(1-(5-propylpyrimidin-2-yl)piperidin-4-yloxy)pyridin-2(1H)-one

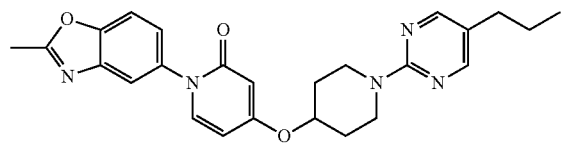 [SMILES: CCCc1cnc(N2CCC(Oc3ccn(-c4ccc5oc(C)nc5c4)c(=O)c3)CC2)nc1]

Step A. Preparation of 1-(5-propylpyrimidin-2-yl)piperidin-4-ol

To a stirring solution of piperidin-4-ol (2.33 g, 23.0 mmol, Aldrich) and potassium carbonate (6.36 g, 46.0 mmol, EMD) in DMF (15 mL) at room temperature was added 2-chloro-5-propylpyrimidine (4.33 g, 27.6 mmol, Wako). The reaction mixture was heated at 100° C. for 3 h then diluted with H₂O. The resulting mixture was extracted with EtOAc (2×). The organic layers were combined, dried over Na₂SO₄ and concentrated in vacuo to a brown oil. The oil was purified by flash chromatography (SiO₂, 0 to 100% EtOAc in CH₂Cl₂) to yield 5.01 g of desired product as a white solid. MS (ESI) 222 (M+H).

Step B. Preparation of 1-(5-propylpyrimidin-2-yl) piperidin-4-ylmethanesulfonate To a stirring solution of 1-(5-propylpyrimidin-2-yl)piperidin-4-ol (9.2 g, 41.6 mmol), Et₃N (12.85 mL, 91 mmol, Aldrich) in CH₂Cl₂ (80 mL) at 0° C. was added a solution of Methanesulfonyl chloride (3.54 mL, 45.7 mmol, ACROS®) in CH₂Cl₂ (20 mL) dropwise. The reaction mixture was stirred at room temperature for 1 h and washed with 1N HCl in H₂O, saturated NaHCO₃ in H₂O and brine. The organic layer was dried over Na₂SO₄ and concentrated in vacuo to yield 11.7 g of the desired product as an off-white solid. MS (ESI) 300 (M+H).

Step C. Preparation of 4-(1-(5-propylpyrimidin-2-yl) piperidin-4-yloxy)pyridine-2(1H)-one A stirring suspension of 4-hydroxypyridin-2(1H)-one (5.23 g, 47.1 mmol, Aldrich), 1-(5-propylpyrimidin-2-yl)piperidin-4-ylmethanesulfonate (11.7 g, 39.2 mmol), potassium carbonate (12.5 g, 90.0 mmol, EMD) and DMSO (48 mL) was heated at 100° C. for 3 hours and then cooled to room temperature. The resulting mixture was diluted with H₂O and extracted with EtOAc (2×). The organic layers were combined and concentrated in vacuo to a brown solid. The solid was purified by flash chromatography (SiO₂, 100% EtOAc and then SiO₂, 10% MeOH in CH₂Cl₂) to yield 5.00 g of desired product as an off-white solid. MS (ESI) 315 (M+H).

Step D. Example 5

A mixture of 5-bromo-2-methylbenzo[d]oxazole (81 mg, 0.38 mmol), 4-(1-(5-propylpyrimidin-2-yl)piperidin-4-yloxy)pyridin-2(1H)-one (80 mg, 0.25 mmol), quinolin-8-ol (11 mg, 0.076 mmol, Alfa Aesar), potassium carbonate (46 mg, 0.33 mmol), Copper(I) iodide (15 mg, 0.076 mmol, Alfa Aesar) in DMSO (2 mL) was heated under microwave condition 160° C. for 30 min. The resulting mixture was diluted with H₂O and extracted with EtOAc (2×). The combined organic layers were concentrated in vacuo to a green oil. The oil was purified by flash chromatography (SiO₂, 0 to 5% MeOH in CH₂Cl₂) to yield 37 mg of desired product as a light brown solid. ¹H NMR (400 MHz, DMSO-d₆) δ ppm 8.30 (s, 2H) 7.81 (d, J=8.53 Hz, 1H) 7.74 (d, J=2.01 Hz, 1H) 7.66 (d, J=7.53 Hz, 1H) 7.39 (dd, J=8.78, 2.01 Hz, 1H) 6.05-6.17 (m, 2H) 4.74-4.89 (m, 1H) 4.22-4.34 (m, 2H) 3.49-3.61 (m, 2H) 2.71 (s, 3H) 2.44 (t, J=7.53 Hz, 2H) 2.00-2.16 (m, 2H) 1.50-1.75 (m, 4H) 0.94 (t, J=7.28 Hz, 3H). MS (ESI) 446 (M+H).

Example 6

1-(2-Isopropylbenzo[d]oxazol-5-yl)-4-(1-(5-propylpyrimidin-2-yl)piperidin-4-yloxy)pyridin-2(1H)-one

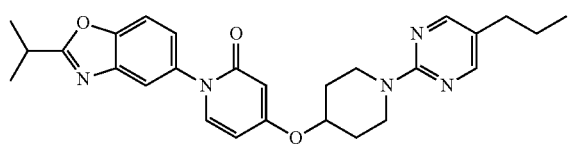 [SMILES: CCCc1cnc(N2CCC(Oc3ccn(-c4ccc5oc(C(C)C)nc5c4)c(=O)c3)CC2)nc1]

Example 6 was prepared according to procedures described in Example 5 substituting 5-bromo-2-isopropylbenzo[d]oxazole for 5-bromo-2-methylbenzo-[d]oxazole in Step D. ¹H NMR (400 MHz, CDCl₃) δ ppm 8.18 (s, 2H), 7.64 (d, J=2.20 Hz, 1H), 7.57 (d, J=8.25 Hz, 1H), 7.32 (dd, J=8.52, 1.92 Hz, 1H), 7.23-7.26 (m, 1H), 5.98-6.07 (m, 2H), 4.53-4.64 (m, 1H), 4.16-4.29 (m, 2H), 3.57-3.70 (m, 2H), 3.19-3.37 (m, 1H), 2.42 (t, J=7.42 Hz, 2H), 2.03-2.17 (m, 2H), 1.78-1.93 (m, 2H), 1.53-1.65 (m, 2H), 1.47 (d, J=7.15 Hz, 6H), 0.95 (t, J=7.42 Hz, 3H). MS (ESI) 474 (M+H).

Example 7

1-(2-Methylbenzo[d]oxazol-6-yl)-4-(1-(5-propylpyrimidin-2-yl)piperidin-4-yloxy)pyridin-2(1H)-one, hydrochloride salt

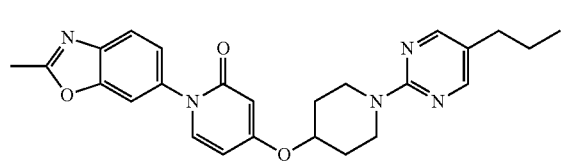 [SMILES: CCCc1cnc(N2CCC(Oc3ccn(-c4ccc5nc(C)oc5c4)c(=O)c3)CC2)nc1]

Example 7 was prepared according to procedures described in Example 5 substituting 6-bromo-2-methylbenzo[d]oxazole for 5-bromo-2-methylbenzo-[d]oxazole in Step D except that the product was dissolved in CH₂Cl₂ and 1 equivalent of HCl (1N HCl in Et₂O) was added, the resulting mixture stirred for 5 min and then concentrated in vacuo to give Example 3. ¹H NMR (400 MHz, DMSO-d₆) δ ppm 8.29 (s, 2H) 7.77 (d, J=1.76 Hz, 1H) 7.73 (d, J=8.28 Hz, 1H) 7.61 (d, J=7.53 Hz, 1H) 7.31 (dd, J=8.53, 2.01 Hz, 1H) 5.98-6.16 (m, 2H) 4.71-4.84 (m, 1H) 4.10-4.28 (m, 2H) 3.44-3.59 (m, 2H) 2.65 (s, 3H) 2.40 (t, J=7.53 Hz, 2H) 2.00-2.10 (m, 2H) 1.57-1.72 (m, 2H) 1.46-1.57 (m, 2H) 0.88 (t, J=7.40 Hz, 3H). MS (ESI) 446 (M+H).

Example 8 tert-Butyl 4-(1-(4-(methylsulfonyl)phenyl)-6-oxo-1, 6-dihydropyridazin-4-yloxy)piperidine-1-carboxylate

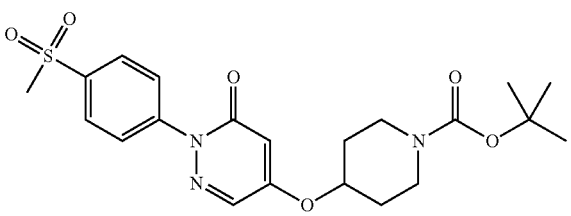 [SMILES: CC(C)(C)OC(=O)N1CCC(Oc2cnn(-c3ccc(S(C)(=O)=O)cc3)c(=O)c2)CC1]

Step A. Preparation of 5-methoxy-2-(4-(methylsulfonyl)phenyl)pyridazin-3(2H)-one To a mixture of 5-methoxypyridazin-3(2H)-one (631 mg, 5.00 mmol) in DMF (5 mL) at room temperature under argon was added NaH (240 mg, 6.0 mmol) in three portions over 2 minutes. After stirring the reaction mixture at room temperature for 30 minutes, 1-fluoro-4-(methylsulfonyl)benzene (1.045 g, 6.0 mmol) was added. The resulting reaction mixture was heated at 100° C. under argon for 5 hour. After cooling the reaction mixture to room temperature, 3 mL of 1 M NaOH solution was added. The resulting reaction mixture was heated at 60° C. for 3 hours. After cooling the reaction to room temperature, 10 mL of Et$_2$O along with 20 mL of water were added. The organic layer was separated and discarded. The aq. phase was acidified with 1N HCl to pH=5. Solid precipitates were collected by filtration and further washed with water (5 mL×2) and Methanol (3 mL×2) to yield 231 mg of product as tan solid. The filtrate was extracted with EtOAc (10 mL×3). The combined organic phases were washed with brine (20 mL), dried (MgSO$_4$), filtered and concentrated. The crude product was purified by flash chromatography (60 to 100% EtOAc/Hexanes) to yield 371 mg of additional product. A total 602 mg (45%) of desired product was obtained. $^1$H NMR (400 MHz, DMSO) δ ppm 3.26 (s, 3H), 6.10 (d, J=2.64 Hz, 1H), 7.82 (d, J=8.79 Hz, 2H), 7.89 (d, J=2.64 Hz, 1H), 8.01 (d, J=8.79 Hz, 2H), 11.85 (s, 1H). MS (ESI) 267 (M+H).

Step B. Preparation of tert-butyl 4-(methylsulfonyloxy)piperidine-1-carboxylate

To a stirring solution of tert-butyl-4-hydroxy-1-piperidinecarboxylate (10.28 g, 51.08 mmol, Aldrich) and Et$_3$N (14.25 mL, 102.16 mmol, EMD) in CH$_2$Cl$_2$ (300 mL) at room temperature was added methanesulfonyl chloride (4.35 mL, 56.19 mmol, Aldrich) dropwise. The reaction mixture was stirred at room temperature for 4 h and washed with 0.1N HCl aqueous solution, H$_2$O and brine. The organic layer was dried with Na$_2$SO$_4$ and concentrate in vacuo to yield 14.3 g of the crude product as a light orange solid.

Step C. Example 8

To a mixture of 5-hydroxy-2-(4-(methylsulfonyl)phenyl) pyridazin-3(2H)-one (26.6 mg, 0.10 mmol) in DMF (1 mL) at room temperature under argon was added potassium carbonate (41.4 mg, 0.30 mmol, EMD) and tert-butyl 4-(methylsulfonyloxy)piperidine-1-carboxylate (53.3 mg, 0.15 mmol). The reaction mixture was heated at 90° C. overnight and then cooled to room temperature. The resulting mixture was diluted with EtOAc (10 mL) and H$_2$O (10 mL) and the aqueous layer was extracted further with EtOAc (5 mL×2). The combined extracts were washed with brine (10 mL×3), dried (Na$_2$SO$_4$) and evaporated. The residual was purified by flash chromatography (0 to 10% MeOH/CH$_2$Cl$_2$) to yield 38.9 mg (87%) of Example 8 as a white solid. $^1$H NMR (400 MHz, CDCl$_3$). δ 1.39-1.51 (m, 9H), 1.68-1.86 (m, 2H), 1.91-2.07 (m, 2H), 3.06 (s, 3H), 3.21-3.42 (m, 2H), 3.64-3.82 (m, 2H), 4.35-4.58 (m, 1H), 6.21 (d, J=2.64 Hz, 1H), 7.72 (d, J=2.64 Hz, 1H), 7.88 (d, J=8.79 Hz, 2H), 8.03 (d, J=8.79 Hz, 2H). MS (ESI) 394 (M+H-tBu).

Example 9

2-(4-(Methylsulfonyl)phenyl)-5-(1-(5-propylpyrimidin-2-yl)piperidin-4-yloxy)pyridazin-3(2H)-one

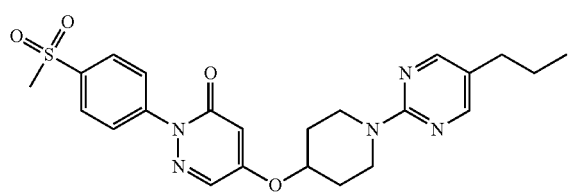 [SMILES: CCCc1cnc(N2CCC(Oc3cnn(-c4ccc(S(C)(=O)=O)cc4)c(=O)c3)CC2)nc1]

Example 9 was prepared in 60% yield according to procedures described in Example 8 substituting 1-(5-propylpyrimidin-2-yl)piperidin-4-ylmethanesulfonate for tert-butyl 4-(methylsulfonyloxy)piperidine-1-carboxylate. $^1$H NMR (400 MHz, CDCl$_3$). δ 0.93 (t, J=7.47 Hz, 3H), 1.44-1.71 (m, 2H), 1.72-1.97 (m, 2H), 1.97-2.18 (m, 2H), 2.40 (t, J=7.47 Hz, 2H), 3.07 (s, 3H), 3.43-3.78 (m, 2H), 4.00-4.36 (m, 2H), 4.44-4.74 (m, 1H), 6.26 (d, J=2.64 Hz, 1H), 7.74 (d, J=2.64 Hz, 1H), 7.89 (d, J=8.35 Hz, 2H), 8.03 (d, J=8.79 Hz, 2H), 8.17 (s, 2H). MS (ESI) 470 (M+H).

Example 10

5-(1-(5-Cyclopropylpyrimidin-2-yl)piperidin-4-yloxy)-2-(4-(methylsulfonyl)phenyl)pyridazin-3(2H)-one

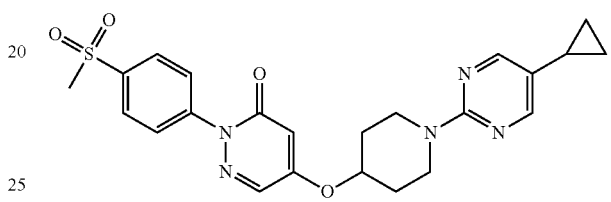

Example 10 was prepared in 45% yield according to procedures described in Example 8 substituting 1-(5-cyclopropylpyrimidin-2-yl)piperidin-4-yl methanesulfonate for tert-butyl 4-(methylsulfonyloxy)piperidine-1-carboxylate. $^1$H NMR (400 MHz, CDCl$_3$). δ 0.59 (d, J=6.15 Hz, 2H), 0.79-1.00 (m, 2H), 1.65-1.77 (m, 1H), 1.77-1.94 (m, 2H), 1.99-2.20 (m, 2H), 3.07 (s, 3H), 3.45-3.72 (m, 2H), 4.08-4.28 (m, 2H), 4.56 (s, 1H), 6.25 (d, J=3.08 Hz, 1H), 7.73 (d, J=3.08 Hz, 1H), 7.89 (d, J=8.79 Hz, 2H), 8.03 (d, J=8.79 Hz, 2H), 8.13 (s, 2H). MS (ESI) 468 (M+H).

Example 11

5-(1-(5-Acetylpyrimidin-2-yl)piperidin-4-yloxy)-2-(4-(methylsulfonyl)phenyl)pyridazin-3(2H)-one

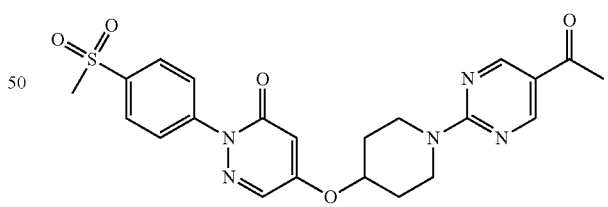

Example 11 was prepared in 45% yield according to procedures described in Example 8 substituting 1-(5-acetylpyrimidin-2-yl)piperidin-4-ylmethanesulfonate for tert-butyl 4-(methylsulfonyloxy)piperidine-1-carboxylate. $^1$H NMR (400 MHz, CDCl$_3$) δ ppm 1.80-1.99 (m, 2H), 2.01-2.21 (m, 2H), 2.41-2.59 (m, 3H), 3.07 (s, 3H), 3.80-4.03 (m, 2H), 4.10-4.36 (m, 2H), 4.50-4.76 (m, 1H), 7.75 (d, J=3.08 Hz, 1H), 7.89 (d, J=8.79 Hz, 2H), 8.03 (d, J=8.79 Hz, 2H), 8.85 (s, 2H). MS (ESI) 470 (M+H).

Example 12

5-(1-(5-Ethylpyrimidin-2-yl)piperidin-4-yloxy)-2-(4-(methylsulfonyl)phenyl)pyridazin-3(2H)-one

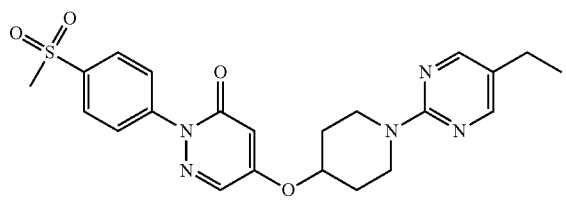 [SMILES: CCc1cnc(N2CCC(Oc3cnn(-c4ccc(S(C)(=O)=O)cc4)c(=O)c3)CC2)nc1]

Step A. Preparation of 2-(4-(methylsulfonyl)phenyl)-5-(piperidin-4-yloxy)pyridazin-3(2H)-one, TFA salt A mixture of Example 8 (10 mg, 0.022 mmol) and TFA (17 uL, 0.22 mmol) in $CH_2Cl_2$ (1 mL) was stirred for 5 hours and then concentrated in vacuo. The obtained solid was dissolved in methanol (2 mL) and evaporated to give 9.7 mg of the crude product as a tan solid. MS (ESI) 350 (M+H).

Step B. Example 12

To a mixture of 2-(4-(methylsulfonyl)phenyl)-5-(piperidin-4-yloxy)-pyridazin-3(2H)-one TFA salt (9.7 mg, 0.02 mmol) in DMF (1 mL) at room temperature under argon was added DIPEA (7.7 uL, 0.04 mmol) and 2-chloro-5-ethylpyrimidine (4.7 mg, 0.03 mmol). The reaction mixture was heated at 95° C. overnight and cooled to room temperature. The resulting mixture was diluted with EtOAc (10 mL) and $H_2O$ (10 mL) and the aqueous layer was extracted further with EtOAc (5 mL×2). The combined extracts were washed with brine (10 mL×3), dried ($Na_2SO_4$) and evaporated. The crude product was purified by preparative HPLC ($C_{18}$ column; 10-100% methanol in water) to give Example 12 (3.6 mg, tan solid, 35%) upon lyophilization. $^1$H NMR (400 MHz, $CDCl_3$) δ ppm 1.24 (t, J=7.69 Hz, 3H), 1.85-2.05 (m, 2H), 2.05-2.26 (m, 2H), 2.56 (q, J=7.62 Hz, 2H), 3.07 (s, 3H), 3.75-3.98 (m, 2H), 3.97-4.30 (m, 2H), 4.51-4.81 (m, 1H), 6.31 (d, J=2.64 Hz, 1H), 7.76 (d, J=3.08 Hz, 1H), 7.88 (d, J=8.79 Hz, 2H), 8.04 (d, J=8.79 Hz, 2H), 8.36 (s, 2H). MS (ESI) 456 (M+H).

Example 13 tert-Butyl 4-(1-(4-methoxybenzyl)-6-oxo-3-phenyl-1,6-dihydropyridazin-4-yloxy)piperidine-1-carboxylate

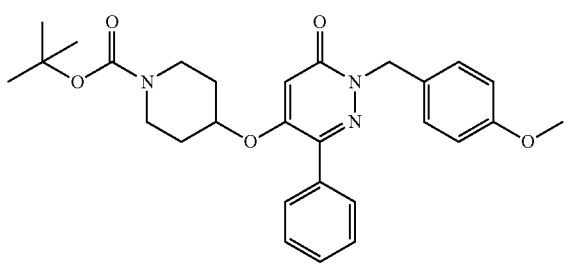 [SMILES: COc1ccc(Cn2nc(-c3ccccc3)c(OC3CCN(C(=O)OC(C)(C)C)CC3)cc2=O)cc1]

Step A. Preparation of 5-chloro-2-(4-methoxybenzyl)-6-phenylpyridazin-3(2H) one To a mixture of 5-chloro-6-phenylpyridazin-3(2H)-one (207 mg, 1.0 mmol) in DMF (3 mL) at room temperature under argon was added $K_2CO_3$ (415 mg, 3.0 mmol), and followed by addition of 1-(bromomethyl)-4-methoxybenzene (241 mg, 1.2 mmol). The resulting reaction mixture was stirred at room temperature overnight. Water (25 mL) was added to the reaction mixture and stirred for 1 hour. The product was collected by filtration and dried overnight under reduce pressure to yield 278 mg (81%) of 5-chloro-2-(4-methoxybenzyl)-6-phenylpyridazin-3(2H)-one as a tan solid. MS (ESI) 327 (M+H).

Step B. Example 13

To a mixture of tert-butyl 4-hydroxypiperidine-1-carboxylate (121 mg, 0.60 mmol) in THF (3 mL) at room temperature under argon was added NaH (24 mg, 0.60 mmol). After stirring at room temperature under argon for 30 minutes, 5-chloro-2-(4-methoxybenzyl)-6-phenylpyridazin-3(2H)-one (163 mg, 0.50 mmol) was added. The resulting reaction mixture was stirred at room temperature for three days. EtOAc (10 mL) and brine (10 mL) were added to the reaction mixture. Layers were separated. Organic layer were washed with water (15 mL), and brine (15 mL). Organic phase was dried ($MgSO_4$), filtered and concentrated. The crude product was dissolved in a small amount of DCM (~2 ml) and loaded onto a 40 g ISCO silica gel column which was eluted with a 20 min gradient from 0% to 100% EtOAc/Hexanes. 138.9 mg (56.3%) of tert-butyl-4-(1-(4-methoxybenzyl)-6-oxo-3-phenyl-1,6-dihydropyridazin-4-yloxy)piperidine-1-carboxylate was obtained as a white solid. $^1$H NMR (400 MHz, $CDCl_3$) δ ppm 1.43 (s, 9H) 1.62-1.82 (m, 2H) 1.80-1.98 (m, 2H) 3.16-3.57 (m, J=5.27, 5.27 Hz, 4H) 3.76 (s, 1H) 4.35-4.64 (m, 1H) 5.26 (s, 2H) 6.21 (s, 1H) 6.84 (d, J=8.79 Hz, 2H) 7.33-7.53 (m, 5H) 7.64 (dd, J=6.81, 3.30 Hz, 2H). MS (ESI) 492 (M+H).

Example 14

Methyl 4-(1-(tert-butoxycarbonyl)piperidin-4-yloxy)-1-(3,4-dichlorophenyl)-6-oxo-1,6-dihydropyridazine-3-carboxylate

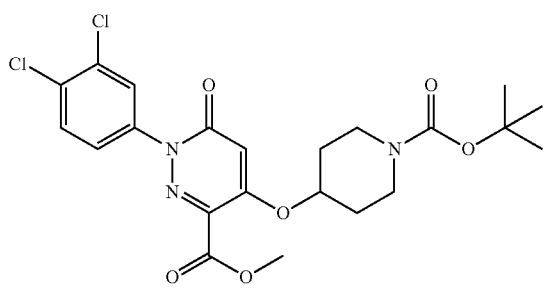 [SMILES: COC(=O)c1nn(-c2ccc(Cl)c(Cl)c2)c(=O)cc1OC1CCN(C(=O)OC(C)(C)C)CC1]

Step A. Preparation of 3,4-dichlorobenzenediazonium

To a mixture of 3,4-dichloroaniline (3.24 g, 20 mmol) in 10 mL of conc. HCl and water (20 mL) at 0° C. was added sodium nitrite (1.38 g, 20 mmol) in 15 mL of water. The resulting reaction mixture was stirred at 0° C. for 30 min. HPLC analysis indicated the reaction was completed. The reaction mixture was used directly in next step.

Step B. Preparation of (E)-dimethyl 2-(2-(3,4-dichlorophenyl)hydrazono)-3-oxopentanedioate To a mixture of dimethyl 3-oxopentanedioate (3.48 g, 20 mmol) in ethanol (12 mL) and water (40 mL) at room temperature was added sodium acetate (12.0 g, 146 mmol), and was followed by the addition of 3,4-dichlorobenzenediazonium solution (20 mmol). The resulting reaction mixture was stirred at room temperature for 1 h. The product was collected by filtration, then washed with water (~50 mL) and dried overnight under reduced pressure to yield 6.776 g (93%) of (E)-dimethyl 2-(2-(3,4-dichlorophenyl)hydrazono)-3-oxopentanedioate as a yellow solid. MS (ESI) 347 (M+H).

Step C. Preparation of methyl 1-(3,4-dichlorophenyl)-4-hydroxy-6-oxo-1,6-dihydropyridazine-3-carboxylate (E)-Dimethyl 2-(2-(3,4-dichlorophenyl)hydrazono)-3-oxopentanedioate (6.7 g, 19.3 mmol) in 1, 2 dichlorobenzene (20 mL) was heated at 180° C. overnight. After cooling, the reaction to room temperature, water 50 mL was added to the reaction mixture and it was stirred for 1 hour. The product was collected by filtration and further washed with water 20 mL and methanol (10 mL×3), then dried overnight under reduce pressure to yield 3.73 g (55.2%) of methyl 1-(3,4-dichlorophenyl)-4-hydroxy-6-oxo-1,6-dihydropyridazine-3-carboxylate as a tan solid. MS (ESI) 315 (M+H).

Step D. Example 14

To a mixture of methyl 1-(3,4-dichlorophenyl)-4-hydroxy-6-oxo-1,6-dihydropyridazine-3-carboxylate (315 mg, 1.0 mmol) in DMF (3 mL) at room temperature under argon was added $K_2CO_3$ (415 mg, 3.0 mmol) and tert-butyl 4-(methylsulfonyloxy)piperidine-1-carboxylate (419 mg, 1.5 mmol). The reaction mixture was heated at 95° C. overnight. EtOAc (20 mL) and water (20 mL) were added to the reaction mixture. Layers were separated. Organic layer were washed with water (15 mL), and brine (15 mL). Organic phase was dried ($MgSO_4$), filtered and concentrated. The crude product was dissolved in a small amount of DCM (~2 ml) and loaded onto a 40 g ISCO silica gel column which was eluted with a 20 min gradient from 20% to 100% EtOAc/Hexanes. 72 mg (14.2%) of methyl 4-(1-(tert-butoxycarbonyl)piperidin-4-yloxy)-1-(3,4-dichlorophenyl)-6-oxo-1,6-dihydropyridazine-3-carboxylate was obtained as a gum. $^1$H NMR (400 MHz, $CDCl_3$) δ ppm 1.40-1.50 (m, 9H) 1.68-1.82 (m, 1H) 1.92 (d, J=3.08 Hz, 3H) 3.23-3.45 (m, 2H) 3.49-3.59 (m, 1H) 3.59-3.73 (m, 1H) 3.82-4.03 (m, 3H) 4.48-5.43 (m, 1H) 6.12-6.38 (m, 1H) 7.38-7.64 (m, 2H) 7.75 (dd, J=7.91, 2.20 Hz, 1H). MS (ESI) 442 (M+H-tBu).

Example 15 tert-Butyl 4-(1-(3,4-dichlorophenyl)-3-(methylcarbamoyl)-6-oxo-1,6-dihydropyridazin-4-yloxy)piperidine-1-carboxylate

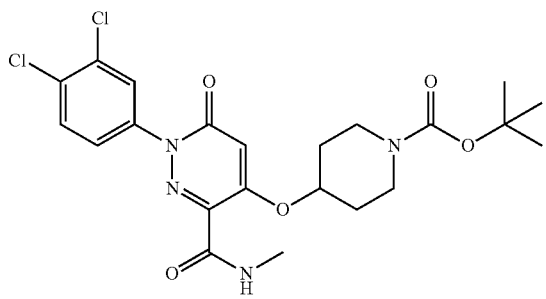 [SMILES: CNC(=O)c1nn(-c2ccc(Cl)c(Cl)c2)c(=O)cc1OC1CCN(C(=O)OC(C)(C)C)CC1]

Step A. Preparation of 4-(1-(tert-butoxycarbonyl)piperidin-4-yloxy)-1-(3,4-dichlorophenyl)-6-oxo-1,6-dihydropyridazine-3-carboxylic acid Methyl 4-(1-(tert-butoxycarbonyl)piperidin-4-yloxy)-1-(3,4-dichlorophenyl)-6-oxo-1,6-dihydropyridazine-3-carboxylate (example 14) (59.8 mg, 0.12 mmol) in THF (2 mL) at room temperature under argon was added 2M NaOH (0.18 mL, 0.36 mmol). The reaction mixture was stirred at room temperature overnight. Most of the product was precipitated out. Solvents were removed in vacuo. 10 mL of water and 1 mL of 1 M HCl were added. The product was collected by filtration and further washed with water (3 mL×2). After drying overnight, 56.7 mg (96%) of 4-(1-(tert-butoxycarbonyl)piperidin-4-yloxy)-1-(3,4-dichlorophenyl)-6-oxo-1,6-dihydropyridazine-3-carboxylic acid was obtained as a white solid. MS (ESI) 428 (M+H-tBu).

Step B. Example 15

To a mixture of 4-(1-(tert-butoxycarbonyl)piperidin-4-yloxy)-1-(3,4-dichlorophenyl)-6-oxo-1,6-dihydropyridazine-3-carboxylic acid (23 mg, 0.047 mmol) in THF (1 ml) at room temperature under argon was added HOBt (8.0 mg, 0.052 mmol), EDC (10.01 mg, 0.052 mmol), and was followed by 1 M methylamine in THF (0.237 mL, 0.237 mmol). The reaction mixture was stirred at room temperature overnight. EtOAc (10 mL) and 1 N NaOH (10 mL) were added to the reaction mixture. Layers were separated. Organic layer were washed with water (10 mL), and brine (10 mL). Organic phase was dried ($MgSO_4$), filtered and concentrated. The crude product was purified by preparative HPLC ($C_{18}$ column; 10-100% methanol in water without TFA) to give tert-butyl 4-(1-(3,4-dichlorophenyl)-3-(methylcarbamoyl)-6-oxo-1,6-dihydropyridazin-4-yloxy)piperidine-1-carboxylate (10 mg, white solid, 40.9%). $^1$H NMR (400 MHz, $CDCl_3$) δ ppm 1.45 (s, 9H) 1.78-2.05 (m, 4H) 2.96 (d, J=5.27 Hz, 3H) 3.43-3.57 (m, 2H) 3.57-3.72 (m, 2H) 4.49-4.71 (m, 1H) 6.28 (s, 1H) 6.58-6.69 (m, J=3.95 Hz, 1H) 7.46 (dd, 1H) 7.54 (d, 1H) 7.70 (d, J=2.20 Hz, 1H). MS (ESI) 441 (M+H-tBu).

Example 16 tert-Butyl 4-(3-carbamoyl-1-(3,4-dichlorophenyl)-6-oxo-1,6-dihydropyridazin-4-yloxy)piperidine-1-carboxylate

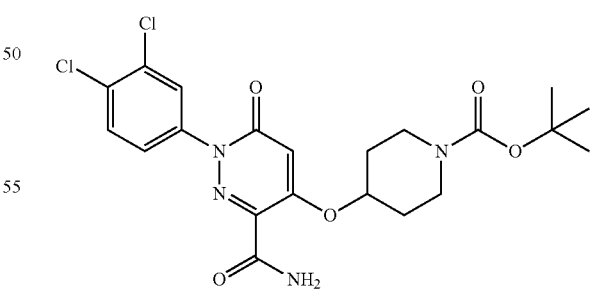

Example 16 was prepared in 68.7% yield according to procedures described in Example 15 substituting 1 M methylamine in THF for 0.5 M ammonia in dioxane. $^1$H NMR (400 MHz, $CDCl_3$) δ ppm 1.46 (s, 9H) 1.77-2.10 (m, 4H) 3.38-3.57 (m, 2H) 3.57-3.73 (m, 2H) 4.44-4.78 (m, 1H) 5.57 (s, 1H) 6.30 (s, 1H) 6.65 (s, 1H) 7.47 (dd, 1H) 7.51-7.58 (m, 1H) 7.71 (d, J=2.20 Hz, 1H). MS (ESI) 427 (M+H-tBu).

Example 17 tert-Butyl 4-(1-(3,4-dichlorophenyl)-3-(hydroxymethyl)-6-oxo-1,6-dihydropyridazin-4-yloxy)piperidine-1-carboxylate

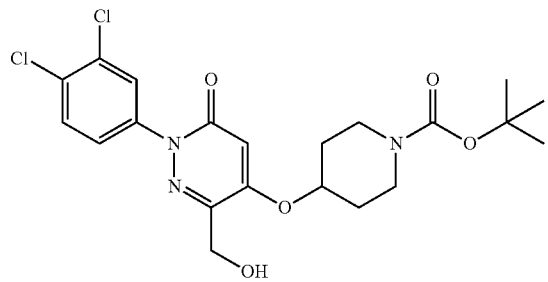 [SMILES: CC(C)(C)OC(=O)N1CCC(Oc2cc(=O)n(-c3ccc(Cl)c(Cl)c3)nc2CO)CC1]

To a mixture of 4-(1-(tert-butoxycarbonyl)piperidin-4-yloxy)-1-(3,4-dichlorophenyl)-6-oxo-1,6-dihydropyridazine-3-carboxylic acid (from example 15 step A) (5 mg, 0.01 mmol) in THF (1 ml) at room temperature under argon was added 1 M $BH_3$ in THF (31 uL, 0.031 mmol). The reaction mixture was stirred at room temperature for one hour. Methanol (2 mL) was carefully added to the reaction mixture and stirred at room temperature for two hours. Solvents were removed in vacuo. EtOAc (10 mL) and 1 N NaOH (10 mL) were added to the reaction mixture. Layers were separated. Organic layer were washed with water (10 mL), and brine (10 mL). Organic phase was dried ($MgSO_4$), filtered and concentrated. The crude product was purified by preparative HPLC ($C_{18}$ column; 10-100% methanol in water without TFA) to give tert-butyl 4-(1-(3,4-dichlorophenyl)-3-(hydroxymethyl)-6-oxo-1,6-dihydropyridazin-4-yloxy)piperidine-1-carboxylate (2.3 mg, gum, 42.6%). $^1$H NMR (400 MHz, $CDCl_3$) δ ppm 1.45-1.48 (m, 9H) 1.68-1.93 (m, J=3.95 Hz, 2H) 1.88-2.17 (m, 2H) 2.65-2.84 (m, 1H) 3.27-3.46 (m, 2H) 3.55-3.76 (m, 2H) 4.43-4.60 (m, 1H) 4.67 (s, 2H) 6.08-6.35 (m, 1H) 7.40-7.62 (m, 2H) 7.63-7.83 (m, 1H). MS (ESI) 414 (M+H-tBu).

Example 18

Methyl 4-(1-(tert-butoxycarbonyl)piperidin-4-yloxy)-1-(4-(methylsulfonyl)phenyl)-6-oxo-1,6-dihydropyridazine-3-carboxylate

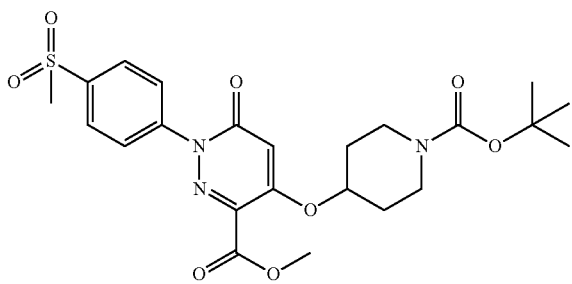 [SMILES: COC(=O)c1nn(-c2ccc(S(C)(=O)=O)cc2)c(=O)cc1OC1CCN(C(=O)OC(C)(C)C)CC1]

Step A. Preparation of 4-(methylsulfonyl)benzenediazonium

To a mixture of 4-(methylsulfonyl) aniline (3.42 g, 20 mmol) in 10 mL of conc. HCl and water (20 mL) at 0° C. was added sodium nitrite (1.38 g, 20 mmol) in 15 mL of water. The resulting reaction mixture was stirred at 0° C. for about 30 min. The reaction mixture was used directly to next step.

Step B. Preparation of (E)-dimethyl 2-(2-(4-(methylsulfonyl)phenyl)hydrazono)-3-oxopentanedioate To a mixture of dimethyl 3-oxopentanedioate (3.48 g, 20 mmol) in ethanol (12 mL) and water (40 mL) at room temperature was added sodium acetate (12.0 g, 146 mmol), and was followed by addition of 4-(methylsulfonyl)benzenediazonium solution (20 mmol). The resulting reaction mixture was stirred at room temperature for 1 h. The product was collected by filtration, then washed with water (~50 mL) and dried overnight under reduce pressure to yield 7.0 g (83%) of (E)-dimethyl 2-(2-(4-(methylsulfonyl)phenyl)hydrazono)-3-oxopentanedioate as a yellow solid. MS (ESI) 357 (M+H).

Step C. Preparation of methyl 4-hydroxy-1-(4-(methylsulfonyl)phenyl)-6-oxo-1,6-dihydropyridazine-3-carboxylate The mixture of (E)-dimethyl 2-(2-(4-(methylsulfonyl)phenyl) hydrazono)-3-oxopentanedioate (7.0 g, 19.6 mmol) in 1, 2 dichlorobenzene (20 mL) was heated at 180° C. overnight. After cooling the reaction to room temperature, water 50 mL was added to the reaction mixture and stirred for 1 hour. The product was collected by filtration and further washed with water 20 mL and methanol (10 mL×3), then dried overnight under reduced pressure to yield 3.13 g (49.1%) of methyl 4-hydroxy-1-(4-(methylsulfonyl)phenyl)-6-oxo-1,6-dihydropyridazine-3-carboxylate. MS (ESI) 325 (M+H).

Step D. Example 18

Example 18 was prepared in 12.2% yield according to procedures described in Example 14 substituting methyl 1-(3, 4-dichlorophenyl)-4-hydroxy-6-oxo-1,6-dihydropyridazine-3-carboxylate for methyl 4-hydroxy-1-(4-(methylsulfonyl) phenyl)-6-oxo-1,6-dihydropyridazine-3-carboxylate. $^1$H NMR (400 MHz, $CDCl_3$) δ ppm 1.40-1.50 (m, 9H) 1.68-1.82 (m, 1H) 1.92 (d, J=3.08 Hz, 3H) 3.23-3.45 (m, 2H) 3.49-3.59 (m, 1H) 3.59-3.73 (m, 1H) 3.82-4.03 (m, 3H) 4.48-5.43 (m, 1H) 6.12-6.38 (m, 1H) 7.38-7.64 (m, 2H) 7.75 (dd, J=7.91, 2.20 Hz, 1H). MS (ESI) 452 (M+H-tBu).

Example 19 tert-Butyl 4-(1-(4-methoxybenzyl)-6-oxo-1,6-dihydropyridazin-4-yloxy)piperidine-1-carboxylate

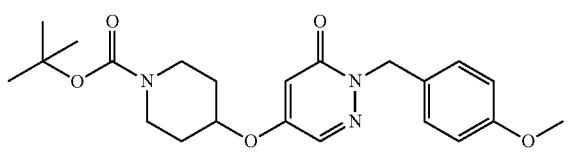 [SMILES: COc1ccc(Cn2ncc(OC3CCN(C(=O)OC(C)(C)C)CC3)cc2=O)cc1]

Step A. Preparation of 5-methoxy-2-(4-methoxybenzyl)pyridazin-3(2H)-one

To a stirring solution of 5-chloro-6-phenylpyridazin-3 (2H)-one (78 mg, 0.618 mmol) in DMF (3 mL) at room temperature under argon was added $K_2CO_3$ (256 mg, 1.855 mmol), and was followed by addition of 1-(bromomethyl)-4-methoxybenzene (149 mg, 0.742 mmol). The resulting reaction mixture was stirred at room temperature overnight. EtOAc (20 mL) and brine (30 mL) were added to the reaction mixture. Layers were separated. Organic layer were washed with water (15 mL), and brine (15 mL). Organic phase was dried (MgSO$_4$), filtered and concentrated. Crude product (117 mg) (MS (ESI) 247 (M+H)) was used directly to next step.

Step B. Preparation of 5-hydroxy-2-(4-methoxybenzyl)pyridazin-3(2H)-one

To a stirring solution of 5-methoxy-2-(4-methoxybenzyl) pyridazin-3(2H)-one (117 mg, 0.47 mmol) in THF (3 mL) at room temperature under argon was added 1M NaOH (2.0 mL, 2.0 mmol). The resulting reaction mixture was heated at 80° C. under argon for a day and monitored by LCMS until the reaction was completed. EtOAc (20 mL), 1 M HCl (2 mL), and water (10 mL) were added to the reaction mixture. Layers were separated. Organic layer were washed with water (15 mL), and brine (15 mL). Organic phase was dried (MgSO$_4$), filtered and concentrated. The crude product was dissolved in a small amount of DCM (~2 ml) and loaded onto a 40 g ISCO silica gel column which was eluted with a 20 min gradient from 20% to 100% EtOAc/Hexanes. 95 mg (77%) of 5-hydroxy-2-(4-methoxybenzyl)pyridazin-3(2H)-one was obtained as a gum. MS (ESI) 233 (M+H).

Step C. Example 19

Example 19 was prepared in 84% yield according to procedures described in Example 14 substituting methyl 1-(3,4-dichlorophenyl)-4-hydroxy-6-oxo-1,6-dihydropyridazine-3-carboxylate for 5-hydroxy-2-(4-methoxybenzyl)pyridazin-3(2H)-one. $^1$H NMR (400 MHz, CDCl$_3$) δ ppm 1.45 (s, 9H) 1.71 (dd, J=12.08, 4.17 Hz, 2H) 1.83-2.00 (m, 2H) 3.18-3.38 (m, 2H) 3.56-3.74 (m, 2H) 3.77 (s, 3H) 4.10-4.55 (m, 1H) 5.18 (s, 2H) 6.08 (d, J=2.64 Hz, 1H) 6.84 (d, J=8.79 Hz, 2H) 7.36 (d, J=8.79 Hz, 2H) 7.51 (d, J=2.64 Hz, 1H). MS (ESI) 360 (M+H-tBu).

Example 20 tert-Butyl 4-(3-cyano-1-(3,4-dichlorophenyl)-6-oxo-1,6-dihydropyridazin-4-yloxy) piperidine-1-carboxylate

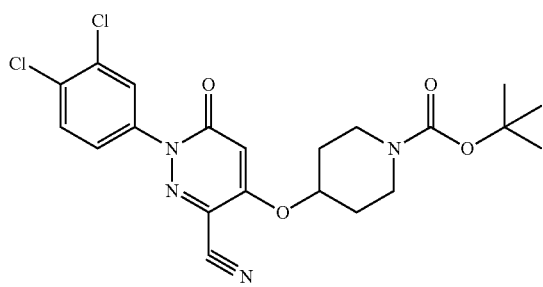 [SMILES: CC(C)(C)OC(=O)N1CCC(Oc2cc(=O)n(-c3ccc(Cl)c(Cl)c3)nc2C#N)CC1]

To a stirring solution of tert-butyl 4-(3-carbamoyl-1-(3,4-dichlorophenyl)-6-oxo-1,6-dihydropyridazin-4-yloxy)piperidine-1-carboxylate (example 16) (9 mg, 0.019 mmol) in THF (1 mL) at room temperature under argon was added TEA (5.65 mg, 0.056 mmol), and was followed by addition of TFAA (11.73 mg, 0.056 mmol). The resulting reaction mixture was stirred at room temperature overnight. Solvent was removed in vacuo. The crude product was purified by preparative HPLC (C$_{18}$ column; 10-100% methanol in water without TFA) to give tert-butyl 4-(3-cyano-1-(3,4-dichlorophenyl)-6-oxo-1,6-dihydropyridazin-4-yloxy)piperidine-1-carboxylate (6 mg, white solid, 69.2%). $^1$H NMR (400 MHz, CDCl$_3$) δ ppm 1.47 (s, 9H) 1.74-1.94 (m, 2H) 1.92-2.12 (m, 2H) 3.32-3.55 (m, 2H) 3.58-3.81 (m, 2H) 4.42-4.72 (m, 1H) 6.26 (s, 1H) 7.45 (dd, J=8.79, 2.20 Hz, 1H) 7.55 (d, 1H) 7.72 (d, J=2.20 Hz, 1H). MS (ESI) 409 (M+H-tBu).

Example 21

4-(1-(5-Cyclopropylpyrimidin-2-yl)piperidin-4-yloxy)-1-(3,4-dichlorophenyl)-6-oxo-1,6-dihydropyridazine-3-carbonitrile

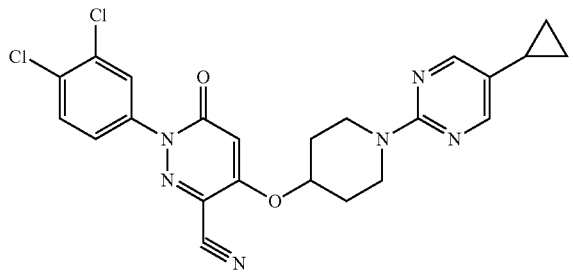 [SMILES: N#Cc1nn(-c2ccc(Cl)c(Cl)c2)c(=O)cc1OC1CCN(c2ncc(C3CC3)cn2)CC1]

Step A. Preparation of 1-(3,4-dichlorophenyl)-6-oxo-4-(piperidin-4-yloxy)-1,6-dihydropyridazine-3-carbonitrile, HCl salt To a stirring solution of Example 20 (400 mg, 0.860 mmol) in DCM (3 mL) at room temperature under argon was added 4 M HCl in dioxane (1.075 mL, 4.3 mmol). The reaction mixture was stirred at room temperature overnight. Et$_2$O (10 mL) was added to the reaction mixture. The solid product was collected by filtration and further washed with ether (5 mL×2). After drying under vacuum for 2 hours, 302 mg (96%) of 1-(3,4-dichlorophenyl)-6-oxo-4-(piperidin-4-yloxy)-1,6-dihydropyridazine-3-carbonitrile HCl salt was obtained as an off-white solid. MS (ESI) 365 (M+H).

Step B. Example 21

To a stirring solution of 1-(3,4-dichlorophenyl)-6-oxo-4-(piperidin-4-yloxy)-1,6-dihydropyridazine-3-carbonitrile HCl (50 mg, 0.137 mmol) in NMP (2 mL) at room temperature under argon was added DIPEA (53.1 mg, 0.411 mmol) and 2-chloro-5-cyclopropylpyrimidine (31.7 mg, 0.205 mmol). The resulting reaction mixture was heated at 100° C. under argon overnight. 15 mL of EtOAc was added to the reaction mixture. The reaction mixture was washed with water (15 mL), and brine (15 mL). Organic phase was dried (MgSO$_4$), filtered and concentrated. The crude product was dissolved in a small amount of DCM (~2 ml) and loaded onto a 40 g ISCO silica gel column which was eluted with a 20 min gradient from 20% to 100% EtOAc/Hexanes. 27 mg (38.8%) of 4-(1-(5-cyclopropylpyrimidin-2-yl)piperidin-4-yloxy)-1-(3,4-dichlorophenyl)-6-oxo-1,6-dihydropyridazine-3-carbonitrile was obtained as a white solid. $^1$H NMR (400 MHz, CDCl$_3$) δ ppm 0.50-0.66 (m, 2H) 0.82-0.98 (m, 2H) 1.64-

1.79 (m, 1H) 1.83-1.99 (m, 2H) 1.99-2.16 (m, 2H) 3.60-3.90 (m, 2H) 3.96-4.25 (m, 2H) 4.56-4.87 (m, 1H) 6.31 (s, 1H) 7.41-7.50 (m, 1H) 7.50-7.60 (m, 1H) 7.73 (d, J=2.20 Hz, 1H) 8.05-8.18 (m, 2H). MS (ESI) 483 (M+H).

Example 22

1-(3,4-Dichlorophenyl)-6-oxo-4-(1-(5-propylpyrimidin-2-yl)piperidin-4-yloxy)-1,6-dihydropyridazine-3-carbonitrile

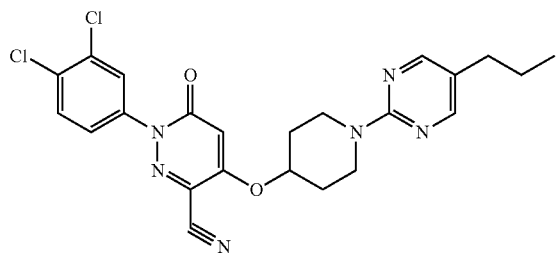 [SMILES: CCCc1cnc(N2CCC(Oc3cc(=O)n(-c4ccc(Cl)c(Cl)c4)nc3C#N)CC2)nc1]

Example 22 was prepared in 31% yield according to procedures described in Example 21 substituting 2-chloro-5-cyclopropylpyrimidine for 2-chloro-5-propylpyrimidine. $^1$H NMR (400 MHz, CDCl$_3$) δ ppm 0.93 (t, J=7.47 Hz, 3H) 1.45-1.67 (m, 4H) 1.81-2.00 (m, 2H) 2.00-2.17 (m, 2H) 2.41 (t, J=7.47 Hz, 2H) 3.57-3.89 (m, 2H) 4.01-4.29 (m, 2H) 4.57-4.79 (m, 1H) 6.26-6.36 (m, 1H) 7.38-7.50 (m, 1H) 7.50-7.63 (m, 1H) 7.73 (d, J=2.64 Hz, 1H) 8.07-8.28 (m, 2H). MS (ESI) 485 (M+H).

Example 23

4-(1-(5-Chloropyrimidin-2-yl)piperidin-4-yloxy)-1-(3,4-dichlorophenyl)-6-oxo-1,6-dihydropyridazine-3-carbonitrile

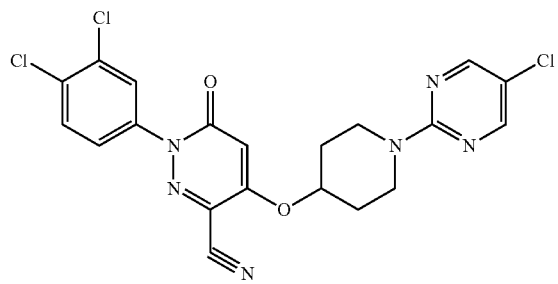 [SMILES: N#Cc1nn(-c2ccc(Cl)c(Cl)c2)c(=O)cc1OC1CCN(c2ncc(Cl)cn2)CC1]

Example 23 was prepared in 42% yield according to procedures described in Example 21 substituting 2-chloro-5-cyclopropylpyrimidine for 5-chloro-2-iodopyrimidine. $^1$H NMR (400 MHz, CDCl$_3$) δ ppm 1.86-2.00 (m, 2H) 2.01-2.13 (m, 2H) 3.71-3.94 (m, 2H) 3.95-4.19 (m, 2H) 4.54-4.82 (m, 1H) 6.31 (s, 1H) 7.46 (dd, J=8.79, 2.64 Hz, 1H) 7.51-7.60 (m, 1H) 7.73 (d, J=2.64 Hz, 1H) 8.24 (s, 2H). MS (ESI) 477 (M+H).

Example 24

1-(3,4-Dichlorophenyl)-4-(1-(5-iodopyrimidin-2-yl)piperidin-4-yloxy)-6-oxo-1,6-dihydropyridazine-3-carbonitrile

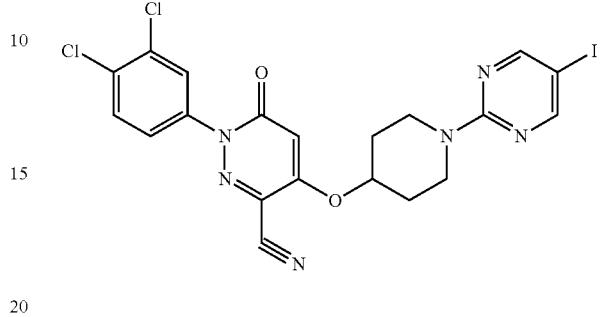

Step A. Preparation of 2-chloro-5-iodopyrimidine

To a stirring solution of 5-iodopyrimidin-2-amine (2.21 g, 10.0 mmol) in CH$_3$CN (20 ml) at room temperature under argon was added copper (II) chloride (2.02 g, 15 mmol) and tert-butyl nitrite (1.55 g, 15 mmol). The reaction mixture was placed in a preheated oil bath (60° C.) under Argon. The reaction mixture was cooled to room temperature and 20 ml of ether was added. The resulting insoluble material was filtered and the filtrate was concentrated. The crude product was dissolved in a small amount of DCM (~2 ml) and loaded onto an 80 g ISCO silica gel column which was eluted with a 20 min gradient from 0% to 100% EtOAc/Hexanes. 778 mg (31%) of 2-chloro-5-iodopyrimidine was obtained as an off-white solid. $^1$H NMR (400 MHz, CDCl$_3$) δ ppm 8.79 (s, 2H).

Step B. Example 24

Example 24 was prepared in 52% yield according to procedures described in Example 21 substituting 2-chloro-5-cyclopropylpyrimidine for 2-chloro-5-iodopyrimidine. $^1$H NMR (400 MHz, CDCl$_3$) δ ppm 1.86-2.00 (m, 2H) 2.01-2.13 (m, 2H) 3.71-3.94 (m, 2H) 3.95-4.19 (m, 2H) 4.54-4.82 (m, 1H) 6.31 (s, 1H) 7.46 (dd, J=8.79, 2.64 Hz, 1H) 7.51-7.60 (m, 1H) 7.73 (d, J=2.64 Hz, 1H) 8.24 (s, 2H). MS (ESI) 569 (M+H).

Example 25 tert-Butyl 4-(3-amino-1-(3,4-dichlorophenyl)-6-oxo-1,6-dihydropyridazin-4-yloxy)piperidine-1-carboxylate

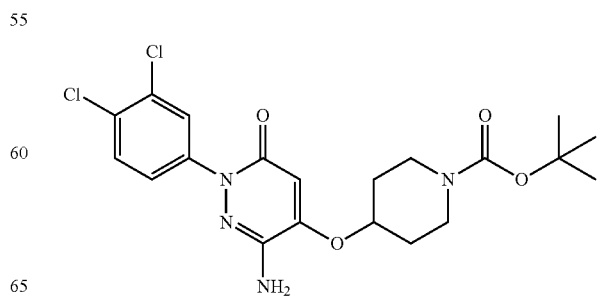

Step A. Preparation of tert-butyl 4-(1-(3,4-dichlorophenyl)-6-oxo-3-((2-(trimethylsilyl)ethoxy)carbonylamino)-1,6-dihydropyridazin-4-yloxy)piperidine-1-carboxylate To a stirring solution of 4-(1-(tert-butoxycarbonyl)piperidin-4-yloxy)-1-(3,4-dichlorophenyl)-6-oxo-1,6-dihydropyridazine-3-carboxylic acid (from example 15 step A) (48 mg, 0.10 mmol) in dioxane (10 mL) at room temperature under argon was added diphenyl phosphorazidate (65 mg, 0.20 mmol) and TEA (51 mg, 0.50 mmol). The resulting reaction mixture was stirred at room temperature for 1 hour, then 2-(trimethylsilyl)ethanol (118 mg, 1.0 mmol) was added. The resulting reaction mixture was heated at 80° C. under argon overnight. Solvent was concentrated. Crude reaction mixture was used directly to next step. MS (ESI) 597 (M−H).

Step B. Example 25

To a stirring solution of tert-butyl 4-(1-(3,4-dichlorophenyl)-6-oxo-3-((2-(trimethylsilyl)ethoxy)carbonylamino)-1,6-dihydropyridazin-4-yloxy)piperidine-1-carboxylate (60 mg, 0.10 mmol) in THF (10 ml) at room temperature under argon was added 1M TBAF in THF (1 mL, 1.0 mmol). The reaction mixture was stirred at room temperature overnight. Solvent was removed in vacuo. The crude product was directly purified by preparative HPLC ($C_{18}$ column; 10-100% methanol in water without TFA) to give tert-butyl 4-(3-amino-1-(3,4-dichlorophenyl)-6-oxo-1,6-dihydropyridazin-4-yloxy)piperidine-1-carboxylate (28 mg, white solid, 55%). $^1$H NMR (400 MHz, CDCl$_3$) δ ppm 1.34-1.55 (m, 9H) 1.65-1.91 (m, 2H) 2.04 (dd, J=12.96, 3.30 Hz, 2H) 3.06-3.39 (m, 2H) 3.59-3.94 (m, 2H) 4.29-4.71 (m, 2H) 6.20 (s, 1H) 7.43-7.50 (m, 1H) 7.54-7.64 (m, 1H) 7.80 (d, J=2.20 Hz, 1H). MS (ESI) 455 (M+H).

Example 26

1-(3,4-Dichlorophenyl)-6-oxo-4-(1-(5-(trifluoromethyl)pyrimidin-2-yl)piperidin-4-yloxy)-1,6-dihydropyridazine-3-carbonitrile

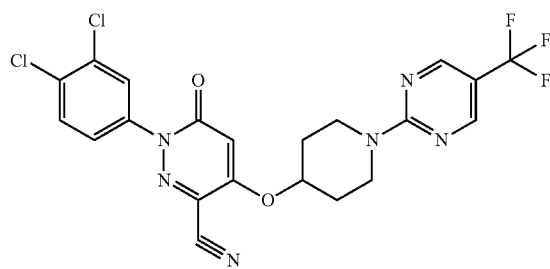 [SMILES: N#Cc1nn(-c2ccc(Cl)c(Cl)c2)c(=O)cc1OC1CCN(c2ncc(C(F)(F)F)cn2)CC1]

To a stirring solution of 1-(3,4-dichlorophenyl)-4-(1-(5-iodopyrimidin-2-yl)piperidin-4-yloxy)-6-oxo-1,6-dihydropyridazine-3-carbonitrile (example 24) (49.3 mg, 0.087 mmol) in DMF (2 mL) at room temperature under argon was added copper(I) iodide (33 mg, 0.173 umol) and fluorosulfonyl(difluoro) acetic acid methyl ester (33.3 mg, 0.173 mol). The reaction mixture was heated at 100° C. overnight. The reaction was cooled to room temperature. EtOAc (10 mL) was added to the reaction mixture, which was washed with brine (15 mL×3). Organic phase was dried (MgSO$_4$), filtered and concentrated. The crude product was dissolved in a small amount of DCM (~2 ml) and loaded onto a 40 g ISCO silica gel column which was eluted with a 20 min gradient from 0% to 100% EtOAc/Hexanes. 43 mg (92%) of 1-(3,4-dichlorophenyl)-6-oxo-4-(1-(5-(trifluoromethyl)pyrimidin-2-yl) piperidin-4-yloxy)-1,6-dihydropyridazine-3-carbonitrile was obtained as a brown solid. $^1$H NMR (400 MHz, CDCl$_3$) δ ppm 1.86-2.00 (m, 2H) 2.01-2.13 (m, 2H) 3.71-3.94 (m, 2H) 3.95-4.19 (m, 2H) 4.54-4.82 (m, 1H) 6.31 (s, 1H) 7.46 (dd, J=8.79, 2.64 Hz, 1H) 7.51-7.60 (m, 1H) 7.73 (d, J=2.64 Hz, 1H) 8.24 (s, 2H). MS (ESI) 511 (M+H).

Example 27 tert-Butyl 4-(3-chloro-1-(3,4-dichlorophenyl)-6-oxo-1,6-dihydropyridazin-4-yloxy)piperidine-1-carboxylate

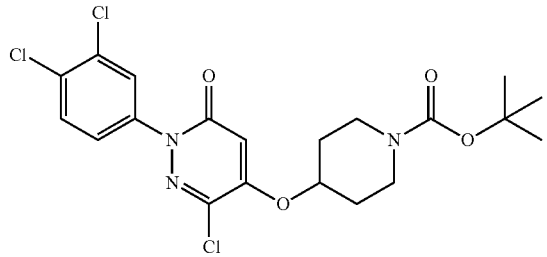 [SMILES: CC(C)(C)OC(=O)N1CCC(Oc2cc(=O)n(-c3ccc(Cl)c(Cl)c3)nc2Cl)CC1]

To a stirring solution of tert-butyl 4-(3-amino-1-(3,4-dichlorophenyl)-6-oxo-1,6-dihydropyridazin-4-yloxy)piperidine-1-carboxylate (20 mg, 0.044 mmol) in CH$_3$CN (5 ml) at room temperature under argon was added copper(II) chloride (8.86 mg, 0.066 mmol) and tert-butyl nitrite (6.79 mg, 0.066 mmol). The reaction mixture was placed in a preheated oil bath (60° C.) under Argon. The reaction mixture was cooled to room temperature and 20 ml of ether was added. The resulting insoluble material was filtered and the filtrate was concentrated. The crude product was directly purified by preparative HPLC (C$_{18}$ column; 10-100% methanol in water without TFA) to give tert-butyl 4-(3-chloro-1-(3,4-dichlorophenyl)-6-oxo-1,6-dihydropyridazin-4-yloxy)piperidine-1-carboxylate (2.3 mg, white solid, 11%). $^1$H NMR (400 MHz, CDCl$_3$) δ ppm 1.47 (s, 9H) 1.81-1.92 (m, 3H) 1.92-2.05 (m, 2H) 3.48 (s, 2H) 3.57-3.70 (m, 2H) 4.21-4.77 (m, 1H) 6.24 (s, 1H) 7.51 (s, 2H) 7.76 (s, 1H). MS (ESI) 420 (M+H-tBu).

Example 28

2-(3,4-Dichlorophenyl)-5-(1-(5-propylpyrimidin-2-yl)piperidin-4-yloxy)pyridazin-3(2H)-one

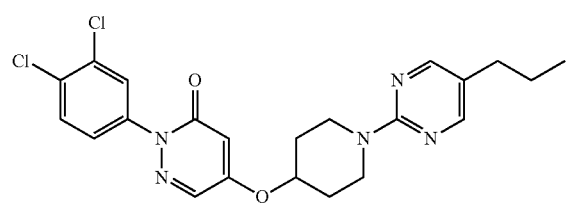 [SMILES: CCCc1cnc(N2CCC(Oc3cnn(-c4ccc(Cl)c(Cl)c4)c(=O)c3)CC2)nc1]

Step A. Preparation of 1-(3,4-dichlorophenyl)-6-oxo-4-(piperidin-4-yloxy)-1,6-dihydropyridazine-3-carboxylic acid To a stirring solution of 4-(1-(tert-butoxycarbonyl)piperidin-4-yloxy)-1-(3,4-dichlorophenyl)-6-oxo-1,6-dihydropyridazine-3-carboxylic acid (from example 15 step A) (105 mg, 0.217 mmol) in DCM (2 mL) at room temperature under argon was added 4 M HCl in dioxane (0.271 mL, 1.1 mmol). The reaction mixture was stirred at room temperature overnight. Et$_2$O (10 mL) was added to the reaction mixture. The solid product was collected by filtration and further washed with ether (5 mL×2). After drying under reduce pressure over night, 83 mg (100%) of 1(3,4-dichlorophenyl)-6-oxo-4-(piperidin-4-yloxy)-1,6-dihydropyridazine-3-carboxylic acid HCl salt was obtained as an off-white solid. MS (ESI) 384 (M+H).

Step B. Preparation of 1-(3,4-dichlorophenyl)-6-oxo-4-(1-(5-propylpyrimidin-2-yl)piperidin-4-yloxy)-1,6-dihydropyridazine-3-carboxylic acid To a stirring solution of 1-(3,4-dichlorophenyl)-6-oxo-4-(piperidin-4-yloxy)-1,6-dihydropyridazine-3-carboxylic acid HCl (83 mg, 0.217 mmol) in NMP (2 mL) at room temperature under argon was added DIPEA (84 mg, 0.651 mmol) and 2-chloro-5-propylpyrimidine (51 mg, 0.326 mmol). The resulting reaction mixture was heated at 100° C. under argon overnight. 15 mL of EtOAc was added to the reaction mixture. The reaction mixture was washed with water (15 mL), and brine (15 mL). Organic phase was dried (MgSO$_4$), filtered and concentrated. The crude product was directly purified by preparative HPLC (C$_{18}$ column; 10-100% methanol in water without TFA) to give 1-(3,4-dichlorophenyl)-6-oxo-4-(1-(5-propylpyrimidin-2-yl)piperidin-4-yloxy)-1,6-dihydropyridazine-3-carboxylic acid (57 mg, white solid, 52%). MS (ESI) 504 (M+H).

Step C. Example 28

To a stirring solution of 1-(3,4-dichlorophenyl)-6-oxo-4-(1-(5-propylpyrimidin-2-yl)piperidin-4-yloxy)-1,6-dihydropyridazine-3-carboxylic acid (15 mg, 0.03 mmol) in NMP (2 mL) at room temperature under argon was added K$_2$CO$_3$ (8.22 mg, 0.06 mmol). The reaction mixture was heated at 150° C. overnight. The crude product was directly purified by preparative HPLC (C$_{18}$ column; 10-100% methanol in water without TFA) to give 2-(3,4-dichlorophenyl)-5-(1-(5-propylpyrimidin-2-yl)piperidin-4-yloxy)pyridazin-3(2H)-one (9.5 mg, tan solid, 66%). $^1$H NMR (400 MHz, CDCl$_3$) δ ppm 0.93 (t, J=7.47 Hz, 2H) 1.38-1.72 (m, 2H) 1.81-2.02 (m, 2H) 2.00-2.21 (m, 2H) 2.40 (t, J=7.69 Hz, 2H) 3.50-3.80 (m, 2H) 4.06-4.37 (m, 2H) 4.47-4.68 (m, 1H) 5.56 (s, 1H) 7.28 (dd, J=8.57, 2.42 Hz, 2H) 7.44-7.72 (m, 2H) 8.16 (s, 2H). MS (ESI) 461 (M+H).

Example 29

Methyl 4-(1-(tert-butoxycarbonyl)piperidin-4-yloxy)-1-(4-cyano-3-fluorophenyl)-6-oxo-1,6-dihydropyridazine-3-carboxylate

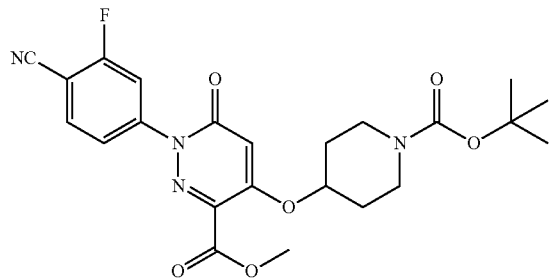 [SMILES: COC(=O)c1nn(-c2ccc(C#N)c(F)c2)c(=O)cc1OC1CCN(C(=O)OC(C)(C)C)CC1]

Step A. Preparation of 4-amino-2-fluorobenzonitrile

The mixture of 2-fluoro-4-nitrobenzonitrile (8.31 g, 50 mmol) and tin (II) chloride dihydrate (56.4 g, 250 mmol) in 250 mL of EtOAc was stirred at 25° C. overnight. LCMS (78109-084) indicated the reaction was completed. 25 mL of sat. K$_2$CO$_3$ was added to the reaction. The resulting mixture was stirred at room temperature for 2 h and was followed by addition of 100 g of solid K$_2$CO$_3$. The mixture was stirred at room temperature for 2 hours. Solid was removed by filtration and further washed with EtOAc (50 mL×2). The filtrate was concentrated to yield 6.81 g (100%) of 4-amino-2-fluorobenzonitrile as an off white solid. $^1$H NMR (400 MHz, CDCl$_3$) δ ppm 4.30 (s, 2H) 6.29-6.51 (m, 2H) 7.27-7.40 (m, 1H). MS (ESI) 137 (M+H).

Step B. Preparation of 4-cyano-3-fluorobenzenediazonium

4-Cyano-3-fluorobenzenediazonium was prepared in 100% yield according to procedures described in Example 18 (Step A) substituting 4-(methylsulfonyl)aniline for 4-amino-2-fluorobenzonitrile. The reaction mixture was used directly to next step.

Step C. Preparation of (E)-dimethyl 2-(2-(4-cyano-3-fluorophenyl)hydrazono)-3-oxopentanedioate (E)-Dimethyl 2-(2-(4-cyano-3-fluorophenyl)hydrazono)-3-oxopentanedioate was prepared in 86% yield according to procedures described in Example 18 (Step B) substituting 4-(methylsulfonyl)benzenediazonium for 4-cyano-3-fluorobenzenediazonium. MS (ESI) 322 (M+H).

Step D. Preparation of methyl 1-(4-cyano-3-fluorophenyl)-4-hydroxy-6-oxo-1,6-dihydropyridazine-3-carboxylate Methyl 1-(4-cyano-3-fluorophenyl)-4-hydroxy-6-oxo-1,6-dihydropyridazine-3-carboxylate was prepared in 73% yield according to procedures described in Example 18 (Step C) substituting (E)-dimethyl 2-(2-(4-(methylsulfonyl)phenyl)hydrazono)-3-oxopentanedioate for (E)-Dimethyl 2-(2-(4-cyano-3-fluorophenyl)hydrazono)-3-oxopentanedioate. MS (ESI) 322 (M+H).

Step E. Example 29

Example 29 was prepared in 74% yield according to procedures described in Example 14 substituting methyl 1-(3,4-dichlorophenyl)-4-hydroxy-6-oxo-1,6-dihydropyridazine-3-carboxylate for methyl 1-(4-cyano-3-fluorophenyl)-4-hydroxy-6-oxo-1,6-dihydropyridazine-3-carboxylate with MS (4A) in the reaction mixture. $^1$H NMR (400 MHz, CDCl$_3$) δ ppm 1.46 (s, 9H) 1.72-2.13 (m, 4H) 3.26-3.74 (m, 17H) 3.94 (s, 3H) 4.35-4.78 (m, 1H) 6.26 (s, 1H) 7.52-7.87 (m, 3H). MS (ESI) 473 (M+H).

Example 30

Methyl 4-(1-(tert-butoxycarbonyl)piperidin-4-yloxy)-1-(6-cyanopyridin-3-yl)-6-oxo-1,6-dihydropyridazine-3-carboxylate

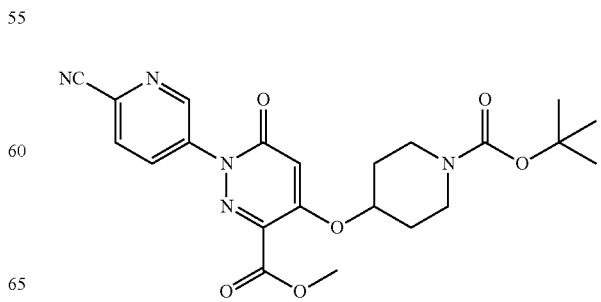

Step A. Preparation of 6-cyanopyridine-3-diazonium

6-Cyanopyridine-3-diazonium was prepared in 100% yield according to procedures described in Example 18 (Step A) substituting 4-(methylsulfonyl)aniline for 5-aminopicolinonitrile. The reaction mixture was used directly to next step.

Step B. Preparation of (E)-dimethyl 2-(2-(6-cyanopyridin-3-yl)hydrazono)-3-oxopentanedioate (E)-Dimethyl 2-(2-(6-cyanopyridin-3-yl)hydrazono)-3-oxopentanedioate was prepared in 87% yield according to procedures described in Example 18 (Step B) substituting 4-(methylsulfonyl)benzenediazonium for 6-cyanopyridine-3-diazonium. MS (ESI) 305 (M+H).

Step C. Preparation of methyl 1-(6-cyanopyridin-3-yl)-4-hydroxy-6-oxo-1,6-dihydropyridazine-3-carboxylate Methyl 1-(6-cyanopyridin-3-yl)-4-hydroxy-6-oxo-1,6-dihydropyridazine-3-carboxylate was prepared in 90% yield according to procedures described in Example 18 (Step C) substituting (E)-dimethyl 2-(2-(4-(methylsulfonyl)phenyl)hydrazono)-3-oxopentanedioate for (E)-dimethyl 2-(2-(6-cyanopyridin-3-yl)hydrazono)-3-oxopentanedioate. MS (ESI) 273 (M+H).

Step D. Example 30

Example 30 was prepared in 67% yield according to procedures described in Example 14 substituting methyl 1-(3,4-dichlorophenyl)-4-hydroxy-6-oxo-1,6-dihydropyridazine-3-carboxylate for Methyl 1-(6-cyanopyridin-3-yl)-4-hydroxy-6-oxo-1,6-dihydropyridazine-3-carboxylate with MS (4A) in the reaction mixture. $^1$H NMR (400 MHz, CDCl$_3$) δ ppm 1.46 (s, 9H) 1.73-2.20 (m, 4H) 3.29-3.74 (m, 4H) 3.95 (s, 3H) 4.52-4.83 (m, 1H) 6.27 (s, 1H) 7.79 (d, J=8.35 Hz, 1H) 8.25 (dd, J=8.57, 2.42 Hz, 1H) 9.09 (d, J=2.20 Hz, 1H). MS (ESI) 465 (M+H).

Example 31 tert-Butyl 4-(3-cyano-1-(4-(methylsulfonyl)phenyl)-6-oxo-1,6-dihydropyridazin-4-yloxy)piperidine-1-carboxylate

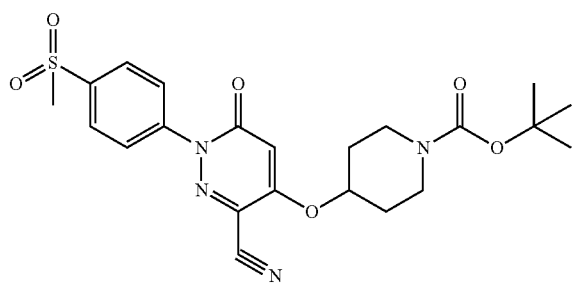 [SMILES: CC(C)(C)OC(=O)N1CCC(Oc2cc(=O)n(-c3ccc(S(C)(=O)=O)cc3)nc2C#N)CC1]

Step A. Preparation of tert-butyl 4-(3-carbamoyl-1-(4-(methylsulfonyl)phenyl)-6-oxo-1,6-dihydropyridazin-4-yloxy)piperidine-1-carboxylate To a stirring solution of methyl 4-(1-(tert-butoxycarbonyl)piperidin-4-yloxy)-1-(4-(methylsulfonyl)phenyl)-6-oxo-1,6-dihydropyridazine-3-carboxylate (1015 mg, 2.0 mmol) in THF (15 mL) at room temperature under argon was added 7M ammonia in methanol (4.3 mL, 30 mmol). The reaction mixture was stirred at room temperature overnight. The solvents were removed in vacuo. The crude product 1.0 g (100%) was used directly to next step. MS (ESI) 437 (M+H-tBu).

Step B. Example 31

To a stirring solution of tert-butyl 4-(3-carbamoyl-1-(4-(methylsulfonyl)phenyl)-6-oxo-1,6-dihydropyridazin-4-yloxy)piperidine-1-carboxylate (985 mg, 2.0 mmol) in THF (50 mL) at room temperature under argon was added TEA (405 mg, 4.0 mmol), and was followed by addition of TFAA (840 mg, 4.0 mmol). The resulting reaction mixture was stirred at room temperature overnight. The solvent was removed in vacuo. The crude product was dissolved in a small amount of DCM (~5 ml) and loaded onto a 40 g ISCO silica gel column which was eluted with a 20 min gradient from 20% to 100% EtOAc/Hexanes. 908 mg (91%) of tert-butyl 4-(3-cyano-1-(4-(methylsulfonyl)phenyl)-6-oxo-1,6-dihydropyridazin-4-yloxy)piperidine-1-carboxylate was obtained as a white solid. $^1$H NMR (400 MHz, CDCl$_3$) δ ppm 1.43-1.51 (m, 9H) 1.81-1.95 (m, 2H) 1.95-2.09 (m, 2H) 3.27-3.57 (m, 2H) 3.57-3.88 (m, 2H) 4.38-4.81 (m, 1H) 6.29 (s, 1H) 7.83 (d, J=8.35 Hz, 1H) 8.20 (dd, J=8.57, 2.42 Hz, 1H) 9.04 (d, J=2.64 Hz, 1H). MS (ESI) 419 (M+H-tBu).

Example 32

Methyl 1-(4-cyano-3-fluorophenyl)-6-oxo-4-(1-(5-propylpyrimidin-2-yl)piperidin-4-yloxy)-1,6-dihydropyridazine-3-carboxylate

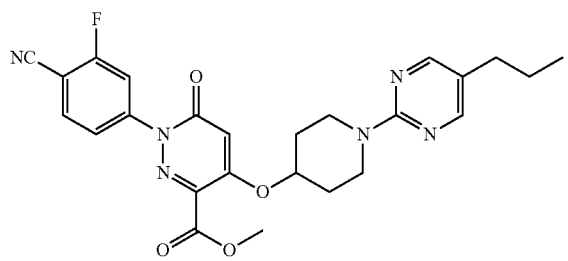 [SMILES: CCCc1cnc(N2CCC(Oc3cc(=O)n(-c4ccc(C#N)c(F)c4)nc3C(=O)OC)CC2)nc1]

Step A. Preparation of methyl 1-(4-cyano-3-fluorophenyl)-6-oxo-4-(piperidin-4-yloxy)-1,6-dihydropyridazine-3-carboxylate, HCl salt To a stirring solution of methyl 4-(1-(tert-butoxycarbonyl)piperidin-4-yloxy)-1-(4-cyano-3-fluorophenyl)-6-oxo-1,6-dihydropyridazine-3-carboxylate (142 mg, 0.30 mmol) in DCM (3 mL) at room temperature under argon was added 4 M HCl in dioxane (0.375 mL, 1.5 mmol). The reaction mixture was stirred at room temperature overnight. Et$_2$O (10 mL) was added to the reaction mixture. The solid product was collected by filtration and further washed with ether (2 mL×2). After drying under reduced pressure for 2 hours, 105 mg of methyl 1-(4-cyano-3-fluorophenyl)-6-oxo-4-(piperidin-4-yloxy)-1,6-dihydropyridazine-3-carboxylate HCl salt was obtained as an off-white solid. MS (ESI) 373 (M+H).

Step B. Example 32

To a stirring solution of methyl 1-(4-cyano-3-fluorophenyl)-6-oxo-4-(piperidin-4-yloxy)-1,6-dihydropyridazine-3-carboxylate HCl (37.2 mg, 0.10 mmol) in NMP (3 mL) at room temperature under argon was added DIPEA (38.8 mg, 0.30 mmol) and 2-chloro-5-propylpyrimidine (23.5 mg, 0.15 mmol). The resulting reaction mixture was heated at 95° C. under argon overnight. 15 mL of EtOAc was added to the reaction mixture. The reaction mixture was washed with water (15 mL), and brine (15 mL). Organic phase was dried (MgSO$_4$), filtered and concentrated. The crude product was directly purified by preparative HPLC (C$_{18}$ column; 10-100% methanol in water without TFA) to give methyl 1-(4-cyano-3-fluorophenyl)-6-oxo-4-(1-(5-propylpyrimidin-2-yl)piperidin-4-yloxy)-1,6-dihydropyridazine-3-carboxylate (16 mg, white solid, 32%). $^1$H NMR (400 MHz, CDCl$_3$) δ ppm 0.56-1.12 (m, 3H) 1.37-1.67 (m, 2H) 1.70-2.20 (m, 4H) 2.39 (q, J=7.47 Hz, 2H) 3.64-4.09 (m, 7H) 4.02-4.40 (m, 1H) 4.40-4.95 (m, 1H) 6.31 (s, 1H) 7.45-7.91 (m, 3H) 7.91-8.46 (m, 2H). MS (ESI) 493 (M+H).

Example 33

Methyl 1-(4-cyano-3-fluorophenyl)-4-(1-(5-cyclopropylpyrimidin-2-yl)piperidin-4-yloxy)-6-oxo-1,6-dihydropyridazine-3-carboxylate

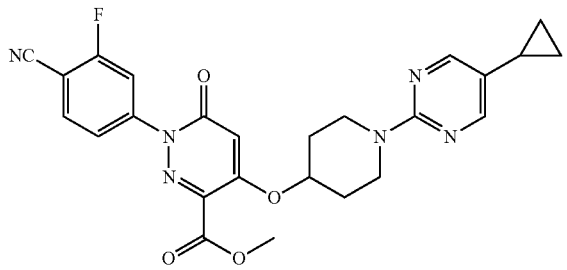 [SMILES: COC(=O)c1nn(-c2ccc(C#N)c(F)c2)c(=O)cc1OC1CCN(c2ncc(C3CC3)cn2)CC1]

Example 33 was prepared in 31% yield according to procedures described in Example 32 (Step B) substituting 2-chloro-5-propylpyrimidine for 2-chloro-5-cyclopropylpyrimidine. $^1$H NMR (400 MHz, CDCl$_3$) δ ppm 0.41-0.73 (m, 2H) 0.74-1.08 (m, 2H) 1.50-1.78 (m, 2H) 1.76-2.31 (m, 8H) 3.33-3.78 (m, 2H) 3.82-4.01 (m, 3H) 4.00-4.43 (m, 2H) 4.55-4.80 (m, 1H) 6.30 (s, 1H) 7.55-7.81 (m, 3H) 8.00-8.29 (m, 2H). MS (ESI) 491 (M+H).

Example 34 tert-Butyl 4-(3-cyano-1-(4-cyano-3-fluorophenyl)-6-oxo-1,6-dihydropyridazin-4-yloxy)piperidine-1-carboxylate

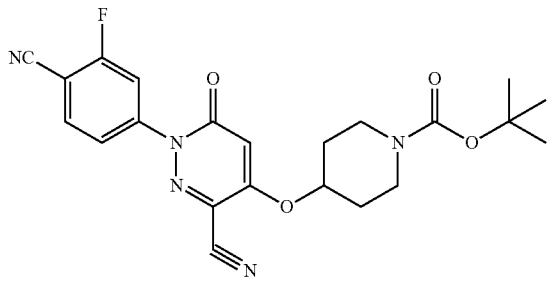 [SMILES: CC(C)(C)OC(=O)N1CCC(Oc2cc(=O)n(-c3ccc(C#N)c(F)c3)nc2C#N)CC1]

Step A. Preparation of tert-butyl 4-(3-carbamoyl-1-(4-cyano-3-fluorophenyl)-6-oxo-1,6-dihydropyridazin-4-yloxy)piperidine-1-carboxylate tert-Butyl 4-(3-carbamoyl-1-(4-cyano-3-fluorophenyl)-6-oxo-1,6-dihydropyridazin-4-yloxy)piperidine-1-carboxylate was prepared in 91% yield according to procedures described in Example 31 (Step A) substituting methyl 4-(1-(tert-butoxycarbonyl)piperidin-4-yloxy)-1-(4-(methylsulfonyl)phenyl)-6-oxo-1,6-dihydropyridazine-3-carboxylate for methyl 4-(1-(tert-butoxycarbonyl)piperidin-4-yloxy)-1-(4-cyano-3-fluorophenyl)-6-oxo-1,6-dihydropyridazine-3-carboxylate (example 29). MS (ESI) 402 (M+H-tBu).

Step B. Example 34

Example 34 was prepared in 84% yield according to procedures described in Example 31 (Step B) substituting tert-butyl 4-(3-carbamoyl-1-(4-(methylsulfonyl)phenyl)-6-oxo-1,6-dihydropyridazin-4-yloxy)piperidine-1-carboxylate for tert-Butyl 4-(3-carbamoyl-1-(4-cyano-3-fluorophenyl)-6-oxo-1,6-dihydropyridazin-4-yloxy)piperidine-1-carboxylate. $^1$H NMR (400 MHz, CDCl$_3$) δ ppm 1.47 (s, 9H) 1.77-1.94 (m, 2H) 1.94-2.08 (m, 2H) 3.35-3.57 (m, 2H) 3.56-3.74 (m, 2H) 4.40-4.78 (m, 1H) 6.28 (s, 1H) 7.57-7.70 (m, 2H) 7.71-7.80 (m, 1H). MS (ESI) 384 (M+H-tBu).

Example 35 tert-Butyl 4-(3-cyano-1-(6-cyanopyridin-3-yl)-6-oxo-1,6-dihydropyridazin-4-yloxy)piperidine-1-carboxylate

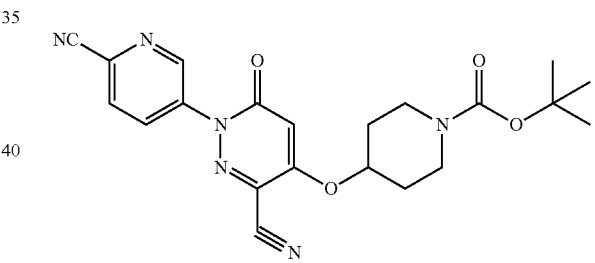

Step A. Preparation of tert-butyl 4-(3-carbamoyl-1-(6-cyanopyridin-3-yl)-6-oxo-1,6-dihydropyridazin-4-yloxy)piperidine-1-carboxylate tert-Butyl 4-(3-carbamoyl-1-(6-cyanopyridin-3-yl)-6-oxo-1,6-dihydropyridazin-4-yloxy)piperidine-1-carboxylate was prepared in 77% yield according to procedures described in Example 31 (Step A) substituting methyl 4-(1-(tert-butoxycarbonyl)piperidin-4-yloxy)-1-(4-(methylsulfonyl)phenyl)-6-oxo-1,6-dihydropyridazine-3-carboxylate for methyl 4-(1-(tert-butoxycarbonyl)piperidin-4-yloxy)-1-(6-cyanopyridin-3-yl)-6-oxo-1,6-dihydropyridazine-3-carboxylate (example 30). MS (ESI) 441 (M+H).

Step B. Example 35

Example 35 was prepared in 89% yield according to procedures described in Example 31 (Step B) substituting tert-butyl 4-(3-carbamoyl-1-(4-(methylsulfonyl)phenyl)-6-oxo-1,6-dihydropyridazin-4-yloxy)piperidine-1-carboxylate for tert-butyl 4-(3-carbamoyl-1-(6-cyanopyridin-3-yl)-6-oxo-1, 6-dihydropyridazin-4-yloxy)piperidine-1-carboxylate. $^1$H NMR (400 MHz, CDCl$_3$) δ ppm 1.43-1.51 (m, 9H) 1.81-1.95 (m, 2H) 1.95-2.09 (m, 2H) 3.27-3.57 (m, 2H) 3.57-3.88 (m, 2H) 4.38-4.81 (m, 1H) 6.29 (s, 1H) 7.83 (d, J=8.35 Hz, 1H) 8.20 (dd, J=8.57, 2.42 Hz, 1H) 9.04 (d, J=2.64 Hz, 1H). MS (ESI) 423 (M+H).

Example 36

1-(4-Cyano-3-fluorophenyl)-4-(1-(5-iodopyrimidin-2-yl)piperidin-4-yloxy)-6-oxo-1,6-dihydropyridazine-3-carbonitrile

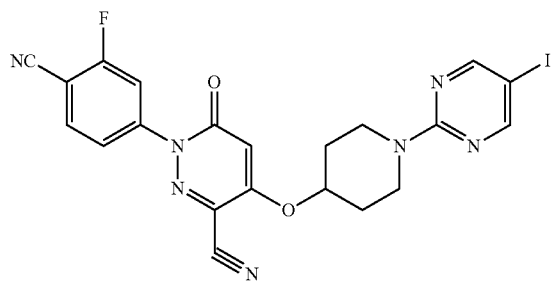 [SMILES: N#Cc1ccc(-n2nc(C#N)c(OC3CCN(c4ncc(I)cn4)CC3)cc2=O)cc1F]

Step A. Preparation of 1-(4-cyano-3-fluorophenyl)-6-oxo-4-(piperidin-4-yloxy)-1,6-dihydropyridazine-3-carbonitrile, HCl salt To a stirring solution of tert-butyl 4-(3-cyano-1-(4-cyano-3-fluorophenyl)-6-oxo-1,6-dihydropyridazin-4-yloxy)piperidine-1-carboxylate (example 34) (22 mg, 0.050 mmol) in DCM (3 mL) at room temperature under argon was added 4 M HCl in dioxane (0.375 mL, 1.5 mmol). The reaction mixture was stirred at room temperature overnight. Et$_2$O (10 mL) was added to the reaction mixture. The solid product was collected by filtration and further washed with ether (2 mL×2). After drying under vacuum for 2 hours, 19 mg (100%) of 1-(4-cyano-3-fluorophenyl)-6-oxo-4-(piperidin-4-yloxy)-1,6-dihydropyridazine-3-carbonitrile HCl salt was obtained as an off-white solid. MS (ESI) 340 (M+H).

Step B. Example 36

Example 36 was prepared in 71% yield according to procedures described in Example 21 substituting 2-chloro-5-cyclopropylpyrimidine and 1-(3,4-dichlorophenyl)-6-oxo-4-(piperidin-4-yloxy)-1,6-dihydropyridazine-3-carbonitrile HCl for 2-chloro-5-iodopyrimidine and 1-(4-cyano-3-fluorophenyl)-6-oxo-4-(piperidin-4-yloxy)-1,6-dihydropyridazine-3-carbonitrile HCl salt. $^1$H NMR (400 MHz, CDCl$_3$) δ ppm 1.83-2.00 (m, 2H) 1.98-2.20 (m, 2H) 3.71-3.95 (m, 2H) 3.95-4.13 (m, 2H) 4.53-4.84 (m, 1H) 6.31 (s, 1H) 7.57-7.70 (m, 2H) 7.70-7.81 (m, 1H) 8.41 (s, 2H). MS (ESI) 544 (M+H).

Example 37

1-(6-Cyanopyridin-3-yl)-4-(1-(5-iodopyrimidin-2-yl)piperidin-4-yloxy)-6-oxo-1,6-dihydropyridazine-3-carbonitrile

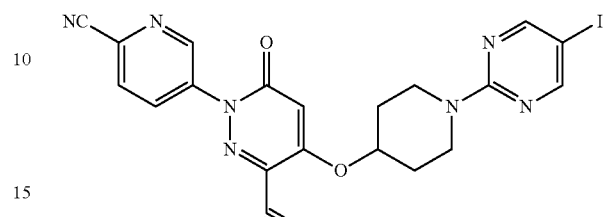

Step A. Preparation of 1-(6-cyanopyridin-3-yl)-6-oxo-4-(piperidin-4-yloxy)-1,6-dihydropyridazine-3-carbonitrile, HCl salt To a stirring solution of tert-butyl 4-(3-cyano-1-(6-cyanopyridin-3-yl)-6-oxo-1,6-dihydropyridazin-4-yloxy)piperidine-1-carboxylate (22 mg, 0.050 mmol) in DCM (3 mL) at room temperature under argon was added 4 M HCl in dioxane (0.375 mL, 1.5 mmol). The reaction mixture was stirred at room temperature overnight. Et$_2$O (10 mL) was added to the reaction mixture. The solid product was collected by filtration and further washed with ether (2 mL×2). After drying under vacuum for 2 hours, 17.3 mg (100%) of 1-(6-cyanopyridin-3-yl)-6-oxo-4-(piperidin-4-yloxy)-1,6-dihydropyridazine-3-carbonitrile HCl salt was obtained as an off-white solid. MS (ESI) 323 (M+H).

Step B. Example 37

Example 37 was prepared in 61% yield according to procedures described in Example 21 substituting 2-chloro-5-cyclopropylpyrimidine and 1-(3,4-dichlorophenyl)-6-oxo-4-(piperidin-4-yloxy)-1,6-dihydropyridazine-3-carbonitrile HCl for 2-chloro-5-iodopyrimidine and 1-(6-cyanopyridin-3-yl)-6-oxo-4-(piperidin-4-yloxy)-1,6-dihydropyridazine-3-carbonitrile HCl salt. $^1$H NMR (400 MHz, CDCl$_3$) δ ppm 1.83-2.00 (m, 2H) 1.98-2.20 (m, 2H) 3.71-3.95 (m, 2H) 3.95-4.13 (m, 2H) 4.53-4.84 (m, 1H) 6.31 (s, 1H) 7.57-7.70 (m, 2H) 7.70-7.81 (m, 1H) 8.41 (s, 2H). MS (ESI) 527 (M+H).

Example 38

1-(4-Cyano-3-fluorophenyl)-6-oxo-4-(1-(5-propylpyrimidin-2-yl)piperidin-4-yloxy)-1,6-dihydropyridazine-3-carbonitrile

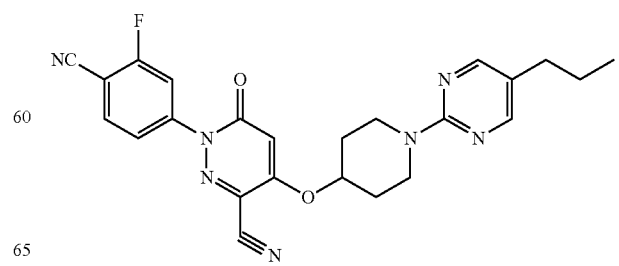

Example 38 was prepared in 56% yield according to procedures described in Example 21 substituting 2-chloro-5-cyclopropylpyrimidine and 1-(3,4-dichlorophenyl)-6-oxo-4-(piperidin-4-yloxy)-1,6-dihydropyridazine-3-carbonitrile HCl for 2-chloro-5-propylpyrimidine and 1-(4-cyano-3-fluorophenyl)-6-oxo-4-(piperidin-4-yloxy)-1,6-dihydropyridazine-3-carbonitrile HCl salt. $^1$H NMR (400 MHz, CDCl$_3$) δ ppm 0.93 (t, J=7.25 Hz, 3H) 1.48-1.67 (m, 2H) 1.82-2.01 (m, 2H) 2.01-2.17 (m, 2H) 2.41 (t, J=7.69 Hz, 2H) 3.60-3.91 (m, 2H) 3.98-4.27 (m, 2H) 4.48-4.87 (m, 1H) 6.32 (s, 1H) 7.52-7.70 (m, 2H) 7.70-7.81 (m, 1H) 8.17 (s, 2H). MS (ESI) 460 (M+H).

Example 39

1-(4-Cyano-3-fluorophenyl)-6-oxo-4-(1-(5-(trifluoromethyl)pyrimidin-2-yl)piperidin-4-yloxy)-1,6-dihydropyridazine-3-carbonitrile

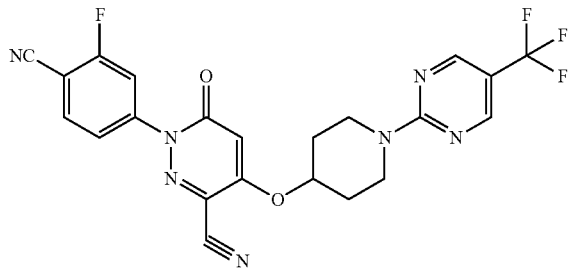 [SMILES: N#Cc1ccc(-n2nc(C#N)c(OC3CCN(c4ncc(C(F)(F)F)cn4)CC3)cc2=O)cc1F]

Example 39 was prepared in 76% yield according to procedures described in Example 26 substituting 1-(3,4-dichlorophenyl)-4-(1-(5-iodopyrimidin-2-yl)piperidin-4-yloxy)-6-oxo-1,6-dihydropyridazine-3-carbonitrile for 1-(4-cyano-3-fluorophenyl)-4-(1-(5-iodopyrimidin-2-yl)piperidin-4-yloxy)-6-oxo-1,6-dihydropyridazine-3-carbonitrile (example 36). $^1$H NMR (400 MHz, CDCl$_3$) δ ppm 1.94-2.04 (m, 2H) 2.04-2.15 (m, 2H) 3.83-4.29 (m, 4H) 4.53-4.93 (m, 1H) 6.13-6.46 (m, 1H) 7.55-7.70 (m, 2H) 7.75 (t, J=7.69 Hz, 1H) 8.50 (s, 2H). MS (ESI) 486 (M+H).

Example 40

1-(6-Cyanopyridin-3-yl)-6-oxo-4-(1-(5-(trifluoromethyl)pyrimidin-2-yl)piperidin-4-yloxy)-1,6-dihydropyridazine-3-carbonitrile

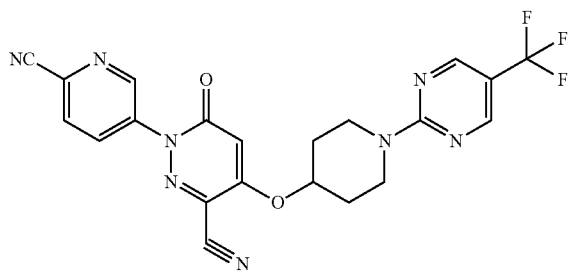 [SMILES: N#Cc1ccc(-n2nc(C#N)c(OC3CCN(c4ncc(C(F)(F)F)cn4)CC3)cc2=O)cn1]

Example 40 was prepared in 71% yield according to procedures described in Example 26 substituting 1-(3,4-dichlorophenyl)-4-(1-(5-iodopyrimidin-2-yl)piperidin-4-yloxy)-6-oxo-1,6-dihydropyridazine-3-carbonitrile for 1-(6-cyanopyridin-3-yl)-4-(1-(5-iodopyrimidin-2-yl)piperidin-4-yloxy)-6-oxo-1,6-dihydropyridazine-3-carbonitrile (example 37). $^1$H NMR (400 MHz, CDCl$_3$) δ ppm 1.91-2.05 (m, 2H) 2.05-2.20 (m, 2H) 3.85-4.30 (m, 4H) 4.59-4.88 (m, 1H) 6.16-6.45 (m, 1H) 7.84 (d, J=8.35 Hz, 1H) 8.21 (dd, J=8.57, 2.42 Hz, 1H) 8.51 (s, 2H) 9.06 (d, J=2.64 Hz, 1H). MS (ESI) 469 (M+H).

Example 41

4-(1-(5-Bromopyrimidin-2-yl)piperidin-4-yloxy)-1-(4-cyano-3-fluorophenyl)-6-oxo-1,6-dihydropyridazine-3-carbonitrile

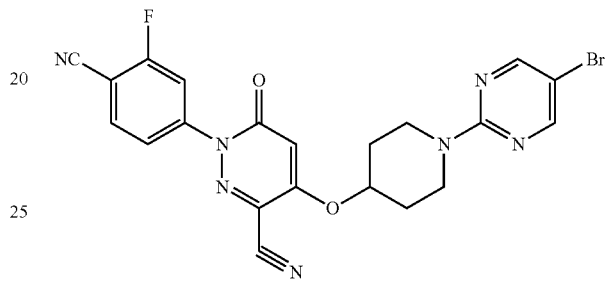

Example 41 was prepared in 89% yield according to procedures described in Example 21 substituting 2-chloro-5-cyclopropylpyrimidine and 1-(3,4-dichlorophenyl)-6-oxo-4-(piperidin-4-yloxy)-1,6-dihydropyridazine-3-carbonitrile HCl for 5-bromo-2-chloropyrimidine and 1-(4-cyano-3-fluorophenyl)-6-oxo-4-(piperidin-4-yloxy)-1,6-dihydropyridazine-3-carbonitrile HCl salt. $^1$H NMR (400 MHz, CDCl$_3$) δ ppm 0 1.90-2.01 (m, 2H) 2.01-2.19 (m, 2H) 3.78-3.91 (m, 2H) 3.99-4.19 (m, 2H) 4.52-4.93 (m, 1H) 6.32 (s, 1H) 7.60-7.71 (m, 2H) 7.71-7.82 (m, 1H) 8.31 (s, 2H). MS (ESI) 497 (M+H).

Example 42

Methyl 4-(1-(5-bromopyrimidin-2-yl)piperidin-4-yloxy)-1-(4-cyano-3-fluorophenyl)-6-oxo-1,6-dihydropyridazine-3-carboxylate

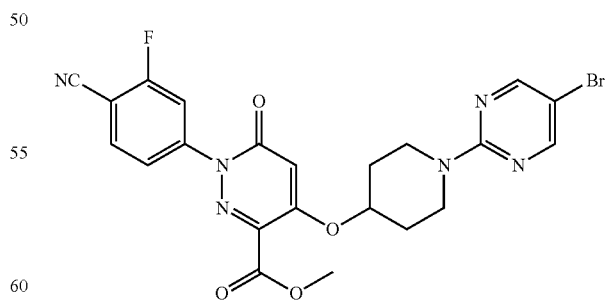

Example 42 was prepared in 78% yield according to procedures described in Example 32 (Step B) substituting 2-chloro-5-propylpyrimidine for 5-bromo-2-chloropyrimidine. $^1$H NMR (400 MHz, CDCl$_3$) δ ppm 1.45-1.50 (m, 9H) 1.80-1.95 (m, 2H) 1.95-2.08 (m, 2H) 3.08 (s, 3H) 3.33-3.58

(m, 2H) 3.55-3.81 (m, 2H) 4.45-4.78 (m, 1H) 6.30 (s, 1H) 7.83 (d, J=8.79 Hz, 2H) 8.07 (d, J=8.79 Hz, 2H). MS (ESI) 530 (M+H).

Example 43

Methyl 1-(4-bromo-3-fluorophenyl)-4-(1-(tert-butoxycarbonyl)piperidin-4-yloxy)-6-oxo-1,6-dihydropyridazine-3-carboxylate

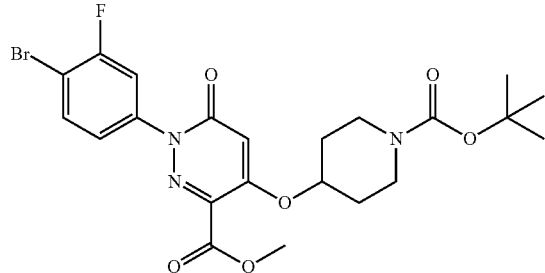

Step A. Preparation of 4-bromo-3-fluorobenzenediazonium

4-Bromo-3-fluorobenzenediazonium was prepared in 100% yield according to procedures described in Example 18 (Step A) substituting 4-(methylsulfonyl)aniline for 4-bromo-3-fluoroaniline. The reaction mixture was used directly to next step.

Step B. Preparation of (E)-dimethyl 2-(2-(4-bromo-3-fluorophenyl)hydrazono)-3-oxopentanedioate (E)-Dimethyl 2-(2-(4-bromo-3-fluorophenyl)hydrazono)-3-oxopentanedioate was prepared in 78% yield according to procedures described in Example 18 (Step B) substituting 4-(methylsulfonyl)benzenediazonium for 4-bromo-3-fluorobenzenediazonium. MS (ESI) 375 (M+H).

Step C. Preparation of methyl 1-(4-bromo-3-fluorophenyl)-4-hydroxy-6-oxo-1,6-dihydropyridazine-3-carboxylate Methyl 1-(4-bromo-3-fluorophenyl)-4-hydroxy-6-oxo-1,6-dihydropyridazine-3-carboxylate was prepared in 60% yield according to procedures described in Example 18 (Step C) substituting (E)-dimethyl 2-(2-(4-(methylsulfonyl)phenyl)hydrazono)-3-oxopentanedioate for (E)-Dimethyl 2-(2-(4-bromo-3-fluorophenyl)hydrazono)-3-oxopentanedioate. MS (ESI) 343 (M+H).

Step D. Example 43

Example 43 was prepared in 80% yield according to procedures described in Example 14 substituting methyl 1-(3,4-dichlorophenyl)-4-hydroxy-6-oxo-1,6-dihydropyridazine-3-carboxylate for methyl 1-(4-bromo-3-fluorophenyl)-4-hydroxy-6-oxo-1,6-dihydropyridazine-3-carboxylate with MS (4A) in the reaction mixture. $^1$H NMR (400 MHz, CDCl$_3$) δ ppm 1.46 (s, 9H) 1.73-2.08 (m, 4H) 3.39-3.67 (m, 4H) 3.93 (s, 3H) 4.44-4.74 (m, 1H) 6.26 (s, 1H) 7.36 (d, J=8.79 Hz, 1H) 7.47 (dd, J=9.23, 2.20 Hz, 1H) 7.56-7.71 (m, 1H). MS (ESI) 472 (M+H-tBu).

Example 44

Methyl 1-(4-bromo-2-fluorophenyl)-4-(1-(tert-butoxycarbonyl)piperidin-4-yloxy)-6-oxo-1,6-dihydropyridazine-3-carboxylate

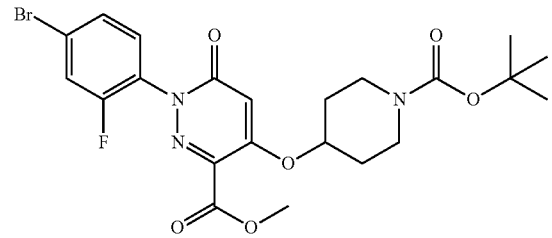 [SMILES: COC(=O)c1nn(-c2ccc(Br)cc2F)c(=O)cc1OC1CCN(C(=O)OC(C)(C)C)CC1]

Step A. Preparation of 4-bromo-2-fluorobenzenediazonium

4-Bromo-3-fluorobenzenediazonium was prepared in 100% yield according to procedures described in Example 18 (Step A) substituting 4-(methylsulfonyl) aniline for 4-bromo-2-fluoroaniline. The reaction mixture was used directly to next step.

Step B. Preparation of (E)-dimethyl 2-(2-(4-bromo-2-fluorophenyl)hydrazono)-3-oxopentanedioate (E)-Dimethyl 2-(2-(4-bromo-2-fluorophenyl)hydrazono)-3-oxopentanedioate was prepared in 83% yield according to procedures described in Example 18 (Step B) substituting 4-(methylsulfonyl)benzenediazonium for 4-bromo-2-fluorobenzenediazonium. MS (ESI) 375 (M+H).

Step C. Preparation of methyl 1-(4-bromo-2-fluorophenyl)-4-hydroxy-6-oxo-1,6-dihydropyridazine-3-carboxylate Methyl 1-(4-bromo-2-fluorophenyl)-4-hydroxy-6-oxo-1,6-dihydropyridazine-3-carboxylate was prepared in 51% yield according to procedures described in Example 18 (Step C) substituting (E)-dimethyl 2-(2-(4-(methylsulfonyl)phenyl)hydrazono)-3-oxopentanedioate for (E)-Dimethyl 2-(2-(4-bromo-2-fluorophenyl)hydrazono)-3-oxopentanedioate. MS (ESI) 343 (M+H).

Step D. Example 44

Example 44 was prepared in 75% yield according to procedures described in Example 14 substituting methyl 1-(3,4-dichlorophenyl)-4-hydroxy-6-oxo-1,6-dihydropyridazine-3-carboxylate for methyl 1-(4-bromo-2-fluorophenyl)-4-hydroxy-6-oxo-1,6-dihydropyridazine-3-carboxylate with MS (4A) in the reaction mixture. $^1$H NMR (400 MHz, CDCl$_3$) δ ppm 1.41-1.51 (m, 9H) 1.70-2.03 (m, 4H) 3.39-3.67 (m, 4H) 3.91 (s, 3H) 4.36-4.76 (m, 1H) 6.27 (s, 1H) 7.26-7.34 (m, 1H) 7.41 (d, J=9.23 Hz, 2H). MS (ESI) 472 (M+H-tBu).

Example 45 tert-Butyl 4-(1-(4-bromo-3-fluorophenyl)-3-cyano-6-oxo-1,6-dihydropyridazin-4-yloxy)piperidine-1-carboxylate

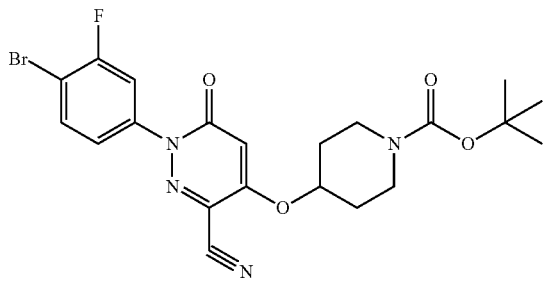

Step A. Preparation of tert-butyl 4-(1-(4-bromo-3-fluorophenyl)-3-carbamoyl-6-oxo-1,6-dihydropyridazin-4-yloxy)piperidine-1-carboxylate tert-Butyl 4-(1-(4-bromo-3-fluorophenyl)-3-carbamoyl-6-oxo-1,6-dihydropyridazin-4-yloxy)piperidine-1-carboxylate was prepared in 100% yield according to procedures described in Example 31 (Step A) substituting methyl 441-(tert-butoxycarbonyl)piperidin-4-yloxy)-1-(4-(methylsulfonyl)phenyl)-6-oxo-1,6-dihydropyridazine-3-carboxylate for methyl 1-(4-bromo-3-fluorophenyl)-4-(1-(tert-butoxycarbonyl)piperidin-4-yloxy)-6-oxo-1,6-dihydropyridazine-3-carboxylate (Example 43). MS (ESI) 511 (M+H).

Step B. Example 45

Example 45 was prepared in 82% yield according to procedures described in Example 31 (Step B) substituting tert-butyl 4-(3-carbamoyl-1-(4-(methylsulfonyl)phenyl)-6-oxo-1,6-dihydropyridazin-4-yloxy)piperidine-1-carboxylate for tert-Butyl 4-(1-(4-bromo-3-fluorophenyl)-3-carbamoyl-6-oxo-1,6-dihydropyridazin-4-yloxy)piperidine-1-carboxylate. $^1$H NMR (400 MHz, CDCl$_3$) δ ppm 1.47 (s, 9H) 1.79-1.94 (m, 2H) 1.95-2.09 (m, J=3.85 Hz, 2H) 3.34-3.56 (m, 2H) 3.59-3.88 (m, 2H) 4.47-4.78 (m, 1H) 6.26 (s, 1H) 7.31 (d, J=8.80 Hz, 1H) 7.40-7.52 (m, 1H) 7.60-7.76 (m, 1H). MS (ESI) 439 (M+H-tBu).

Example 46 tert-Butyl 4-(1-(4-bromo-2-fluorophenyl)-3-cyano-6-oxo-1,6-dihydropyridazin-4-yloxy)piperidine-1-carboxylate

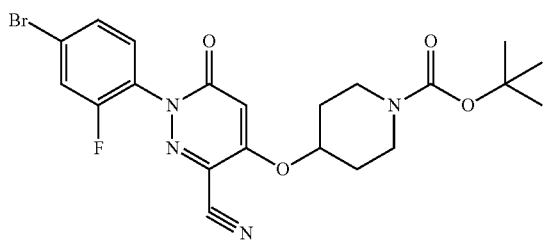 [SMILES: CC(C)(C)OC(=O)N1CCC(Oc2cc(=O)n(-c3ccc(Br)cc3F)nc2C#N)CC1]

Step A. Preparation of tert-butyl 4-(1-(4-bromo-2-fluorophenyl)-3-carbamoyl-6-oxo-1,6-dihydropyridazin-4-yloxy)piperidine-1-carboxylate tert-Butyl 4-(1-(4-bromo-2-fluorophenyl)-3-carbamoyl-6-oxo-1,6-dihydropyridazin-4-yloxy)piperidine-1-carboxylate was prepared in 100% yield according to procedures described in Example 31 (Step A) substituting methyl 441-(tert-butoxycarbonyl)piperidin-4-yloxy)-1-(4-(methylsulfonyl)phenyl)-6-oxo-1,6-dihydropyridazine-3-carboxylate for Methyl 1-(4-bromo-2-fluorophenyl)-4-(1-(tert-butoxycarbonyl)piperidin-4-yloxy)-6-oxo-1,6-dihydropyridazine-3-carboxylate (Example 44). MS (ESI) 511 (M+H).

Step B. Example 46

Example 46 was prepared in 78% yield according to procedures described in Example 31 (Step B) substituting tert-butyl 4-(3-carbamoyl-1-(4-(methylsulfonyl)phenyl)-6-oxo-1,6-dihydropyridazin-4-yloxy)piperidine-1-carboxylate for tert-Butyl 4-(1-(4-bromo-2-fluorophenyl)-3-carbamoyl-6-oxo-1,6-dihydropyridazin-4-yloxy)piperidine-1-carboxylate. $^1$H NMR (400 MHz, CDCl$_3$) δ ppm 1.47 (s, 9H) 1.79-1.94 (m, 2H) 1.94-2.08 (m, J=3.85 Hz, 2H) 3.29-3.54 (m, 2H) 3.53-3.86 (m, 2H) 4.36-4.78 (m, 1H) 6.26 (s, 1H) 7.10-7.37 (m, 2H) 7.43 (d, J=8.80 Hz, 1H). MS (ESI) 439 (M+H-tBu).

Example 47

4-(1-(5-Chloropyrimidin-2-yl)piperidin-4-yloxy)-1-(4-(methylsulfonyl)phenyl)-6-oxo-1,6-dihydropyridazine-3-carbonitrile

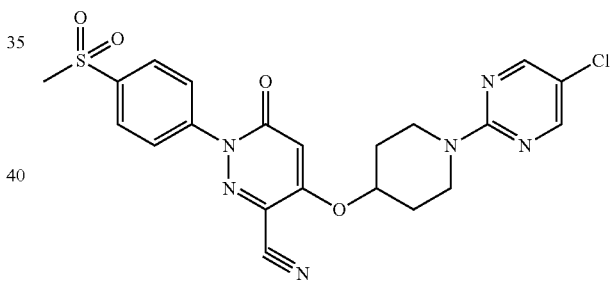

Step A. Preparation of 1-(4-(methylsulfonyl)phenyl)-6-oxo-4-(piperidin-4-yloxy)-1,6-dihydropyridazine-3-carbonitrile, HCl salt To a stirring solution of tert-butyl 4-(3-cyano-1-(4-(methylsulfonyl)phenyl)-6-oxo-1,6-dihydropyridazin-4-yloxy)piperidine-1-carboxylate (700 mg, 1.475 mmol) in DCM (10 mL) at room temperature under argon was added 4 M HCl in dioxane (3.69 mL, 14.75 mmol). The reaction mixture was stirred at room temperature overnight. Et$_2$O (10 mL) was added to the reaction mixture. The solid product was collected by filtration and further washed with ether (2 mL×2). After drying under vacuum for 2 hours, 567 mg (90%) of 1-(4-(methylsulfonyl)phenyl)-6-oxo-4-(piperidin-4-yloxy)-1,6-dihydropyridazine-3-carbonitrile HCl salt was obtained as an off-white solid. MS (ESI) 375 (M+H).

Step B. Example 47

To a stirring solution of 1-(4-(methylsulfonyl)phenyl)-6-oxo-4-(piperidin-4-yloxy)-1,6-dihydropyridazine-3-carbonitrile HCl (124 mg, 0.33 mmol) in NMP (3 mL) at room temperature under argon was added DIPEA (128 mg, 0.99 mmol) and 5-chloro-2-iodopyrimidine (159 mg, 0.66 mmol). The resulting reaction mixture was heated at 100° C. under argon overnight. 15 mL of EtOAc was added to the reaction mixture. The reaction mixture was washed with water (15 mL), and brine (15 mL). Organic phase was dried (MgSO$_4$), filtered and concentrated. The crude product was dissolved in a small amount of DCM (~3 ml) and loaded onto a 40 g ISCO silica gel column which was eluted with a 20 min gradient from 20% to 100% EtOAc/Hexanes. 121 mg (75%) of 4-(1-(5-chloropyrimidin-2-yl)piperidin-4-yloxy)-1-(4-(methylsulfonyl)phenyl)-6-oxo-1,6-dihydropyridazine-3-carbonitrile was obtained as a tan solid. $^1$H NMR (400 MHz, CDCl$_3$) δ ppm 1.75-2.27 (m, 4H) 3.08 (s, 3H) 3.66-3.97 (m, 2H) 3.97-4.24 (m, 2H) 4.54-4.95 (m, 1H) 6.34 (s, 1H) 7.84 (d, J=8.79 Hz, 2H) 8.07 (d, J=8.79 Hz, 2H) 8.24 (s, 2H). MS (ESI) 487 (M+H).

Example 48

4-(1-(5-Iodopyrimidin-2-yl)piperidin-4-yloxy)-1-(4-(methylsulfonyl)phenyl)-6-oxo-1,6-dihydropyridazine-3-carbonitrile

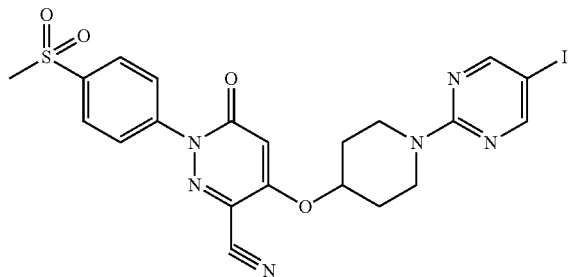 [SMILES: CS(=O)(=O)c1ccc(-n2nc(C#N)c(OC3CCN(c4ncc(I)cn4)CC3)cc2=O)cc1]

Example 48 was prepared in 69% yield according to procedures described in Example 47 (Step B) substituting 5-chloro-2-iodopyrimidine for 2-chloro-5-iodopyrimidine. $^1$H NMR (400 MHz, CDCl$_3$) δ ppm 1.83-2.02 (m, 2H) 1.99-2.18 (m, 2H) 3.09 (s, 3H) 3.73-3.95 (m, 2H) 3.95-4.24 (m, 2H) 4.54-4.85 (m, 1H) 6.33 (s, 1H) 7.84 (d, J=8.79 Hz, 2H) 7.96-8.20 (m, 2H) 8.41 (s, 2H). MS (ESI) 579 (M+H).

Example 49

1-(4-(Methylsulfonyl)phenyl)-6-oxo-4-(1-(5-(trifluoromethyl)pyrimidin-2-yl)piperidin-4-yloxy)-1,6-dihydropyridazine-3-carbonitrile

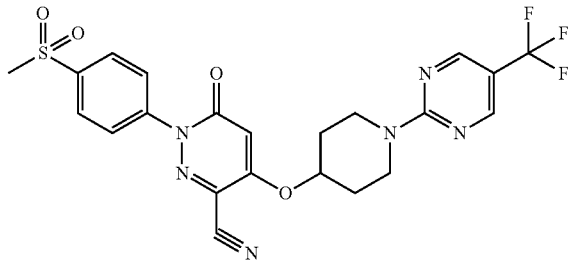 [SMILES: CS(=O)(=O)c1ccc(-n2nc(C#N)c(OC3CCN(c4ncc(C(F)(F)F)cn4)CC3)cc2=O)cc1]

Example 49 was prepared in 74% yield according to procedures described in Example 26 substituting 1-(3,4-dichlorophenyl)-4-(1-(5-iodopyrimidin-2-yl)piperidin-4-yloxy)-6-oxo-1,6-dihydropyridazine-3-carbonitrile for 4-(1-(5-iodopyrimidin-2-yl)piperidin-4-yloxy)-1-(4-(methylsulfonyl)phenyl)-6-oxo-1,6-dihydropyridazine-3-carbonitrile (example 48). $^1$H NMR (400 MHz, CDCl$_3$) δ ppm 1.78-2.31 (m, 4H) 3.09 (s, 3H) 3.78-4.34 (m, 4H) 4.54- 4.97 (m, 1H) 6.35 (s, 1H) 7.84 (d, J=8.35 Hz, 2H) 8.08 (d, J=8.79 Hz, 2H) 8.51 (s, 2H). MS (ESI) 521 (M+H).

Example 50

6-(Hydroxymethyl)-5-(1-(5-chloropyrimidin-2-yl) piperidin-4-yloxy)-2-(4-(methylsulfonyl)phenyl) pyridazin-3(2H)-one

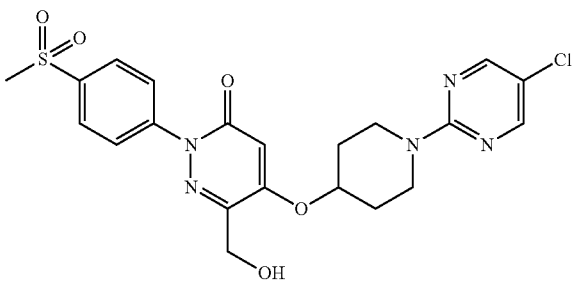 [SMILES: CS(=O)(=O)c1ccc(-n2nc(CO)c(OC3CCN(c4ncc(Cl)cn4)CC3)cc2=O)cc1]

Step A. Preparation of tert-butyl 4-(3-(hydroxymethyl)-1-(4-(methylsulfonyl)phenyl)-6-oxo-1,6-dihydropyridazin-4-yloxy)piperidine-1-carboxylate To a stirring solution of methyl 4-(1-(tert-butoxycarbonyl)piperidin-4-yloxy)-1-(4-(methylsulfonyl)phenyl)-6-oxo-1,6-dihydropyridazine-3-carboxylate (example 18) (254 mg, 0.5 mmol) in THF/MeOH (1:1) (10 mL) at room temperature under argon was added NaBH$_4$ (95 mg, 2.5 mmol) at 0° C. in an ice bath under argon carefully. The reaction mixture was allowed to warm to room temperature gradually and stirred overnight. EtOAc (20 mL) and water (20 mL) were added to the reaction mixture. Layers were separated. Organic layer were washed with water (15 mL), and brine (15 mL). Organic phase was dried (MgSO$_4$), filtered and concentrated. The crude product was dissolved in a small amount of DCM (~2 ml) and loaded onto a 40 g ISCO silica gel column which was eluted with a 20 min gradient from 20% to 100% EtOAc/Hexanes. 230 mg (95%) of tert-butyl 4-(3-(hydroxymethyl)-1-(4-(methylsulfonyl)phenyl)-6-oxo-1,6-dihydropyridazin-4-yloxy)piperidine-1-carboxylate was obtained as a white solid MS (ESI) 434 (M+H-tBu).

Step B. Preparation of 6-(hydroxymethyl)-2-(4-(methylsulfonyl)phenyl)-5-(piperidin-4-yloxy)pyridazin-3(2H)-one, HCl salt To a stirring solution of tert-butyl 4-(3-(hydroxymethyl)-1-(4-(methylsulfonyl)phenyl)-6-oxo-1,6-dihydropyridazin-4-yloxy)piperidine-1-carboxylate (200 mg, 0.417 mmol) in DCM (3 mL) at room temperature under argon was added 4 M HCl in dioxane (0.521 mL, 2.085 mmol). The reaction mixture was stirred at room temperature overnight. Et$_2$O (10 mL) was added to the reaction mixture. The solid product was collected by filtration and further washed with ether (2 mL×2). After drying under vacuum for 2 hours, 171 mg (100%) of 6-(hydroxymethyl)-2-(4-(methylsulfonyl)phenyl)-5-(piperidin-4-yloxy)pyridazin-3(2H)-one HCl salt was obtained as an off-white solid. MS (ESI) 380 (M+H).

Step C. Example 50

To a stirring solution of 6-(hydroxymethyl)-2-(4-(methylsulfonyl)phenyl)-5-(piperidin-4-yloxy)pyridazin-3(2H)-one HCl (18.97 mg, 0.05 mmol) in NMP (2 mL) at room temperature under argon was added DIPEA (19.4 mg, 0.150 mmol) and 5-chloro-2-iodopyrimidine (24 mg, 0.1.0 mmol). The resulting reaction mixture was heated at 100° C. under argon overnight. 15 mL of EtOAc was added to the reaction mixture. The reaction mixture was washed with water (15 mL), and brine (15 mL). Organic phase was dried (MgSO$_4$), filtered and concentrated. The crude product was dissolved in a small amount of DCM (~2 ml) and loaded onto a 24 g ISCO silica gel column which was eluted with a 20 min gradient from 20% to 100% EtOAc/Hexanes. 16 mg (62%) of 5-(1-(5-chloropyrimidin-2-yl)piperidin-4-yloxy)-6-(hydroxymethyl)-2-(4-(methylsulfonyl)phenyl)pyridazin-3(2H)-one was obtained as a tan solid. $^1$H NMR (400 MHz, CDCl$_3$) δ ppm 1.73-1.95 (m, 2H) 1.98-2.22 (m, 2H) 2.58 (s, 1H) 2.96-3.16 (m, 3H) 3.61-3.83 (m, 2H) 3.96-4.17 (m, 2H) 4.48-4.82 (m, 3H) 6.30 (s, 1H) 7.88 (d, J=8.79 Hz, 2H) 8.04 (d, J=8.35 Hz, 2H) 8.24 (s, 2H). MS (ESI) 492 (M+H).

Example 51

6-(Hydroxymethyl)-5-(1-(5-iodopyrimidin-2-yl)piperidin-4-yloxy)-2-(4-(methylsulfonyl)phenyl)pyridazin-3(2H)-one

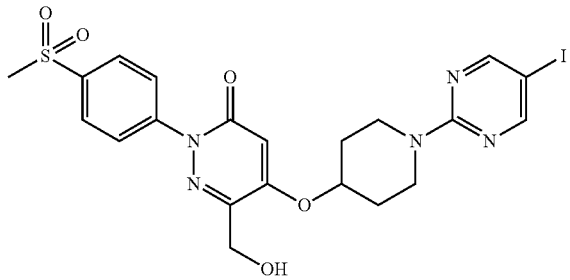 [SMILES: CS(=O)(=O)c1ccc(-n2nc(CO)c(OC3CCN(c4ncc(I)cn4)CC3)cc2=O)cc1]

Example 51 was prepared in 73% yield according to procedures described in Example 50 (Step C) substituting 5-chloro-2-iodopyrimidine for 2-chloro-5-iodopyrimidine. $^1$H NMR (400 MHz, CDCl$_3$) δ ppm 1.73-1.93 (m, 2H) 1.98-2.21 (m, 2H) 2.58 (s, 1H) 3.07 (s, 3H) 3.61-3.83 (m, 2H) 3.91-4.21 (m, 2H) 4.47-4.93 (m, 3H) 6.30 (s, 1H) 7.88 (d, J=8.79 Hz, 2H) 8.04 (d, J=8.79 Hz, 2H) 8.40 (s, 2H). MS (ESI) 584 (M+H).

Example 52

4-(1-(5-Cyanopyrimidin-2-yl)piperidin-4-yloxy)-1-(4-(methylsulfonyl)phenyl)-6-oxo-1,6-dihydropyridazine-3-carbonitrile

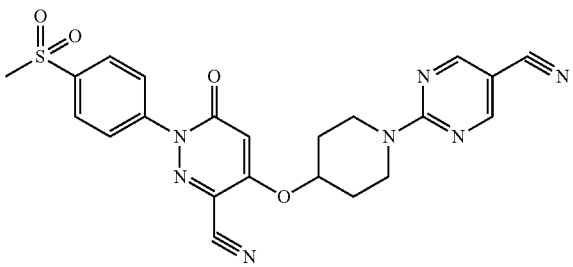 [SMILES: CS(=O)(=O)c1ccc(-n2nc(C#N)c(OC3CCN(c4ncc(C#N)cn4)CC3)cc2=O)cc1]

Step A. Preparation of 2-chloropyrimidine-5-carbonitrile

To a stirring solution of 2-aminopyrimidine-5-carbonitrile (1.0 g, 8.33 mmol) in CH$_3$CN (15 ml) at room temperature under argon was added copper (II) chloride (1.679 g, 12.5 mmol) and tert-butyl nitrite (1.288 g, 12.5 mmol). The reaction mixture was placed in a preheated oil bath (60° C.) under Argon. The reaction mixture was cooled to room temperature and 20 ml of ether was added. The resulting insoluble material was filtered and the filtrate was concentrated. The crude product was dissolved in a small amount of DCM (~2 ml) and loaded onto a 40 g ISCO silica gel column which was eluted with a 20 min gradient from 0% to 100% EtOAc/Hexanes. 723 mg (61%) of 2-chloropyrimidine-5-carbonitrile was obtained as a tan solid. $^1$H NMR (400 MHz, CDCl$_3$) δ ppm 8.90 (s, 2H).

Step B. Example 52

Example 52 was prepared in 60% yield according to procedures described in Example 32 (Step B) substituting 5-chloro-2-iodopyrimidine for 2-chloropyrimidine-5-carbonitrile. $^1$H NMR (400 MHz, CDCl$_3$) δ ppm 1.89-2.20 (m, 4H) 3.09 (s, 3H) 4.00-4.10 (m, 2H) 4.10-4.20 (m, 2H) 4.71-5.07 (m, 1H) 6.34 (s, 1H) 7.84 (d, J=8.79 Hz, 2H) 8.08 (d, J=8.79 Hz, 2H) 8.52 (s, 2H). MS (ESI) 478 (M+H).

Example 53

1-(4-Bromo-3-fluorophenyl)-4-(1-(5-chloropyrimidin-2-yl)piperidin-4-yloxy)-6-oxo-1,6-dihydropyridazine-3-carbonitrile

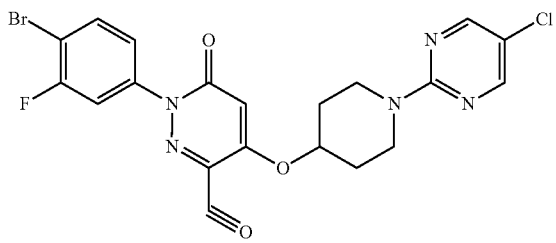

Step A. Preparation of 1-(4-bromo-3-fluorophenyl)-6-oxo-4-(piperidin-4-yloxy)-1,6-dihydropyridazine-3-carbonitrile, HCl salt To a stirring solution of tert-butyl 4-(1-(4-bromo-3-fluorophenyl)-3-cyano-6-oxo-1,6-dihydropyridazin-4-yloxy)piperidine-1-carboxylate (493 mg, 1.0 mmol) in DCM (5 mL) at room temperature under argon was added 4 M HCl in dioxane (1.25 mL, 5.0 mmol). The reaction mixture was stirred at room temperature overnight. Et$_2$O (10 mL) was added to the reaction mixture. The solid product was collected by filtration and further washed with ether (2 mL×2). After drying under vacuum for 2 hours, 411 mg (100%) of 1-(4-bromo-3-fluorophenyl)-6-oxo-4-(piperidin-4-yloxy)-1,6-dihydropyridazine-3-carbonitrile HCl salt was obtained as an off-white solid. MS (ESI) 393 (M+H).

Step B. Example 53

Example 53 was prepared in 87% yield according to procedures described in Example 47 (Step B) substituting 1-(4-

(methylsulfonyl)phenyl)-6-oxo-4-(piperidin-4-yloxy)-1,6-dihydropyridazine-3-carbonitrile HCl for 1-(4-bromo-3-fluorophenyl)-6-oxo-4-(piperidin-4-yloxy)-1,6-dihydropyridazine-3-carbonitrile HCl salt. $^1$H NMR (400 MHz, CDCl$_3$) δ ppm 1.85-2.01 (m, 2H) 2.00-2.13 (m, 2H) 3.48 (s, 1H) 3.72-3.94 (m, 2H) 3.96-4.21 (m, 2H) 4.48-4.94 (m, 1H) 6.31 (s, 1H) 7.32 (d, J=8.79 Hz, 1H) 7.45 (dd, J=9.01, 2.42 Hz, 1H) 7.62-7.80 (m, 1H) 8.24 (s, 2H). MS (ESI) 507 (M+H).

Example 54

1-(4-Bromo-2-fluorophenyl)-4-(1-(5-chloropyrimidin-2-yl)piperidin-4-yloxy)-6-oxo-1,6-dihydropyridazine-3-carbonitrile

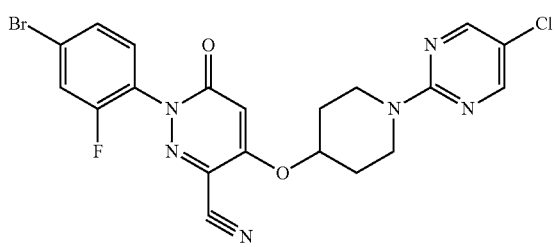 [SMILES: N#Cc1nn(-c2ccc(Br)cc2F)c(=O)cc1OC1CCN(c2ncc(Cl)cn2)CC1]

Step A. Preparation of 1-(4-bromo-2-fluorophenyl)-6-oxo-4-(piperidin-4-yloxy)-1,6-dihydropyridazine-3-carbonitrile, HCl salt To a stirring solution of tert-butyl 4-(1-(4-bromo-2-fluorophenyl)-3-cyano-6-oxo-1,6-dihydropyridazin-4-yloxy)piperidine-1-carboxylate (493 mg, 1.0 mmol) in DCM (5 mL) at room temperature under argon was added 4 M HCl in dioxane (1.25 mL, 5.0 mmol). The reaction mixture was stirred at room temperature overnight. Et$_2$O (10 mL) was added to the reaction mixture. The solid product was collected by filtration and further washed with ether (2 mL×2). After drying under vacuum for 2 hours, 334 mg (85%) of 1-(4-bromo-2-fluorophenyl)-6-oxo-4-(piperidin-4-yloxy)-1,6-dihydropyridazine-3-carbonitrile HCl salt was obtained as an off-white solid. MS (ESI) 393 (M+H).

Step B. Example 54

Example 54 was prepared in 91% yield according to procedures described in Example 47 (Step B) substituting 1-(4-(methylsulfonyl)phenyl)-6-oxo-4-(piperidin-4-yloxy)-1,6-dihydropyridazine-3-carbonitrile HCl for 1-(4-bromo-2-fluorophenyl)-6-oxo-4-(piperidin-4-yloxy)-1,6-dihydropyridazine-3-carbonitrile HCl salt. $^1$H NMR (400 MHz, CDCl$_3$) δ ppm 1.79-2.20 (m, 4H) 3.72-3.95 (m, 2H) 3.95-4.20 (m, 2H) 4.48-4.90 (m, 1H) 6.31 (s, 1H) 7.26-7.31 (m, 1H) 7.44 (d, J=9.23 Hz, 2H) 8.24 (s, 2H). MS (ESI) 507 (M+H).

Example 55 tert-Butyl 4-(1-(4-cyano-3-fluorophenyl)-3-(hydroxymethyl)-6-oxo-1,6-dihydropyridazin-4-yloxy)piperidine-1-carboxylate

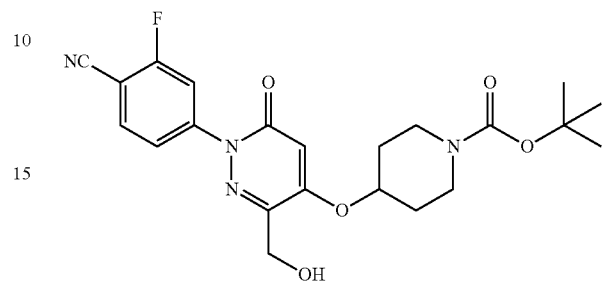

To a stirring solution of methyl 4-(1-(tert-butoxycarbonyl)piperidin-4-yloxy)-1-(4-cyano-3-fluorophenyl)-6-oxo-1,6-dihydropyridazine-3-carboxylate (27.2 mg, 0.1 mmol) in THF/MeOH (1:1) (3 mL) at room temperature under argon was added NaBH$_4$ (18.9 mg, 0.5 mmol) at 0° C. in an ice bath under argon carefully. The reaction mixture was allowed to warm to room temperature gradually and stirred overnight. EtOAc (20 mL) and water (20 mL) were added to the reaction mixture. Layers were separated. Organic layer were washed with water (15 mL), and brine (15 mL). Organic phase was dried (MgSO$_4$), filtered and concentrated. The crude product was dissolved in a small amount of DCM (~2 ml) and loaded onto a 40 g ISCO silica gel column which was eluted with a 20 min gradient from 20% to 100% EtOAc/Hexanes. 37 mg (82%) of tert-butyl 4-(1-(4-cyano-3-fluorophenyl)-3-(hydroxymethyl)-6-oxo-1,6-dihydropyridazin-4-yloxy)piperidine-1-carboxylate was obtained as a white solid. $^1$H NMR (400 MHz, CDCl$_3$) δ ppm 1.39-1.53 (m, 9H) 1.68-1.88 (m, 2H) 1.88-2.09 (m, 2H) 2.51 (t, J=5.93 Hz, 1H) 3.20-3.49 (m, 2H) 3.54-3.76 (m, 2H) 4.43-4.63 (m, 1H) 4.69 (d, J=5.71 Hz, 2H) 6.23 (s, 1H) 7.53-7.85 (m, 3H). MS (ESI) 389 (M+H-tBu).

Example 56 tert-Butyl 4-(3-cyano-1-(4-nitrophenyl)-6-oxo-1,6-dihydropyridazin-4-yloxy)piperidine-1-carboxylate

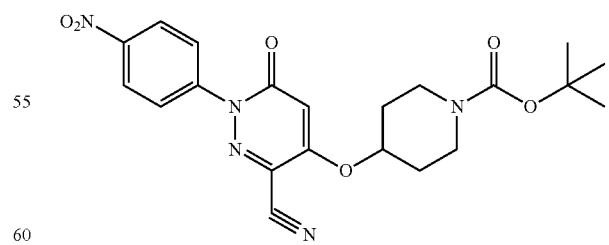

Step A. Preparation of 4-nitrobenzenediazonium

4-Nitrobenzenediazonium was prepared in 100% yield according to procedures described in Example 18 (Step A)

substituting 4-(methylsulfonyl)aniline for 4-nitroaniline. The reaction mixture was used directly to next step.

Step B. Preparation of (E)-dimethyl 2-(2-(4-nitrophenyl)hydrazono)-3-oxopentanedioate (E)-Dimethyl 2-(2-(4-nitrophenyl)hydrazono)-3-oxopentanedioate was prepared in 94% yield according to procedures described in Example 18 (Step B) substituting 4-(methylsulfonyl)benzenediazonium for 4-Nitrobenzenediazonium. MS (ESI) 324 (M+H).

Step C. Preparation of methyl 4-hydroxy-1-(4-nitrophenyl)-6-oxo-1,6-dihydropyridazine-3-carboxylate Methyl 4-hydroxy-1-(4-nitrophenyl)-6-oxo-1,6-dihydropyridazine-3-carboxylate was prepared in 48% yield according to procedures described in Example 18 (Step C) substituting (E)-dimethyl 2-(2-(4-(methylsulfonyl)phenyl)hydrazono)-3-oxopentanedioate for (E)-Dimethyl 2-(2-(4-nitrophenyl)hydrazono)-3-oxopentanedioate. MS (ESI) 292 (M+H).

Step D. Preparation of methyl 4-(1-(tert-butoxycarbonyl)piperidin-4-yloxy)-1-(4-nitrophenyl)-6-oxo-1,6-dihydropyridazine-3-carboxylate Methyl 4-(1-(tert-butoxycarbonyl)piperidin-4-yloxy)-1-(4-nitrophenyl)-6-oxo-1,6-dihydropyridazine-3-carboxylate was prepared in 67% yield according to procedures described in Example 14 substituting methyl 1-(3,4-dichlorophenyl)-4-hydroxy-6-oxo-1,6-dihydropyridazine-3-carboxylate for Methyl 4-hydroxy-1-(4-nitrophenyl)-6-oxo-1,6-dihydropyridazine-3-carboxylate with MS (4A) in the reaction mixture. $^1$H NMR (400 MHz, CDCl$_3$) δ ppm 1.39-1.52 (m, 9H) 1.75-2.21 (m, 4H) 3.55 (d, J=3.30 Hz, 4H) 3.94 (s, 3H) 4.38-4.94 (m, 1H) 6.28 (s, 1H) 7.88 (d, J=8.79 Hz, 2H) 8.32 (d, J=8.79 Hz, 2H). MS (ESI) 419 (M+H-tBu).

Step E. Preparation of tert-butyl 4-(3-carbamoyl-1-(4-nitrophenyl)-6-oxo-1,6-dihydropyridazin-4-yloxy)piperidine-1-carboxylate tert-Butyl 4-(3-carbamoyl-1-(4-nitrophenyl)-6-oxo-1,6-dihydropyridazin-4-yloxy)piperidine-1-carboxylate was prepared in 100% yield according to procedures described in Example 31 (Step A) substituting methyl 4-(1-(tert-butoxycarbonyl)piperidin-4-yloxy)-1-(4-(methylsulfonyl)phenyl)-6-oxo-1,6-dihydropyridazine-3-carboxylate for Methyl 4-(1-(tert-butoxycarbonyl)piperidin-4-yloxy)-1-(4-nitrophenyl)-6-oxo-1,6-dihydropyridazine-3-carboxylate. MS (ESI) 404 (M+H).

Step F. Example 56

Example 56 was prepared in 93% yield according to procedures described in Example 31 (Step B) substituting tert-butyl 4-(3-carbamoyl-1-(4-(methylsulfonyl)phenyl)-6-oxo-1,6-dihydropyridazin-4-yloxy)piperidine-1-carboxylate for tert-Butyl 4-(3-carbamoyl-1-(4-nitrophenyl)-6-oxo-1,6-dihydropyridazin-4-yloxy)piperidine-1-carboxylate. $^1$H NMR (400 MHz, CDCl$_3$) δ ppm 1.44-1.50 (m, 9H) 1.76-1.94 (m, 2H) 1.94-2.18 (m, 2H) 3.28-3.55 (m, 2H) 3.58-3.95 (m, 2H) 4.36-4.89 (m, 1H) 6.29 (s, 1H) 7.84 (d, J=9.34 Hz, 2H) 8.35 (d, J=8.79 Hz, 2H). MS (ESI) 386 (M+H-tBu).

Example 57

4-(1-(5-(Difluoromethoxy)pyrimidin-2-yl)piperidin-4-yloxy)-1-(4-(methylsulfonyl)phenyl)-6-oxo-1,6-dihydropyridazine-3-carbonitrile

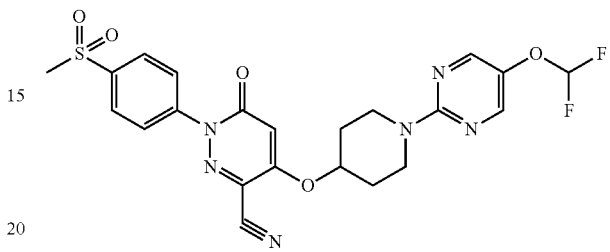

Step A. Preparation of 2-(methylthio)-5-(4,4,5,5-tetramethyl-1,3,2-dioxaborolan-2-yl)pyrimidine To a stirring solution of 5-bromo-2-(methylthio)pyrimidine (950 mg, 4.63 mmol) in DMF (5 mL) at room temperature under argon was added 4,4,4',4',5,5,5',5'-octamethyl-2,2'-bi(1,3,2-dioxaborolane) (1.77 g, 6.95 mmol), potassium acetate (1.36 g, 13.90 mmol), and diacetoxypalladium (104 mg, 0.463 mol). The resulting suspension was degassed with argon for 15 min and heated at 85° C. overnight. The reaction was cooled to room temperature. EtOAc (10 mL) was added to the reaction mixture, which was washed with brine (15 mL×3). Organic phase was dried (MgSO$_4$), filtered and concentrated. The crude product was used directly to next step.

Step B. Preparation of 2-(methylthio)pyrimidin-5-ol

To a stirring solution of 2-(methylthio)-5-(4,4,5,5-tetramethyl-1,3,2-dioxaborolan-2-yl)pyrimidine (from step A) (1.167 g, 4.63 mmol) in THF/H$_2$O (20 mL 1:1) at room temperature under argon was added sodium perborate tetrahydrate (2.137 g, 13.9 mmol). The reaction mixture was stirred at room temperature overnight. The reaction was cooled to room temperature. EtOAc (10 mL) was added to the reaction mixture, which was washed with brine (15 mL×3). Organic phase was dried (MgSO$_4$), filtered and concentrated. The crude product was very insoluble, therefore it was used directly to next step. MS (ESI) 143 (M+H).

Step C. Preparation of 5-(difluoromethoxy)-2-(methylthio)pyrimidine

To a stirring solution of 2-(methylthio)pyrimidin-5-ol (from step B) (71 mg, 0.50 mmol) in CH$_3$CN (2.5 mL) and water (2.5 mL) at room temperature under argon was added K$_2$CO$_3$ (0.69 g, 5.0 mmol) and followed by 2-chloro-2,2-difluoro-1-phenylethanone (286 mg, 1.5 mmol). The reaction tube was sealed and heated at 80° C. for 5 hours. The reaction was cooled to room temperature. EtOAc (10 mL) was added to the reaction mixture, which was washed with brine (15 mL×3). Organic phase was dried (MgSO$_4$), filtered and concentrated. The crude product was dissolved in a small amount of DCM (~2 ml) and loaded onto a 40 g ISCO silica gel column which was eluted with a 20 min gradient from 0% to 100% EtOAc/Hexanes. 23 mg (23% for three steps) of 5-(difluoromethoxy)-2-(methylthio)pyrimidine was obtained as an off white solid. MS (ESI) 193 (M+H).

Step D. Preparation of 5-(difluoromethoxy)-2-(methylsulfonyl)pyrimidine

To a stirring solution of 5-(difluoromethoxy)-2-(methylthio)pyrimidine (19 mg, 0.10 mmol) in DCM (3 mL) at room temperature under argon was added MCPBA (74 mg, 0.30 mmol). The reaction mixture was stirred at room temperature for 1 hour. Solvent was removed in vacuo under reduced pressure and crude product was used directly to next step. MS (ESI) 225 (M+H).

Step E. Example 57

To a stirring solution of 1-(4-(methylsulfonyl)phenyl)-6-oxo-4-(piperidin-4-yloxy)-1,6-dihydropyridazine-3-carbonitrile HCl (example 47 step A) (41 mg, 0.10 mmol) in NMP (3 mL) at room temperature under argon was added DIPEA (38.8 mg, 0.30 mmol) and 5-(difluoromethoxy)-2-(methylsulfonyl)pyrimidine (22.4 mg, 0.1.0 mmol). The resulting reaction mixture was heated at 100° C. under argon overnight. After cooling to room temperature, 15 mL of EtOAc was added to the reaction mixture. The reaction mixture was washed with water (15 mL), and brine (15 mL). Organic phase was dried (MgSO$_4$), filtered and concentrated. The crude product was dissolved in a small amount of DCM (~3 ml) and loaded onto a 24 g ISCO silica gel column which was eluted with a 20 min gradient from 20% to 100% EtOAc/Hexanes. 8 mg (15% for two steps) of 4-(1-(5-(difluoromethoxy)pyrimidin-2-yl)piperidin-4-yloxy)-1-(4-(methylsulfonyl)phenyl)-6-oxo-1,6-dihydropyridazine-3-carbonitrile was obtained as a tan solid $^1$H NMR (400 MHz, CDCl$_3$) δ ppm 1.75-2.27 (m, 4H) 3.08 (s, 3H) 3.66-3.97 (m, 2H) 3.97-4.24 (m, 2H) 4.54-4.95 (m, 1H) 6.34 (s, 1H) 7.84 (d, J=8.79 Hz, 2H) 8.07 (d, J=8.79 Hz, 2H) 8.24 (s, 2H). MS (ESI) 519 (M+H).

Example 58

Isopropyl 4-(3-cyano-1-(4-cyano-3-fluorophenyl)-6-oxo-1,6-dihydropyridazin-4-yloxy)piperidine-1-carboxylate

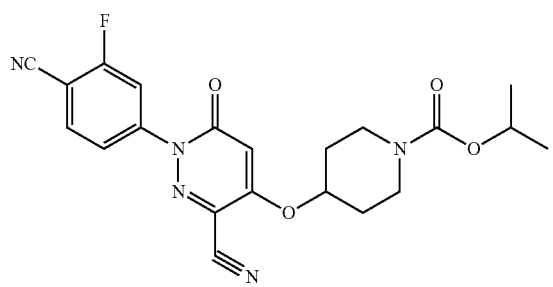 [SMILES: CC(C)OC(=O)N1CCC(Oc2cc(=O)n(-c3ccc(C#N)c(F)c3)nc2C#N)CC1]

To a stirring solution of 1-(4-cyano-3-fluorophenyl)-6-oxo-4-(piperidin-4-yloxy)-1,6-dihydropyridazine-3-carbonitrile HCl salt (Example 36, step A) (19 mg, 0.05 mmol) in DCM (3 mL) at room temperature under argon was added TEA (0.014 mL, 0.10 mmol) and isopropyl carbonochloridate (12 mg, 0.10 mmol). The reaction mixture was stirred at room temperature overnight. Solvent was removed in vacuo and the crude product was dissolved in a small amount of DCM (~2 ml) and loaded onto a 40 g ISCO silica gel column which was eluted with a 20 min gradient from 0% to 100% EtOAc/Hexanes. 15 mg (43%) of isopropyl 4-(3-cyano-1-(4-cyano-3-fluorophenyl)-6-oxo-1,6-dihydropyridazin-4-yloxy)piperidine-1-carboxylate was obtained as white solid. $^1$H NMR (400 MHz, CDCl$_3$) δ ppm 7.72-7.81 (1H, m), 7.56-7.72 (2H, m), 6.30 (1H, s), 4.82-5.04 (1H, m, J=6.6, 6.3, 6.2, 6.2 Hz), 4.65 (1H, ddd, J=7.0, 3.4, 3.3 Hz), 3.65-3.84 (2H, m), 3.37-3.61 (2H, m), 1.96-2.12 (2H, m), 1.81-1.96 (2H, m), 1.13-1.33 (6H, m). MS (ESI) 426 (M+H).

Example 59

Isopropyl 4-(3-cyano-1-(4-(methylsulfonyl)phenyl)-6-oxo-1,6-dihydropyridazin-4-yloxy)piperidine-1-carboxylate

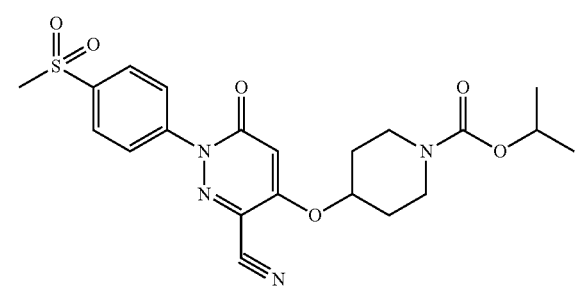 [SMILES: CC(C)OC(=O)N1CCC(Oc2cc(=O)n(-c3ccc(S(C)(=O)=O)cc3)nc2C#N)CC1]

Example 59 was prepared in 47% yield according to procedures described in Example 50 (Step C) substituting 1-(4-cyano-3-fluorophenyl)-6-oxo-4-(piperidin-4-yloxy)-1,6-dihydropyridazine-3-carbonitrile HCl salt for 1-(4-(methylsulfonyl)phenyl)-6-oxo-4-(piperidin-4-yloxy)-1,6-dihydropyridazine-3-carbonitrile HCl (example 47 step A). $^1$H NMR (400 MHz, CDCl$_3$) δ ppm 8.09 (2H, d, J=8.8 Hz), 7.85 (2H, d, J=8.8 Hz), 6.32 (1H, s), 4.96 (1H, t, J=6.3 Hz), 4.49-4.78 (1H, m), 3.60-3.93 (2H, m), 3.40-3.64 (2H, m), 3.10 (3H, s), 1.77-2.12 (4H, m), 1.28 (6H, d, J=6.0 Hz). MS (ESI) 461 (M+H).

Example 60

Preparation of trans-tert-butyl 4-(5-chloro-1-(4-cyano-3-fluorophenyl)-2-oxo-1,2-dihydropyridin-4-yloxy)-3-methylpiperidine-1-carboxylate

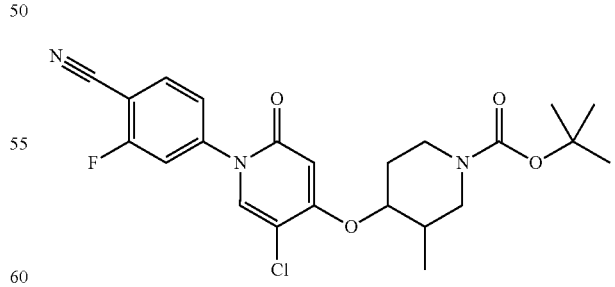

Step A. Preparation of 4-(5-chloro-4-hydroxy-2-oxopyridin-1(2H)-yl)-2-fluorobenzonitrile A mixture of 2-fluoro-4-iodobenzonitrile (4000 mg, 16.19 mmol), 5-chloro-4-hydroxypyridin-2(1H)-one (2357 mg, 16.19 mmol), 4,7-dimethoxy-1,10-phenanthroline (778 mg, 3.24 mmol), copper(I) iodide (617 mg, 3.24 mmol) and potassium carbonate (4476 mg, 32.4 mmol) in DMSO (40 mL) was stirred at 140° C. under N$_2$ for 3 hrs. After cooling to room temperature, the reaction mixture was diluted with H$_2$O (50 mL) and 1N HCl was added to adjust the pH to ~2 (pH paper). The resulting mixture was extracted with EtOAc (400 mL, 2×). The combined extracts were dried (Na$_2$SO$_4$) and evaporated under reduced pressure to give black oil. The residue was purified by flash chromatography on silica gel (0-7% MeOH/CH$_2$Cl$_2$) to give brown oil (3.2 g, 43.3%). MS (ESI) 265 (M+H).

Step B. Example 60

To a mixture of 4-(5-chloro-4-hydroxy-2-oxopyridin-1 (2H)-yl)-2-fluorobenzonitrile (193 mg, 0.729 mmol), tert-butyl 4-hydroxy-3-methylpiperidine-1-carboxylate (173 mg, 0.802 mmol) and triphenylphosphine (230 mg, 0.875 mmol) in THF (2.0 mL) was added DEAD (0.129 mL, 0.875 mmol). The resulting mixture was stirred at room temperature overnight and then evaporated under reduced pressure. The residue was purified by flash chromatography on silica gel (0-100% EtOAc/hexane) to yield trans-tert-butyl 4-(5-chloro-1-(4-cyano-3-fluorophenyl)-2-oxo-1,2-dihydropyridin-4-yloxy)-3-methylpiperidine-1-carboxylate (183.5 mg, 50.1%) as an orange solid. $^1$H NMR (400 MHz, DMSO): δ ppm 7.99-8.15 (m, 2H), 7.80 (dd, J=10.55, 1.76 Hz, 1H), 7.55 (dd, J=8.35, 1.76 Hz, 1H), 6.21 (s, 1H), 4.67-4.84 (m, 1H), 3.52 (app br s, 2H), 3.18 (app br s, 2H), 1.99 (app br s, 1H), 1.82 (app br s, 1H), 1.62-1.73 (m, 1H), 1.40 (s, 9H), 0.90 (d, J=7.03 Hz, 3H). MS (ESI) 406 (M−56+H).

Example 61

Preparation of cis- and trans-isomers of 4-(5-chloro-4-(1-(5-cyclopropylpyrimidin-2-yl)-3-methylpiperidin-4-yloxy)-2-oxopyridin-1(2H)-yl)-2-fluorobenzonitrile

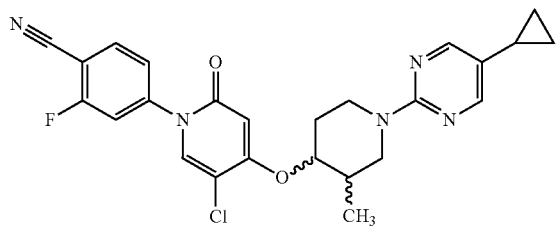 [SMILES: CC1CN(c2ncc(C3CC3)cn2)CCC1Oc1cc(=O)n(-c2ccc(C#N)c(F)c2)cc1Cl]

Step A. Preparation of 4-(5-chloro-4-(3-methylpiperidin-4-yloxy)-2-oxopyridin-1(2H)-yl)-2-fluorobenzonitrile hydrochloride To a solution of trans-tert-butyl 4-(5-chloro-1-(4-cyano-3-fluorophenyl)-2-oxo-1,2-dihydropyridin-4-yloxy)-3-methylpiperidine-1-carboxylate (200 mg, 0.433 mmol) in MeOH (1.0 mL) at room temperature was added hydrochloric acid (2.5 mL, 10.00 mmol, 4.0 M in dioxane). The reaction mixture was stirred for 30 min and then evaporated under reduced pressure. The residue was co-evaporated with ethanol (2×) to give 198 mg of the title compound as an orange solid. This material was used in the next step without further purification. MS (ESI) 362 (M+H).

Step B. Example 61

A mixture of 4-(5-chloro-4-(3-methylpiperidin-4-yloxy)-2-oxopyridin-1(2H)-yl)-2-fluorobenzonitrile hydrochloride (159 mg, 0.399 mmol), 2-chloro-5-cyclopropylpyrimidine (67.9 mg, 0.439 mmol) and potassium carbonate (221 mg, 1.597 mmol) in DMSO (1.5 mL) was heated at 90-110° C. for 40 hrs and then additional potassium carbonate (110 mg, 0.788 mmol) was added. The resulting mixture was continuously heated at 100° C. overnight and then partitioned between EtOAc and water. The aqueous layer was extracted further with EtOAc (3×). The combined organic extracts were washed with water and brine, dried (Na$_2$SO$_4$) and evaporated under reduced pressure. The residue was purified by flash chromatography on silica gel (0-100% EtOAc/hexane) to yield cis-4-(5-chloro-4-(1-(5-cyclopropylpyrimidin-2-yl)-3-methylpiperidin-4-yloxy)-2-oxopyridin-1(2H)-yl)-2-fluorobenzonitrile (10.2 mg, 5%, top spot on TLC plate) as a light yellow solid and to yield trans-4-(5-chloro-4-(1-(5-cyclopropylpyrimidin-2-yl)-3-methylpiperidin-4-yloxy)-2-oxopyridin-1(2H)-yl)-2-fluorobenzonitrile (34.4 mg, 15%, bottom spot on TLC plate) as a light yellow solid. Cis-isomers: $^1$H NMR (500 MHz, CDCl$_3$) δ ppm 8.13 (s, 2H), 7.76 (t, J=7.42 Hz, 1H), 7.36-7.41 (m, 2H), 7.33 (d, J=8.25 Hz, 1H), 6.04 (s, 1H), 4.48-4.62 (m, 2H), 4.16 (m, 2H), 3.85 Hz, 1H), 3.19-3.29 (m, 1H), 2.98 (dd, J=13.75, 9.90 Hz, 1H), 2.18-2.30 (m, 1H), 2.01-2.12 (m, 1H), 1.63-1.77 (m, 2H), 1.08 (d, J=6.60 Hz, 3H), 0.89-0.95 (m, 2H), 0.57-0.62 (m, 2H). MS (ESI) 480 (M+H). Trans-isomers: $^1$H NMR (500 MHz, CDCl$_3$) δ ppm 8.13 (s, 2H), 7.76 (t, J=7.42 Hz, 1H), 7.36-7.43 (m, 2H), 7.33 (d, J=8.25 Hz, 1H), 6.03 (s, 1H), 4.58 (app br s, 1H), 4.29-4.42 (m, 2H), 3.28-3.40 (m, 2H), 2.01-2.17 (m, 2H), 1.77-1.89 (m, 1H), 1.68-1.77 (m, 1H), 0.99-1.12 (m, 3H), 0.85-0.97 (m, 2H), 0.51-0.63 (m, 2H). MS (ESI) 480 (M+H).

Assay(s) for GPR119 G Protein-Coupled Receptor Activity

The in vitro modulation of recombinant human GPR119 was determined as follows.
HIT-T15 cAMP Assay
A HIT-T15 hamster insulinoma cell line was purchased from ATCC and grown in the medium recommended by ATCC (i.e., Growth Medium: F12K Medium (Invitrogen 21127-022; 10% D-horse Serum; and 2.5% FBS).
To conduct the cAMP assay, cells expressing a GPR119 receptor are plated on 96 well plates (e.g., BD Falcon: REF 353948, black side, clear bottom, TC surface) at a density of about 4.5×10$^4$ cells per well in growth medium and incubated overnight. Following incubation, the growth medium is removed from the wells followed by a single rinse with the assay buffer from the HITHUNTER® cAMP kit (100 μl/well). Following the rinse, 20 μl of assay buffer is added to each well followed by addition of 10 μl of a 3× concentration of compound working solution. The solution is then mixed well. The final concentration range of compound is from about 10$^{-5}$M to about 10$^{-11}$ M. The reaction is incubated at 37° C., in a 5% CO$_2$ for 1 hour. Following incubation, the cAMP concentration is determined using the HITHUNTER® cAMP kit according to the manufacturer's protocol.
Human Tet-Inducible cAMP Assay
Cell lines expressing GPR119 are generated using the Flp-In T-REx 293 tetracycline inducible gene expression system are cultured in culture medium comprising the following components: DMEM#11965, 10% FBS, 2 mM L-glutamine, 200 ug/ml Hygromycin B, and 15 ug/ml blasticidin.

For cAMP assays, cells are plated on 96 well plates (e.g., BD Falcon: REF 353948, black side, clear bottom, TC surface) at a density of about $4.5 \times 10^4$ cells per well in growth medium containing 1.0 ug/ml tetracycline (1.0 mg/ml stock). The cells are then incubated for 48 hours at 37° C.

Following the incubation, the growth medium is removed from the wells and the wells rinsed (once) with the assay buffer included in the HITHUNTER® cAMP kit (100 μl/well). Following the wash, 20 μl of assay buffer is added to each well, followed by addition of 10 μl of a 3× concentration compound working solution. The solution is then mixed. The final concentration range of compound is from about $10^{-5}$ M to about $10^{-11}$ M. The reagents are then incubated at 37° C. at 5% $CO_2$ for 1 hour.

The manufacturer's protocol may be followed for cAMP determination. The HITHUNTER® cAMP kit protocol is outlined for the HIT-T15 cAMP assays described above.

Compounds of the present invention were tested in the Human Tet-inducible cAMP assay described immediately above and the results shown in Table 1 below were obtained.

TABLE 1

| Example | hGPR119 $EC_{50}$ (nM) |
|---|---|
| 11 | 4603 |
| 16 | 3392 |
| 18 | 4010 |
| 26 | 5 |
| 31 | 83 |
| 34 | 3 |
| 38 | 8 |
| 42 | 107 |
| 45 | 95 |

Luciferase Assay

HEK 293 cells may be plated on poly-D-lysine treated 96-well BD black side/clear bottom plates at a density of about $3 \times 10^4$ cells/well in growth medium. The growth medium may comprise the following: D-MEM (Cat #12430) with high glucose and 10% fetal bovine serum.

Cells may be transfected with vectors comprising native or non-native GPR119 sequences using commercially available vectors (e.g., Stratagene) and transfection reagents. The standard manufacturer's protocols may be followed to transfect the cells. Following transfection, the transfection medium may be removed and assay medium added to the wells of the assay plates.

Once the assay plates are prepared, compound dilution plates may be made. To do so, make a first compound dilution plate using 10 mM of the compound of interest diluted to about 1 mM in DMSO. Then make 12 point half-log dilutions of the compounds (in DMSO) using an automated liquid handler. Next, make a second dilution plate by diluting the wells in the first plate ten fold (10×) using assay medium. Once the plates are complete, the highest dose is about 10 μM and the lowest dose is about 0.03 nM.

Once the dilution plates are complete, one can add about 10 μl of the 10× compound dilution to the assay plate containing the assay medium transiently transfected cells. Tap the plate to mix the reagents and incubate the plate overnight at 37° C., 95% $O_2$, and 5% $CO_2$ in an incubator.

Following incubation, a luciferase assay system may be used (e.g., STEADY-GLO® Luciferase Assay System from Promega) according to the manufacturer's instructions. Following completion of the reaction, immediately measure the readout of the assay using a top count luminometer.

Mouse Oral Glucose Tolerance Test

Twenty four (24) male C57BL/6J mice (8-10 weeks old, average weight 28 g) were randomized into 4 groups (1 mouse/cage) of 6 mice per group based on fed plasma glucose and body weight. Prior to initiating the study, mice were fasted overnight and the next morning they were weighed and placed in the experimental lab. After 30 min in the environment, the mice were bled via tail tip at −30 min and immediately given their first oral administration of vehicle (0.5% Methocel, 0.1% Tween 80 in water) or compound solutions (5 ml/kg). At time 0 the mice were bled and given 50% glucose (2 g/kg) to initiate the oral glucose tolerance test (oGTT). The mice were bled 30, 60 and 120 min after the glucose load. Blood samples were drawn into potassium EDTA, placed on ice during the study and subsequently centrifuged for 10 min at 3000 rpm at 4° C. Plasma samples were diluted 11-fold for glucose analysis in the COBAS MIRA® System (Roche Diagnostics). Area under the curve was calculated from the plasma glucose time course data using the trapezoid rule with fasting plasma glucose as the baseline (GraphPad Prism Software). The statistical significance of the changes in the glucose AUCs resulting from the different treatments was determined by one-way ANOVA followed by Dunnett's test using the vehicle group as the control (JMP software, release 5.1.2).

UTILITIES AND COMBINATIONS

A. Utilities

The compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of Formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR119 receptor agonists or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar); SGLT2 inhibitors (e.g., 3-(benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis)); 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, and denagliptin); glucagon-like peptide-1 (GLP-1) receptor agonists (e.g., Exenatide (Byetta), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DACTM); aldose reductase inhibitors (e.g., those disclosed in WO 99/26659); RXR agonists (e.g., reglitazar (JTT-501), 5-[[6-[(2-fluorophenyl)methoxy]-2-naphthalenyl]methyl]-2,4-thiazolidinedione (MCC-555), 5-[[3-(5,6,7,8-tetrahydro-3,5,5,8,8-pentamethyl-2-naphthalenyl)-4-(trifluoromethoxy)-phenyl]methylene]-2,4-thiazolidinedione (MX-6054), DRF2593, farglitazar, (±)-5-[(2,4-dioxothiazolidin-5-yl)methyl]-2-methoxy-N-[[(4-trifluoromethyl)phenyl]-methyl] benzamide (KRP-297), 6-[1-(5,6,7,8-tetrahydro-3,5,5,8,8-pentamethyl-2-naphthalenyl)cyclopropyl]-3-pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., methyl ester[4-[(2R)-2-[[(2R)-2-(3-chlorophenyl)-2-hydroxyethyl]amino]propyl]phenoxy]-acetic acid (BRL 35135), 2-[4-[(2S)-2-[[(2S)-2-(3-chlorophenyl)-2-hydroxyethyl]amino]propyl]phenoxy]-acetic acid (BRL 37344), 4-[(3R)-3-[bis[(2R)-2-hydroxy-2-phenylethyl]amino]butyl]-benzamide (Ro 16-8714), 2-[4-[2-[[(2S)-2-hydroxy-3-phenoxypropyl]amino]ethoxy]phenoxy]-N-(2-methoxyethyl)-acetamide (ICI D7114), 5-[(2R)-2-[[(2R)-2-(3-chlorophenyl)-2-hydroxyethyl]amino]propyl]-3-benzodioxole-2,2-dicarboxylic acid, disodium salt (CL 316, 243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386,398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-cyclohexadiene-1,4-dione (L-783281), TER17411, TER17529); gluconeogenesis inhibitors (e.g., GP3034); somatostatin analogs and antagonists; antilipolytic agents (e.g., nicotinic acid, acipimox, N-cyclohexyl-2'-O-methyl-adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (KaroBio)); glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-pyridinecarboxylic acid (GKA-50 AstraZeneca)); GPR119 agonists (e.g., 1,1-dimethylethyl ester 4-[[3-(4-pyridinyl)-1,2,4-oxadiazol-5-yl]methoxy]-1-piperidinecarboxylic acid (PSN-632408 OSI Prosidion)); GDIR agonists (e.g., APD668 (Arena)); GPR40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy) phenyl)-1H-benzo[d]imidazole).

Examples of suitable lipid lowering agents and anti-atherosclerotic agents for use in combination with the compounds of the present invention include one or more MTP/ApoB secretion inhibitors (e.g., dirlopatide, N-(2,2,2-trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid cotransporter inhibitors (e.g., compounds as disclosed in *Drugs of the Future*, 24:425-430 (1999); upregulators of LDL receptor activity (e.g., (3R)-3-[(13R)-β-hydroxy-10-oxotetradecyl]-5,7-dimethoxy-1(3H)-isobenzofuranone (Taisho Pharmaceutical Co. Ltd.) and (3α,4α,5α)-4-(2-propenyl)-cholestan-3-ol (Eli Lilly); bile acid sequestrants (e.g., WELCHOL®, COLESTID®, LoCholest and QUESTRAN®; and fibric acid derivatives, such as Atromid, LOPID® and Tricot); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl) sulfonyl]-4,5-dihydro-N'-methyl-4-phenyl-1H-pyrazole-1-carboximidamide (SLV 319), CP-945598 (Pfizer), Surinabant (SR-147778, Sanofi-Aventis), N-[(1S,2S)-3-(4-chlorophenyl)-2-(3-cyanophenyl)-1-methylpropyl]-2-methyl-2-{[5-(trifluoromethyl)pyridin-2-yl] oxy}propanamide (Merck) and those discussed in Hertzog, D. L., *Expert Opin. Ther. Patents*, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-benzenesulfonamide (L750355, Merck), or CP331648 (Pfizer,) or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buproprion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta[b][1,4]diazepino[6,7,1hi]indole], with lorcaserin hydrochloride being preferred); 5-HT6 receptor antagonists (Suven, Biovitrum, Epix), anti-epileptics topiramate (Johnson & Johnson) and zonisamide, a ciliary neurotrophic factor agonist (e.g., AXOKINE® (Regeneron); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer)); acetyl-CoA carboxylase (ACC) inhibitors (e.g., N-(4-(4-(4-isopropoxyphenoxy)phenyl)but-3-yn-2-yl)acetamide (A-80040, Abbott), (R)-anthracen-9-yl(3-(morpholine-4-carbonyl)-1,4'-bipiperidin-1'-yl)methanone (CP-640186, Pfizer)), SCD-1 inhibitors as described by Jiang et al., Diabetes, 53 (2004), (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH2 (Unigene)), NPY-Y4 agonists (7™ Pharma WO 2005/089786(A2,A3)-1), NPY-5 antagonists (e.g., NPY5RA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to ARICEPT®, razadyne, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

The compounds of Formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of Formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of Formula I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of Formula I into a vial, aseptically freeze-drying and sealing. For use, the contents of the vial are mixed with 2 mL of physiological saline, to produce an injectable preparation.

What is claimed is:
1. A compound of Formula I:

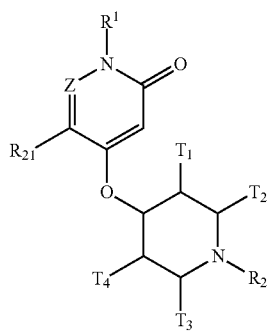

I or an enantiomer, a diastereomer, or a pharmaceutically acceptable salt thereof, wherein:

Z is N;

$R^1$ is aryl, arylalkyl or heteroaryl, any of which may be optionally substituted with one or more $R^6$'s;

$R^2$ is cycloalkyl, aryl, heteroaryl, heterocyclyl, —S(O)$_2$R$^5$, —C(=O)NR$^3$R$^5$, —C(=O)R$^5$ or —C(=O)OR$^5$, wherein the cycloalkyl, aryl, heteroaryl and heterocyclyl may each be optionally substituted with one or more $R^6$'s;

$R^3$ is hydrogen, alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl and heterocyclylalkyl may each contain 1-4 heteroatoms selected from N, O and S;

$R^5$ is alkyl, alkenyl, aryl, cycloalkyl, heteroaryl or heterocyclyl, each of which may be optionally substituted with one or more $R^6$'s;

$R^6$, at each occurrence, is independently selected from alkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —S(O)$_3$H, —P(O)$_3$H$_2$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(=NR$^{14}$)NR$^9$R$^9$, —NHC(=NR$^{14}$)NR$^{14}$R$^{14}$, —S(=O)R$^{10}$, —S(O)$_2$R$^{10}$, =O, —NR$^9$C(=O)OR$^8$ and —NR$^9$S(O$_2$)R$^8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R^{9a}$;

$R^8$, at each occurrence, is independently selected from the group consisting of alkyl, aryl, cycloalkyl, heteroaryl and heterocyclyl, each of which may be optionally substituted with one or more $R^{8a}$'s;

$R^{8a}$, at each occurrence, is independently selected from alkyl, haloalkyl, aryl, arylalkyl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

$R^9$, at each occurrence, is independently selected from hydrogen, alkyl, alkenyl, alkynyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R^{8a}$, and the heteroaryl, heteroarylalkyl, heterocyclyl and heterocyclylalkyl each contain 1-4 heteroatoms selected from N, O and S;

$R^{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(O)OR$^{14}$, —NR$^{14}$S(O$_2$)R$^{14}$, =O and arylalkyl;

$R^{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R^{10a}$, and the heteroaryl, heteroarylalkyl, heterocyclyl and heterocyclylalkyl each contain 1-4 heteroatoms selected from N, O and S;

$R^{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O) NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(O)R$^{14}$, —S(O)$_2$R$^{14}$, —NR$^{14}$C(O)OR$^{14}$, —NR$^{14}$S (O$_2$)R$^{14}$ and arylalkyl;

$R^{14}$, at each occurrence, is independently selected from hydrogen, alkyl, aryl, cycloalkyl, heteroaryl and heterocyclyl;

$R_{21}$, is hydrogen, alkyl, haloalkyl, hydroxyalkyl, aryl, cycloalkyl, halo, —CN, —C(=O)OH, —C(=O)OR$^{10}$, —OCF$_3$, —OCHF$_2$, —OR$^{10}$, —OH, —C(=O)NR$^9$R$^9$, —C(=O)R$^{10}$ or —OC(=O)R$^{10}$;

T$_1$ is hydrogen, halo, alkyl, aryl, alkenyl or alkynyl, wherein the alkyl, aryl, alkenyl and alkynyl may be optionally substituted with one or more R$^6$'s;

T$_2$ is hydrogen, alkyl, aryl, alkenyl or alkynyl, wherein the alkyl, aryl, alkenyl and alkynyl may be optionally substituted with one or more R$^6$'s;

T$_3$ is hydrogen, alkyl, aryl, alkenyl or alkynyl, wherein the alkyl, aryl, alkenyl and alkynyl may be optionally substituted with one or more R$^6$'s; and T$_4$ is hydrogen, halo, alkyl, aryl, alkenyl or alkynyl, wherein the alkyl, aryl, alkenyl and alkynyl may be optionally substituted with one or more R$^6$'s.

2. The compound, enantiomer, diastereomer, or a pharmaceutically acceptable salt thereof, of claim 1, wherein the compound of formula I is a compound of formula II(y):

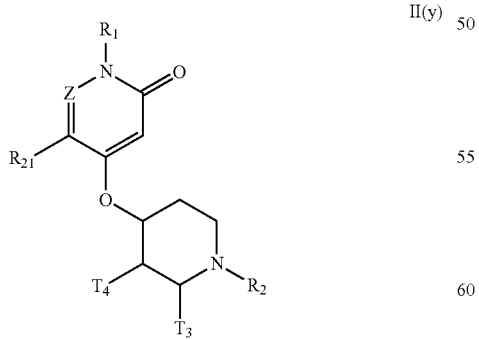

II(y)

wherein Z, R$_1$, R$_2$, R$_{21}$, T$^3$ and T$^4$ are defined as in claim 1.

3. The compound, enantiomer, diastereomer, or a pharmaceutically acceptable salt thereof, of claim 1, wherein the compound of formula I is a compound of formula II(z):

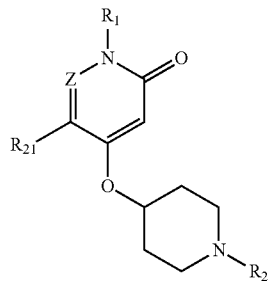

II(z)

wherein Z, R$_1$, R$_2$, and R$_{21}$ are defined as in claim 1.

4. The compound, enantiomer, diastereomer, or a pharmaceutically acceptable salt thereof, of claim 1, wherein:

Z is N;

R$^1$ is aryl, arylalkyl or heteroaryl, any of which may be optionally substituted with one or more R$^6$'s;

R$^2$ is cycloalkyl, aryl, heteroaryl, heterocyclyl, —S(O)$_2$R$^5$, —C(=O)R$^5$ or —C(=O)OR$^5$, wherein the cycloalkyl, aryl, heteroaryl and heterocyclyl may each be optionally substituted with one or more R$^6$'s;

R$^5$ is alkyl, alkenyl, aryl, cycloalkyl, heteroaryl or heterocyclyl, each of which may be optionally substituted with one or more R$^6$'s;

R$^6$, at each occurrence, is independently selected from alkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —S(O)$_3$H, —P(O)$_3$H$_2$, —C(=O) NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(=NR$^{14}$)NR$^9$R$^9$, —NHC (=NR$^{14}$)NR$^{14}$R$^{14}$, —S(=O)R$^{10}$, —S(O)$_2$R$^{10}$ and =O, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S (O)$_2$R$^{14}$, —S(O)$_2$NR$^{14}$C(=O)OR$^{14}$, —S(O)$_2$NR$^{14}$C (=O)NR$^{14}$R$^{14}$, —C(=O)NR$^{14}$S(O)$_2$CF$_3$, —C(=O) R$^{14}$, —NR$^{14}$C(=O)H, —NR$^{14}$C(=O)R$^{14}$, —OC (=O)R$^{14}$, —C(=NR$^{14}$)NR$^{14}$R$^{14}$, —NHC(=NR$^{14}$) NR$^{14}$R$^{14}$, —S(=O)R$^{14}$, —S(O)$_2$R$^{14}$, =O, —NR$^{14}$C (=O)OR$^{14}$ and —NR$^{14}$S(O$_2$)R$^{14}$;

R$^9$, at each occurrence, is independently selected from hydrogen, alkyl, alkenyl, alkynyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$^{8a}$, and the heteroaryl, heteroarylalkyl, heterocyclyl and heterocyclylalkyl each contain 1-4 heteroatoms selected from N, O and S;

$R^{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R^{10a}$, and the heteroaryl, heteroarylalkyl, heterocyclyl and heterocyclylalkyl each contain 1-4 heteroatoms selected from N, O and S;

$R^{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

$R^{14}$, at each occurrence, is independently selected from hydrogen, alkyl, aryl, cycloalkyl, heteroaryl and heterocyclyl;

$R_{21}$ is hydrogen, alkyl, haloalkyl, hydroxyalkyl, aryl, cycloalkyl, halo, —CN, —C(=O)OH, —C(=O)OR$^{10}$, —OCF$_3$, —OR$^{10}$, —OH, —C(=O)NR$^9$R$^9$, —C(=O)R$^{10}$ or —OC(=O)R$^{10}$;

$T_1$ is hydrogen, alkyl, aryl, alkenyl or alkynyl, wherein the alkyl, aryl, alkenyl and alkynyl may be optionally substituted with one or more $R^6$'s;

$T_2$ is hydrogen, alkyl, aryl, alkenyl or alkynyl, wherein the alkyl, aryl, alkenyl and alkynyl may be optionally substituted with one or more $R^6$'s;

$T_3$ is hydrogen, alkyl, aryl, alkenyl or alkynyl, wherein the alkyl, aryl, alkenyl and alkynyl may be optionally substituted with one or more $R^6$'s; and $T_4$ is hydrogen, alkyl, aryl, alkenyl or alkynyl, wherein the alkyl, aryl, alkenyl and alkynyl may be optionally substituted with one or more $R^6$'s.

5. The compound, enantiomer, diastereomer, or a pharmaceutically acceptable salt thereof, of claim 1, wherein:
Z is N;
$R^1$ is aryl, arylalkyl or heteroaryl, any of which may be optionally substituted with one or more $R^6$'s;
$R^2$ is cycloalkyl, aryl, heteroaryl, heterocyclyl, —C(=O)R$^5$ or —C(=O)OR$^5$, wherein the cycloalkyl, aryl, heteroaryl and heterocyclyl may each be optionally substituted with one or more $R^6$'s;

$R^5$ is alkyl, aryl, cycloalkyl, heteroaryl or heterocyclyl, each of which may be optionally substituted with one or more $R^6$'s;

$R^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —S(O)$_3$H, —P(O)$_3$H$_2$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(=NR$^{14}$)NR$^9$R$^9$, —NHC(=NR$^{14}$)NR$^{14}$R$^{14}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 $R^{9a}$;

$R^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, =O, —NR$^{14}$C(=O)OR$^{14}$ and —NR$^{14}$S(O)$_2$R$^{14}$;

$R^9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R^{8a}$, and the heteroaryl, heteroarylalkyl, heterocyclyl and heterocyclylalkyl each contain 1-4 heteroatoms selected from N, O and S;

$R^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

$R^{10}$, at each occurrence, is independently selected from alkyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R^{10a}$, and the heteroaryl, heteroarylalkyl, heterocyclyl and heterocyclylalkyl each contain 1-4 heteroatoms selected from N, O and S;

$R^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —S(O)$_3$H, —P(O)$_3$H$_2$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl, heteroaryl and heterocyclyl;

R$_{21}$ is hydrogen, alkyl, haloalkyl, hydroxyalkyl, aryl, cycloalkyl, halo, —CN, —C(=O)OH, —C(=O)OR$^{10}$, —OCF$_3$, —OR$^{10}$, —OH, —C(=O)NR$^9$R$^9$ or —C(=O)R$^{10}$;

T$_1$ is hydrogen, alkyl or aryl, wherein the alkyl or aryl may be optionally substituted with one or more R$^6$'s;

T$_2$ is hydrogen, alkyl or aryl, wherein the alkyl or aryl may be optionally substituted with one or more R$^6$'s;

T$_3$ is hydrogen, alkyl or aryl, wherein the alkyl or aryl may be optionally substituted with one or more R$^6$'s; and T$_4$ is hydrogen, alkyl or aryl, wherein the alkyl or aryl may be optionally substituted with one or more R$^6$'s.

6. The compound, enantiomer, diastereomer, or a pharmaceutically acceptable salt thereof, of claim 1, wherein:

Z is N;

R$^1$ is aryl, arylalkyl or heteroaryl, any of which may be optionally substituted with one or more R$^6$'s;

R$^2$ is aryl, heteroaryl, heterocyclyl, —C(=O)R$^5$ or —C(=O)OR$^5$, wherein the aryl, heteroaryl and heterocyclyl may each be optionally substituted with one or more R$^6$'s;

R$^5$ is alkyl, aryl, cycloalkyl or heteroaryl, each of which may be optionally substituted with one or more R$^6$'s;

R$^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —C(NR$^{14}$)NR$^9$R$^9$, —NHC(=NR$^{14}$)NR$^{14}$R$^{14}$, =S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

R$^9$, at each occurrence, is independently selected from hydrogen, alkyl, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$^{8a}$, and the heteroaryl, heteroarylalkyl, heterocyclyl and heterocyclylalkyl each contain 1-4 heteroatoms selected from N, O and S;

R$^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl, arylalkyl, heteroaryl, heteroarylalkyl and heterocyclyl, wherein the cycloalkyl, aryl, arylalkyl, heteroaryl, heteroarylalkyl and heterocyclyl may each be optionally substituted with 0-3 R$^{10a}$, and the heteroaryl, heteroarylalkyl and heterocyclyl each contain 1-4 heteroatoms selected from N, O and S;

R$^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —C(=NR$^{14}$)NR$^{14}$R$^{14}$, —NHC(=NR$^{14}$)NR$^{14}$R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl and heteroaryl;

R$_{21}$ is hydrogen, alkyl, haloalkyl, hydroxyalkyl, aryl, cycloalkyl, halo, —CN, —C(=O)OH, —C(=O)OR$^{10}$, —OR$^{10}$, —C(=O)NR$^9$R$^9$ or —C(=O)R$^{10}$;

T$_1$ is hydrogen or alkyl, wherein the alkyl may be optionally substituted with one or more R$^6$'s;

T$_2$ is hydrogen or alkyl, wherein the alkyl may be optionally substituted with one or more R$^6$'s;

T$_3$ is hydrogen, alkyl or aryl, wherein the alkyl or aryl may be optionally substituted with one or more R$^6$'s; and T$_4$ is hydrogen or alkyl, wherein the alkyl may be optionally substituted with one or more R$^6$'s.

7. The compound, enantiomer, diastereomer, or a pharmaceutically acceptable salt thereof, of claim 1, wherein:

Z is N;

R$^1$ is aryl, arylalkyl or heteroaryl, any of which may be optionally substituted with one or more R$^6$'s;

R$^2$ is aryl, heteroaryl, —C(=O)R$^5$ or —C(=O)OR$^5$, wherein the aryl and heteroaryl may each be optionally substituted with one or more R$^6$'s;

R$^5$ is alkyl, aryl or heteroaryl, each of which may be optionally substituted with one or more R$^6$'s;

R$^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —S(O)$_2$NR$^9$C(=O)NR$^9$R$^9$, —C(=O)NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, S(O)$_2$R$^{14}$, =O, —NR$^{14}$C(=O)OR$^{14}$ and —NR$^{14}$S(O$_2$)R$^{14}$;

R$^9$, at each occurrence, is independently selected from hydrogen, alkyl, cycloalkyl, aryl, arylalkyl, heteroaryl, heteroarylalkyl and heterocyclyl, wherein the alkyl, cycloalkyl, aryl, arylalkyl, heteroaryl, heteroarylalkyl and heterocyclyl may each be optionally substituted with 0-5 R$^{8a}$, and the heteroaryl, heteroarylalkyl and heterocyclyl each contain 1-4 heteroatoms selected from N, O and S;

R$^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl, arylalkyl, heteroaryl and heterocyclyl, wherein the cycloalkyl, aryl, arylalkyl, heteroaryl and heterocyclyl may each be optionally substituted with 0-3 R$^{10a}$, and the heteroaryl and heterocyclyl each contain 1-4 heteroatoms selected from N, O and S;

R$^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —S(O)$_2$NR$^{14}$C(=O)NR$^{14}$R$^{14}$, —C(=O)NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl and heteroaryl;

R$_{21}$ is hydrogen, alkyl, haloalkyl, hydroxyalkyl, aryl, halo, —CN, —C(=O)OH, —C(=O)OR$^{10}$, —OR$^{10}$, —C(=O)NR$^9$R$^9$ or —C(=O)R$^{10}$;

T$_1$ and T$_2$ are hydrogen;

T$_3$ is hydrogen, alkyl or aryl, wherein the alkyl or aryl may be optionally substituted with one or more R$^6$'s; and T$_4$ is hydrogen, alkyl or aryl, wherein the alkyl or aryl may be optionally substituted with one or more R$^6$'s.

8. The compound, enantiomer, diastereomer, or a pharmaceutically acceptable salt thereof, of claim 1, wherein:

Z is N;

R$^1$ is aryl, arylalkyl or heteroaryl, any of which may be optionally substituted with one or more R$^6$'s;

R$^2$ is aryl, heteroaryl or —C(=O)OR$^5$, wherein the aryl and heteroaryl may each be optionally substituted with one or more R$^6$'s;

R$^5$ is alkyl, aryl or heteroaryl, each of which may be optionally substituted with one or more R$^6$'s;

R$^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)NR$^9$S(O)$_2$R$^9$, —S(O)$_2$NR$^9$C(=O)OR$^9$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{14}$, —S(O)$_2$NR$^{14}$C(=O)OR$^{14}$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

R$^9$, at each occurrence, is independently selected from hydrogen, alkyl, cycloalkyl, aryl, arylalkyl, heteroaryl and heterocyclyl, wherein the alkyl, cycloalkyl, aryl, arylalkyl, heteroaryl, and heterocyclyl may each be optionally substituted with 0-5 R$^{8a}$, and the heteroaryl and heterocyclyl each contain 1-4 heteroatoms selected from N, O and S;

R$^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^{10}$, —S(O)$_2$NR$^{14}$C(=O)OR$^{10}$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl, heteroaryl and heterocyclyl, wherein the cycloalkyl, aryl, heteroaryl and heterocyclyl may each be optionally substituted with 0-3 R$^{10a}$, and the heteroaryl and heterocyclyl each contain 1-4 heteroatoms selected from N, O and S;

R$^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)NR$^{14}$S(O)$_2$R$^9$, —S(O)$_2$NR$^{14}$C(=O)OR$^9$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl and heteroaryl;

R$_{21}$ is hydrogen, alkyl, haloalkyl, hydroxyalkyl, aryl, halo, —CN, —C(=O)OR$^{10}$, —OR$^{10}$, —C(=O)NR$^9$R$^9$ or —C(=O)R$^{10}$;

T$_1$, T$_2$ and T$_4$ are hydrogen; and

T$_3$ is hydrogen, alkyl or aryl, wherein the alkyl or aryl may be optionally substituted with one or more R$^6$'s.

9. The compound, enantiomer, diastereomer, or a pharmaceutically acceptable salt thereof, of claim 1, wherein:

Z is N;

R$^1$ is aryl, arylalkyl or heteroaryl, any of which may be optionally substituted with one or more R$^6$'s;

R$^2$ is heteroaryl or —C(=O)OR$^5$, wherein the heteroaryl may be optionally substituted with one or more R$^6$'s;

R$^5$ is alkyl, aryl or heteroaryl, each of which may be optionally substituted with one or more R$^6$'s;

R$^6$, at each occurrence, is independently selected from alkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, cycloalkylalkyl, heteroaryl, heteroarylalkyl, heterocyclyl and heterocyclylalkyl may each be optionally substituted with 0-5 R$^{9a}$;

R$^{8a}$, at each occurrence, is independently selected from alkyl, haloalkyl, aryl, arylalkyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

R$^9$, at each occurrence, is independently selected from hydrogen, alkyl, cycloalkyl, aryl, heteroaryl and heterocyclyl, wherein the alkyl, cycloalkyl, aryl, heteroaryl and heterocyclyl may each be optionally substituted with 0-5 R$^{8a}$, and the heteroaryl and heterocyclyl each contain 1-4 heteroatoms selected from N, O and S;

R$^{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl and heteroaryl, wherein the cycloalkyl, aryl and heteroaryl may each be optionally substituted with 0-3 R$^{10a}$, and the heteroaryl contains 1-4 heteroatoms selected from N, O and S;

R$^{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl and heteroaryl;

R$_{21}$ is hydrogen, alkyl, haloalkyl, hydroxyalkyl, aryl, halo, —CN, —C(=O)OR$^{10}$, —C(=O)NR$^9$R$^9$ or —C(=O)R$^{10}$;

T$_1$, T$_2$ and T$_4$ are hydrogen; and

T$_3$ is hydrogen or alkyl, wherein the alkyl may be optionally substituted with one or more R$^6$'s.

10. The compound, enantiomer, diastereomer, or a pharmaceutically acceptable salt thereof, of claim 1, wherein:

Z is N;

R$^1$ is aryl or heteroaryl, any of which may be optionally substituted with one or more R$^6$'s;

R$^2$ is heteroaryl or —C(=O)OR$^5$, wherein the heteroaryl may be optionally substituted with one or more R$^6$'s;

R$^5$ is alkyl, aryl or heteroaryl, each of which may be optionally substituted with one or more R$^6$'s;

R$^6$, at each occurrence, is independently selected from alkyl, aryl, cycloalkyl, heteroaryl, heterocyclyl, halo, —NH$_2$, —CN, —NO$_2$, —C(=O)OH, —C(=O)OR$^{10}$, —OCF$_3$, —OCHF$_2$, —OR$^{10}$, —OH, —SH, —SR$^{10}$, —C(=O)NR$^9$R$^9$, —NR$^9$R$^9$, —S(O)$_2$NR$^9$R$^9$, —NR$^9$S(O)$_2$CF$_3$, —C(=O)R$^{10}$, —NR$^9$C(=O)H, —NR$^9$C(=O)R$^{10}$, —OC(=O)R$^{10}$, —S(=O)R$^{10}$, —S(O)$_2$R$^{10}$ and =O, wherein the alkyl, aryl, cycloalkyl, heteroaryl, and heterocyclyl may each be optionally substituted with 0-5 R$^{9a}$;

R$^{8a}$, at each occurrence, is independently selected from alkyl, haloalkyl, aryl, arylalkyl, cycloalkyl, heteroaryl, heterocyclyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, =O, —NR$^{14}$C(=O)OR$^{14}$ and —NR$^{14}$S(O$_2$)R$^{14}$;

R$^9$, at each occurrence, is independently selected from hydrogen, alkyl, cycloalkyl, aryl and heteroaryl, wherein the alkyl, cycloalkyl, aryl and heteroaryl, may each be optionally substituted with 0-5 R$^{8a}$, and the heteroaryl contains 1-4 heteroatoms selected from N, O and S;

R$^{9a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$, =O and arylalkyl;

R$^{10}$, at each occurrence, is independently selected from alkyl, cycloalkyl, aryl and heteroaryl, wherein the cycloalkyl, aryl and heteroaryl may each be optionally substituted with 0-3 R$^{10a}$, and the heteroaryl contains 1-4 heteroatoms selected from N, O and S;

R$^{10a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)OR$^{14}$, —OCF$_3$, —OCHF$_2$, —OR$^{14}$, —OH, —SH, —SR$^{14}$, —C(=O)NR$^{14}$R$^{14}$, —NR$^{14}$R$^{14}$, —S(O)$_2$NR$^{14}$R$^{14}$, —NR$^{14}$S(O)$_2$CF$_3$, —C(=O)R$^{14}$, —NR$^{14}$C(=O)H, —NR$^{14}$C(=O)R$^{14}$, —OC(=O)R$^{14}$, —S(=O)R$^{14}$, —S(O)$_2$R$^{14}$, —NR$^{14}$C(=O)OR$^{14}$, —NR$^{14}$S(O$_2$)R$^{14}$ and arylalkyl;

R$^{14}$, at each occurrence, is independently selected from hydrogen, alkyl, aryl, cycloalkyl and heteroaryl;

R$_{21}$ is hydrogen, alkyl, haloalkyl, hydroxyalkyl, aryl, halo, —CN, —C(=O)OR$^{10}$ or —C(=O)NR$^9$R$^9$;

T$_1$, T$_2$ and T$_4$ are hydrogen; and

T$_3$ is hydrogen or alkyl.

11. The compound of claim 1, wherein the compound is selected from the group consisting of:

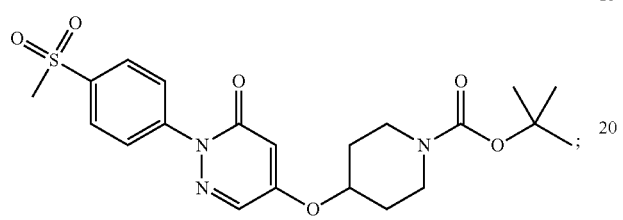

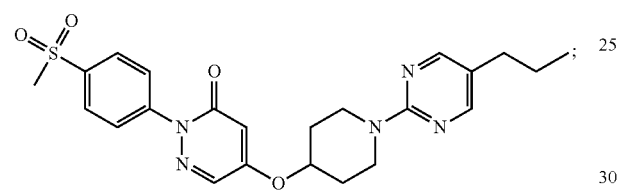

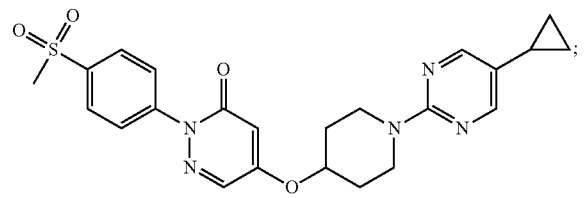

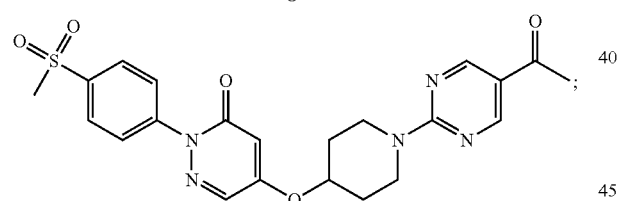

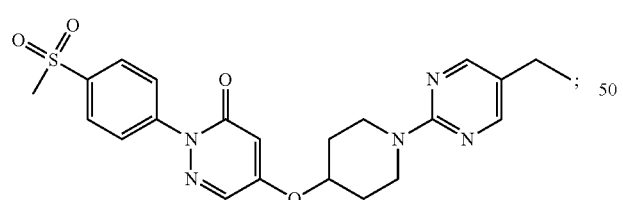

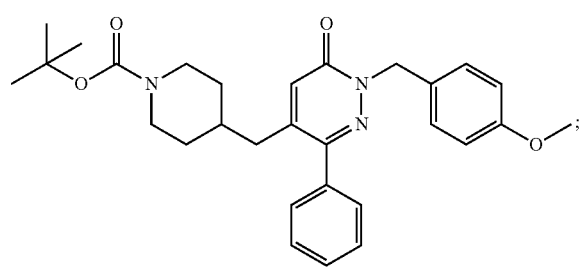

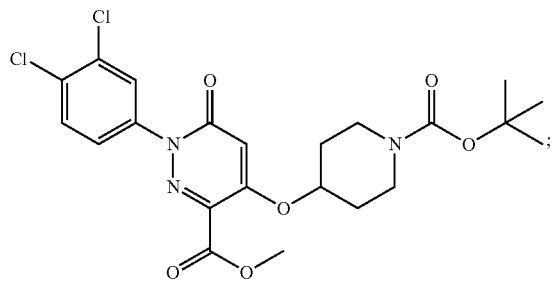

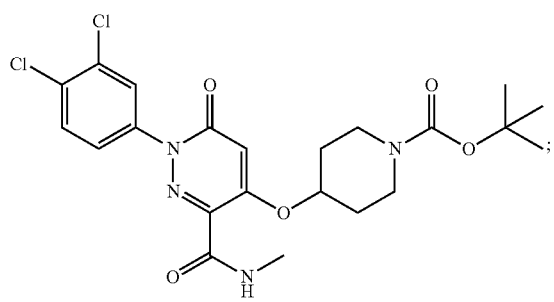

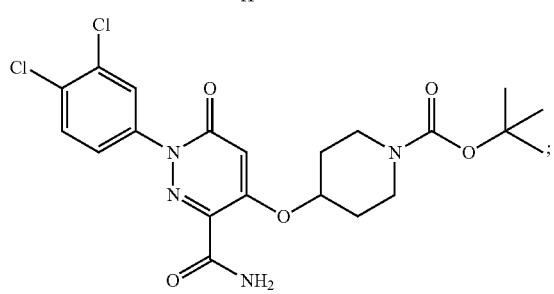

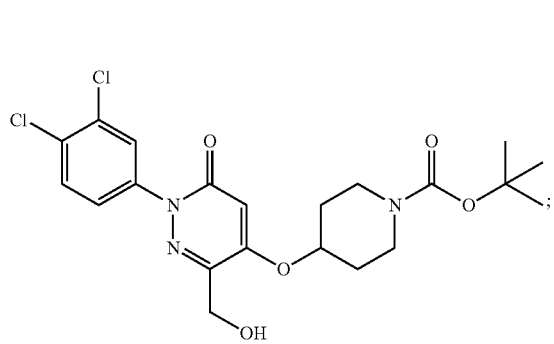

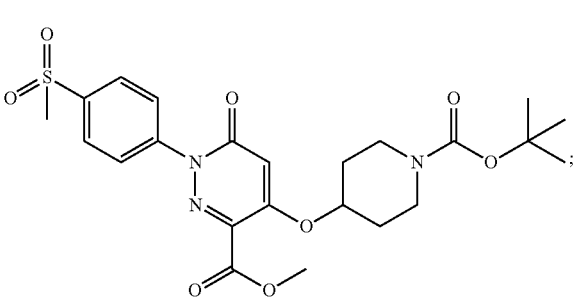

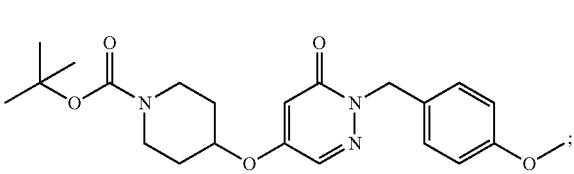

109
-continued
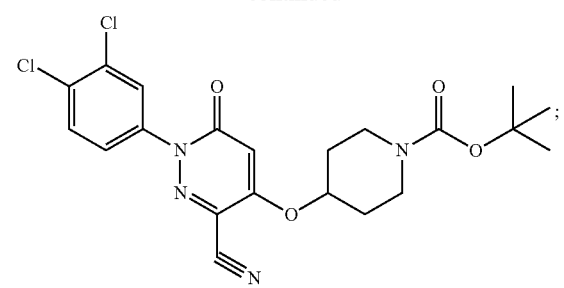
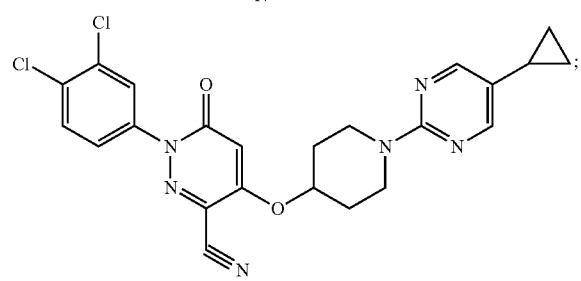
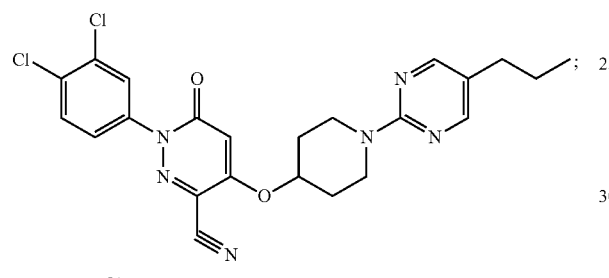
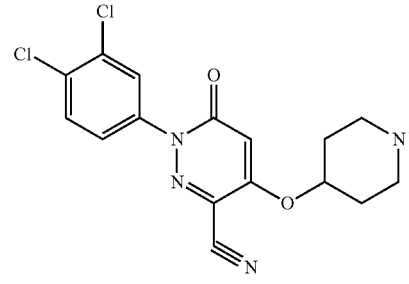
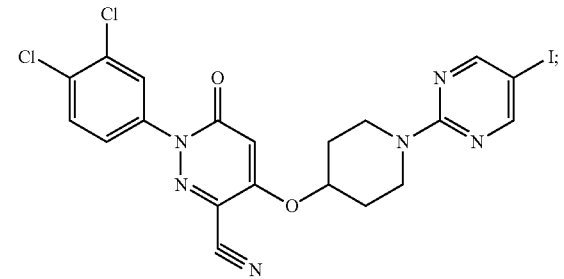
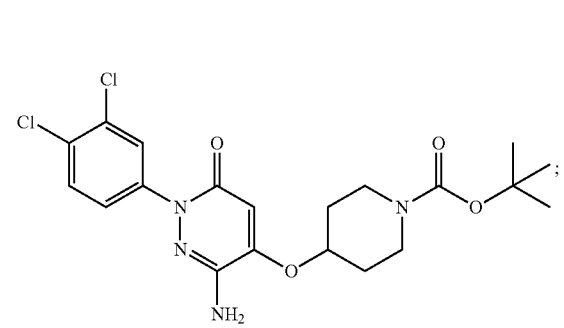
110
-continued
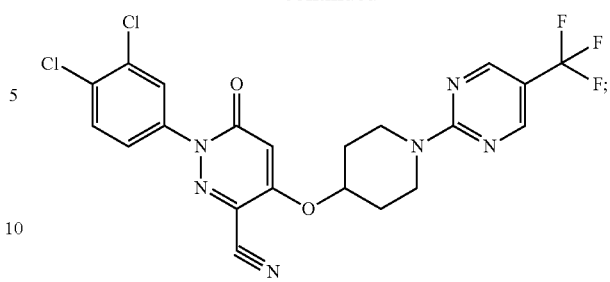
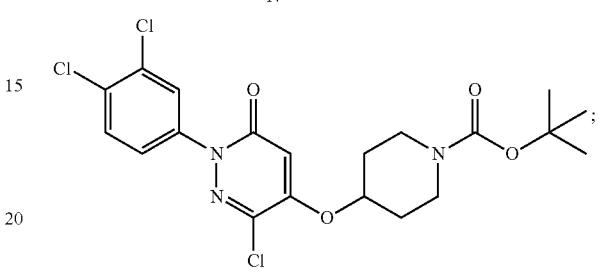
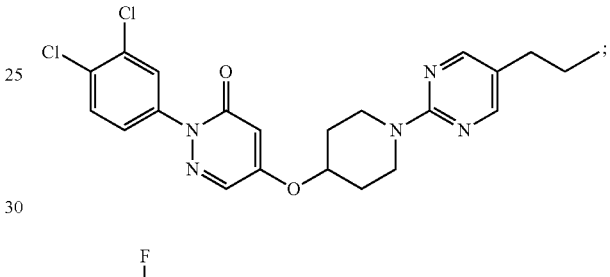
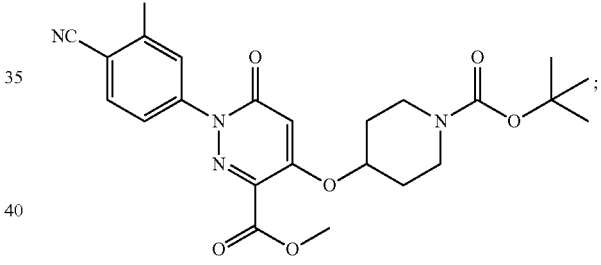
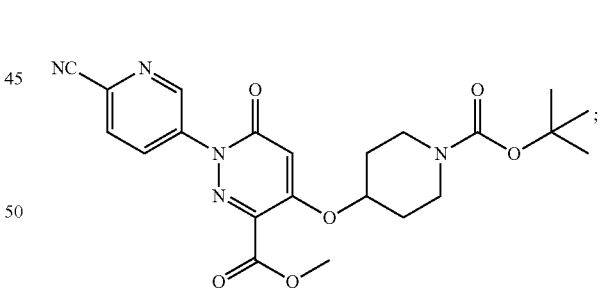
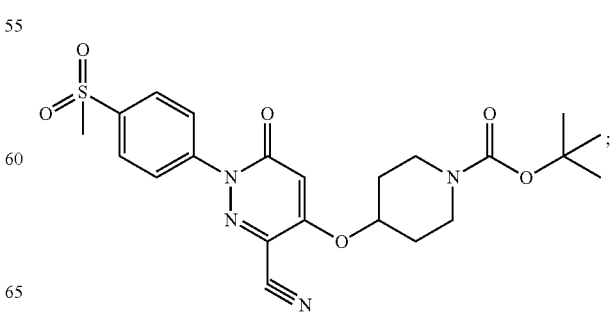

111
-continued
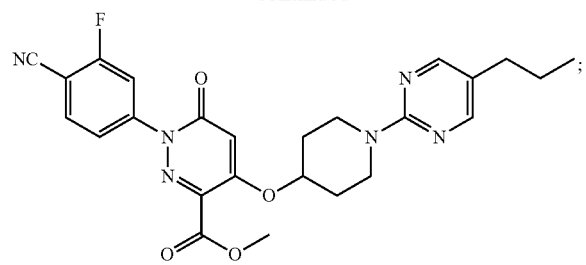
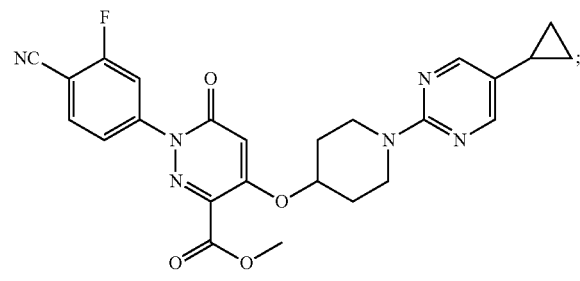
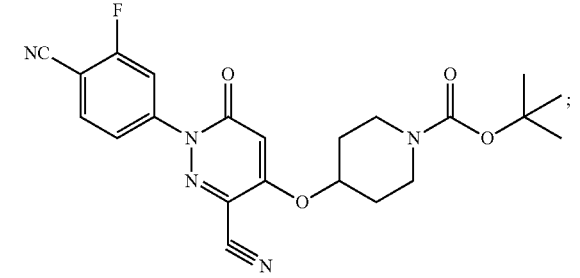
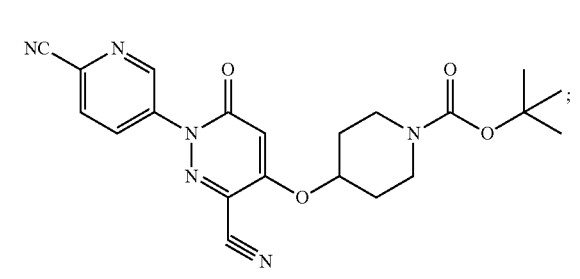
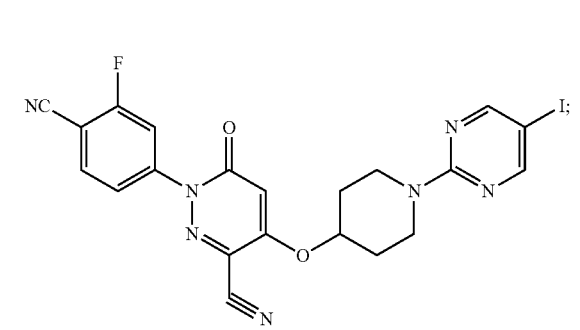
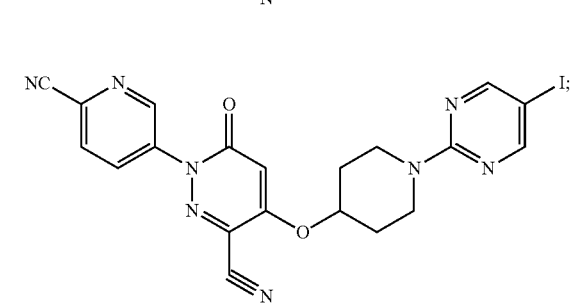
112
-continued
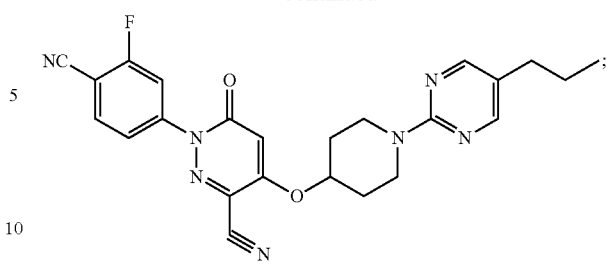
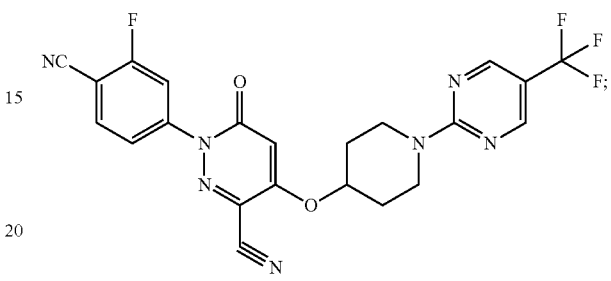
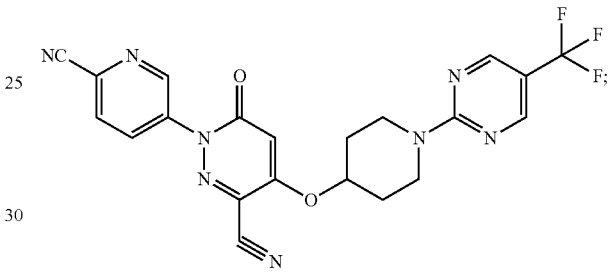
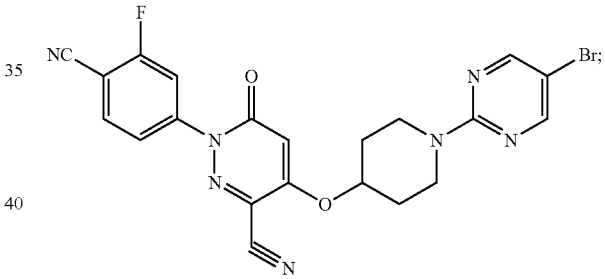
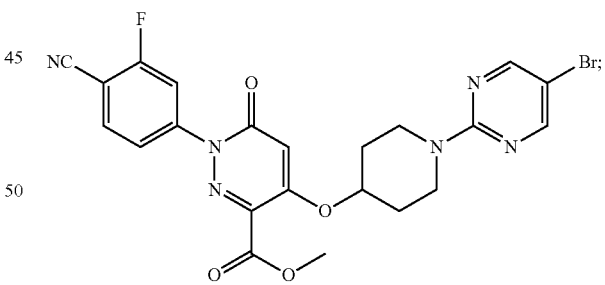
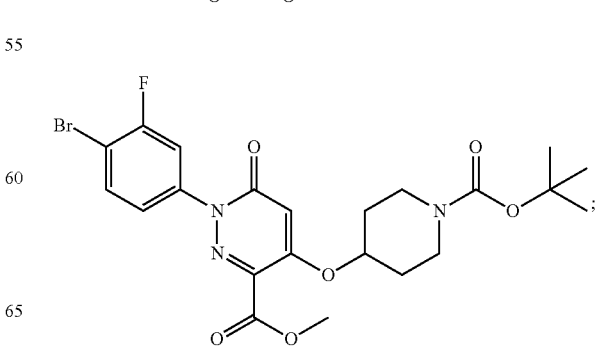

113
-continued
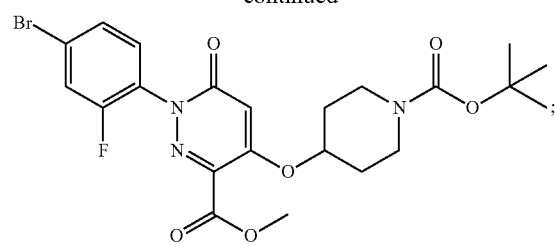
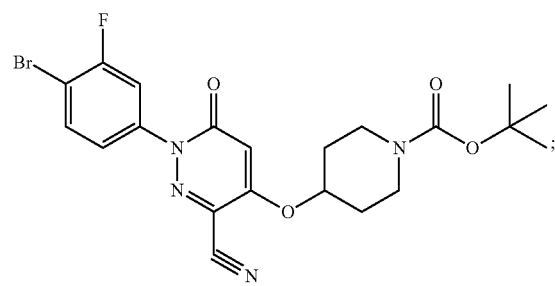
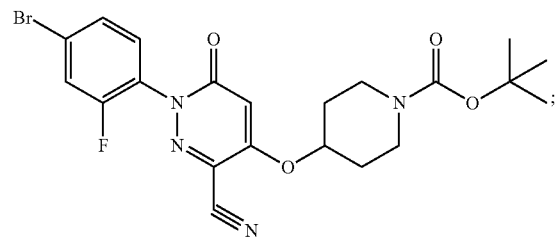
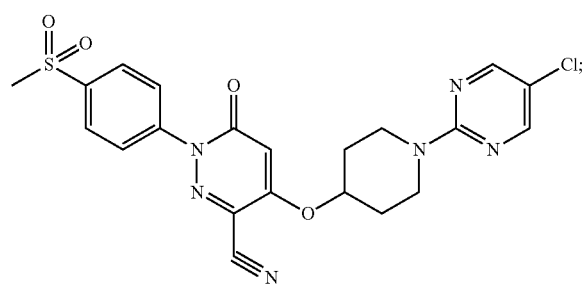
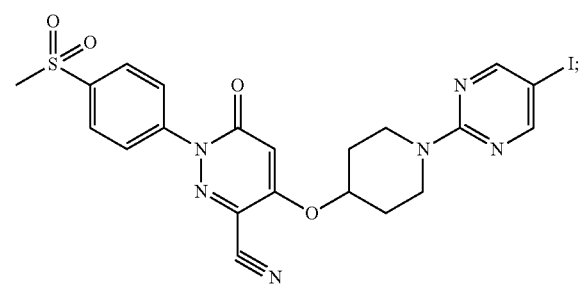
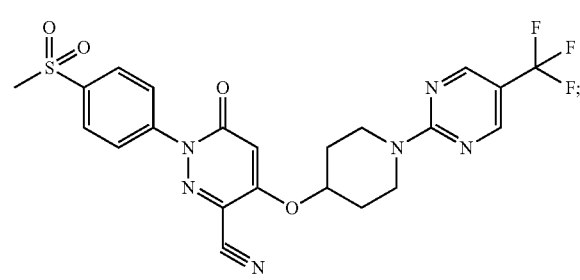
114
-continued
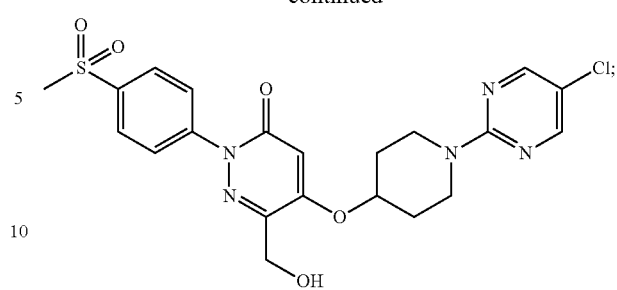
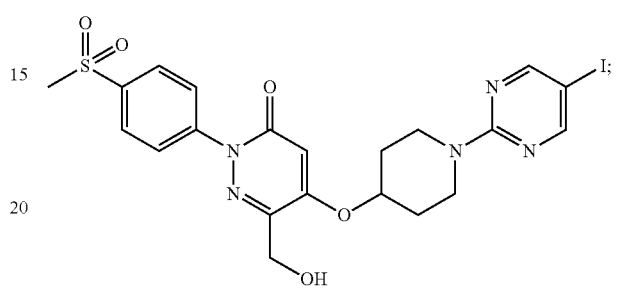
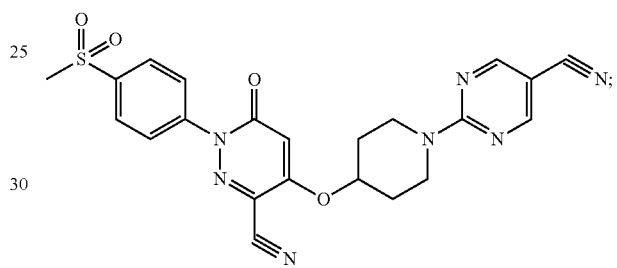
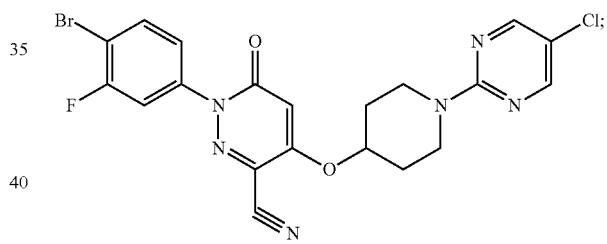
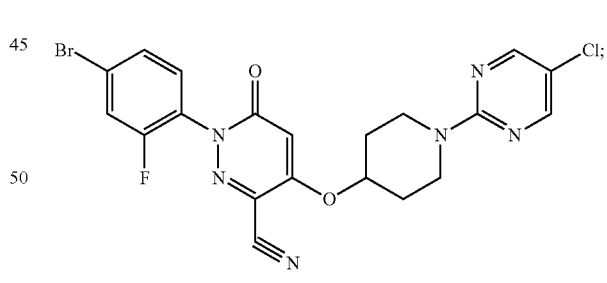
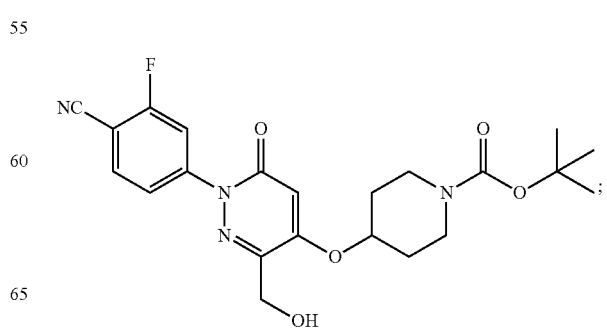

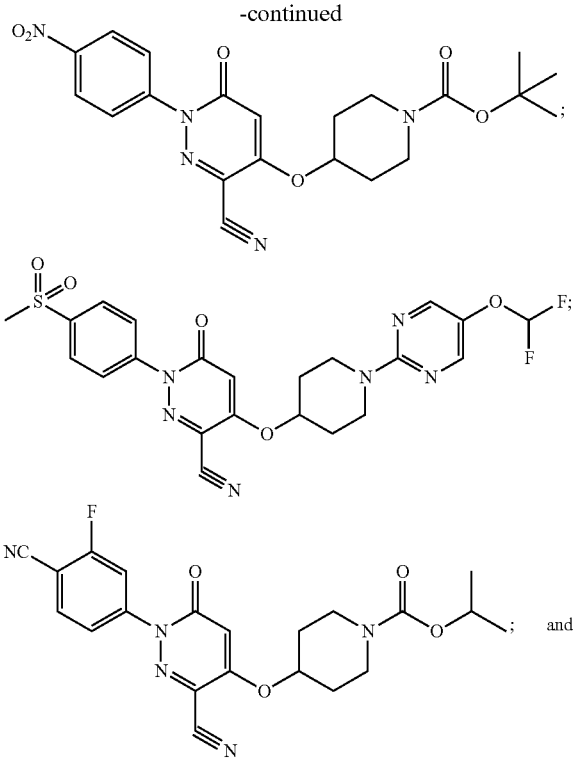

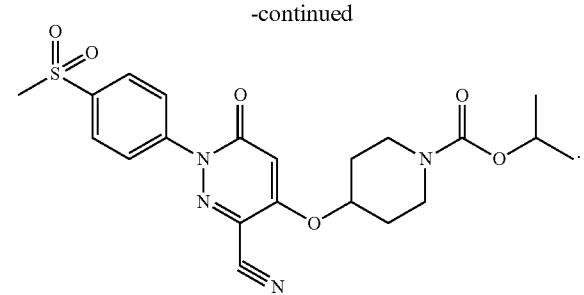

12. A pharmaceutical composition comprised of a therapeutically effective amount of a compound of claim 1, or an enantiomer, a diastereomer, or a pharmaceutically acceptable salt thereof, and optionally a pharmaceutically acceptable carrier.

13. The pharmaceutical composition of claim 12, further comprising a therapeutically effective amount of one or more other therapeutically active agents.

14. A pharmaceutical composition comprised of a therapeutically effective amount of a compound of claim 11, or an enantiomer, a diastereomer, or a pharmaceutically acceptable salt thereof, and optionally a pharmaceutically acceptable carrier.

15. The pharmaceutical composition of claim 14, further comprising a therapeutically effective amount of one or more other therapeutically active agents.

* * * * *

UNITED STATES PATENT AND TRADEMARK OFFICE
CERTIFICATE OF CORRECTION

PATENT NO. : 8,372,837 B2
APPLICATION NO. : 13/003914
DATED : February 12, 2013
INVENTOR(S) : Dean A. Wacker et al.

It is certified that error appears in the above-identified patent and that said Letters Patent is hereby corrected as shown below:

On the Title Page:

Item (57) ABSTRACT:

Column 2, line 3 (Abstract), change "$R^1$, $R^2$, $R^{21}$, $T^1$, $T^2$, $T^3$ and $T^4$" to -- $R_1$, $R_2$, $R_{21}$, $T_1$, $T_2$, $T_3$ and $T_4$ --.

In the Claims:

Claim 1:

Column 96, line 41, change "$NR^{14}C(=O)R^{14}$," to -- $-NR^{14}C(=O)R^{14}$, --.

Column 96, line 63, after "$-C(=O)R^{14}$," insert -- $-NR^{14}C(=O)H$, --.

Column 96, line 66, change "$-NR^{14}C(O)OR^{14}$," to -- $-NR^{14}C(=O)OR^{14}$, --.

Column 97, line 23, change "$-S(O)R^{14}$," to -- $-S(=O)R^{14}$, --.

Column 97, line 23, change "$-NR^{14}C(O)OR^{14}$," to -- $-NR^{14}C(=O)OR^{14}$, --.

Claim 6:

Column 101, line 45, change "$-C(NR^{14})NR^9R^9$," to -- $-C(=NR^{14})NR^9R^9$, --.

Column 101, line 46, change "$=S(=O)R^{10}$," to -- $-S(=O)R^{10}$, --.

Column 101, line 60, change "$-NR^{14}C(O)R^{14}$," to -- $-NR^{14}C(=O)R^{14}$, --.

Claim 7:

Column 102, line 66, after "$-OCHF_2$," insert -- $-OR^{10}$, --.

Column 103, line 18, change "$S(O)_2R^{14}$," to -- $-S(O)_2R^{14}$, --.

Claim 9:

Column 105, line 39, change "$-NR^{14}C(=O)_H$," to -- $-NR^{14}C(=O)H$, --.

Signed and Sealed this
Fourteenth Day of July, 2015

Michelle K. Lee
*Director of the United States Patent and Trademark Office*

CERTIFICATE OF CORRECTION (continued)
U.S. Pat. No. 8,372,837 B2

In the Claims:

Claim 9:

Column 107, lines 57 to 66, change

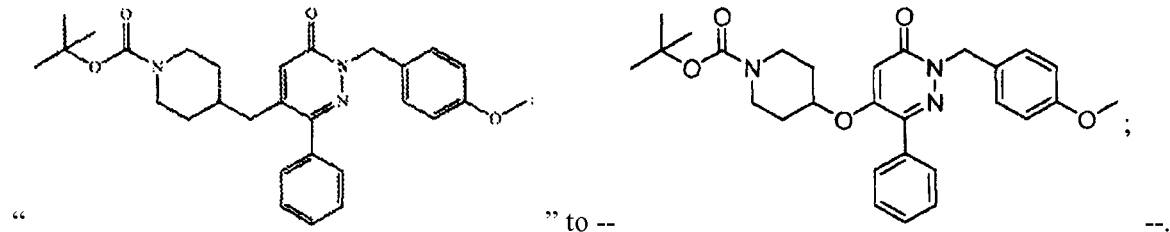

" to -- --.